(12) United States Patent
Vodyanyk et al.

(10) Patent No.: US 10,947,502 B2
(45) Date of Patent: Mar. 16, 2021

(54) METHODS FOR DIRECTED DIFFERENTIATION OF PLURIPOTENT STEM CELLS TO IMMUNE CELLS

(71) Applicant: FUJIFILM Cellular Dynamics, Inc., Madison, WI (US)

(72) Inventors: Maksym A. Vodyanyk, Madison, WI (US); Xin Zhang, Madison, WI (US); Andrew J. Brandl, Madison, WI (US); Deepika Rajesh, Madison, WI (US); Bradley Swanson, Madison, WI (US); Christie Munn, Madison, WI (US); Sarah A. Burton, Madison, WI (US); Wen Bo Wang, Madison, WI (US)

(73) Assignee: FUJIFILM Cellular Dynamics, Inc., Madison, WI (US)

( * ) Notice: Subject to any disclaimer, the term of this patent is extended or adjusted under 35 U.S.C. 154(b) by 0 days.

(21) Appl. No.: 15/769,386

(22) PCT Filed: Oct. 20, 2016

(86) PCT No.: PCT/US2016/057899
§ 371 (c)(1),
(2) Date: Apr. 19, 2018

(87) PCT Pub. No.: WO2017/070337
PCT Pub. Date: Apr. 27, 2017

(65) Prior Publication Data
US 2018/0305664 A1 Oct. 25, 2018

Related U.S. Application Data

(60) Provisional application No. 62/404,470, filed on Oct. 5, 2016, provisional application No. 62/244,101, filed on Oct. 20, 2015.

(51) Int. Cl.
| *C12N 5/0783* | (2010.01) |
| *C12N 5/0784* | (2010.01) |
| *C12N 5/0789* | (2010.01) |
| *C12N 5/0781* | (2010.01) |
| *C12N 15/85* | (2006.01) |
| *C12N 15/86* | (2006.01) |

(52) U.S. Cl.
CPC ......... *C12N 5/0636* (2013.01); *C12N 5/0635* (2013.01); *C12N 5/0637* (2013.01); *C12N 5/0638* (2013.01); *C12N 5/0639* (2013.01); *C12N 5/0646* (2013.01); *C12N 5/0647* (2013.01); *C12N 15/85* (2013.01); *C12N 15/86* (2013.01); *C12N 2500/38* (2013.01); *C12N 2500/90* (2013.01); *C12N 2501/115* (2013.01); *C12N 2501/125* (2013.01); *C12N 2501/145* (2013.01); *C12N 2501/155* (2013.01); *C12N 2501/165* (2013.01); *C12N 2501/22* (2013.01); *C12N 2501/2303* (2013.01); *C12N 2501/2306* (2013.01); *C12N 2501/2307* (2013.01); *C12N 2501/25* (2013.01); *C12N 2501/26* (2013.01); *C12N 2501/60* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2501/727* (2013.01); *C12N 2501/998* (2013.01); *C12N 2501/999* (2013.01); *C12N 2506/025* (2013.01); *C12N 2506/03* (2013.01); *C12N 2506/09* (2013.01); *C12N 2506/11* (2013.01); *C12N 2506/45* (2013.01); *C12N 2510/00* (2013.01); *C12N 2533/50* (2013.01); *C12N 2840/20* (2013.01)

(58) Field of Classification Search
CPC .. C12N 5/0636; C12N 5/0635; C12N 5/0646; C12N 2506/03
See application file for complete search history.

(56) References Cited

U.S. PATENT DOCUMENTS

| 5,486,359 | A | 1/1996 | Caplan et al. |
| 5,556,954 | A | 9/1996 | Burn et al. |
| 5,843,780 | A | 12/1998 | Thomson |
| 5,908,782 | A | 6/1999 | Marshak et al. |
| 6,200,806 | B1 | 3/2001 | Thomson |
| 7,029,913 | B2 | 4/2006 | Thomson |
| 7,442,548 | B2 | 10/2008 | Thomson et al. |
| 8,058,065 | B2 | 11/2011 | Yamanaka et al. |
| 8,071,369 | B2 | 12/2011 | Jaenisch et al. |
| 8,129,187 | B2 | 3/2012 | Yamanaka et al. |
| 8,183,038 | B2 | 5/2012 | Thomson et al. |
| 8,268,620 | B2 | 9/2012 | Thomson et al. |

(Continued)

FOREIGN PATENT DOCUMENTS

| AU | 2015200413 | 2/2015 |
| EP | 1507865 | 7/2008 |

(Continued)

OTHER PUBLICATIONS

D'Souza et al., Stem Cell Reports. Feb. 9, 2016;6(2):243-256 (Year: 2016).*

(Continued)

*Primary Examiner* — Daniel C Gamett
(74) *Attorney, Agent, or Firm* — Parker Highlander PLLC

(57) ABSTRACT

Provided herein are methods for the efficient in vitro differentiation of somatic cell-derived pluripotent stem cells to hematopoietic precursor cells, and the further differentiation of the hematopoietic precursor cells into immune cells of various myeloid or lymphoid lineages, particularly T cells, NK cells, and dendritic cells. The pluripotent cells may be maintained and differentiated under defined conditions; thus, the use of mouse feeder cells or serum is not required in certain embodiments for the differentiation of the hematopoietic precursor cells.

25 Claims, 40 Drawing Sheets

(56) References Cited

U.S. PATENT DOCUMENTS

| | | | |
|---|---|---|---|
| 8,372,642 | B2 | 2/2013 | Rajesh et al. |
| 8,546,140 | B2 | 10/2013 | Mack et al. |
| 8,691,574 | B2 | 4/2014 | Mack |
| 8,741,648 | B2 | 6/2014 | Rajesh et al. |
| 8,900,871 | B2 | 12/2014 | Okita et al. |
| 9,127,256 | B2 | 9/2015 | Fusaki et al. |
| 9,175,268 | B2 | 11/2015 | Mack |
| 9,206,389 | B2 | 12/2015 | Lazzari et al. |
| 9,206,394 | B2 | 12/2015 | Nakauchi et al. |
| 2002/0055144 | A1 | 5/2002 | Wei et al. |
| 2003/0211603 | A1 | 11/2003 | Earp et al. |
| 2006/0084168 | A1* | 4/2006 | Thomson ............ C12N 5/0606 435/366 |
| 2007/0077654 | A1 | 4/2007 | Thomson et al. |
| 2008/0299095 | A1 | 12/2008 | Humphries et al. |
| 2009/0068742 | A1 | 3/2009 | Yamanaka |
| 2009/0148425 | A1 | 6/2009 | Ohmori et al. |
| 2009/0246875 | A1 | 10/2009 | Yamanaka et al. |
| 2010/0210014 | A1 | 8/2010 | Yamanaka |
| 2010/0279403 | A1 | 11/2010 | Rajesh et al. |
| 2011/0104125 | A1 | 5/2011 | Yu |
| 2011/0287538 | A1 | 11/2011 | Fusaki et al. |
| 2012/0276636 | A1 | 11/2012 | Yamanaka et al. |
| 2013/0210150 | A1 | 8/2013 | Ban et al. |
| 2014/0273211 | A1 | 9/2014 | Sluvkin et al. |
| 2014/0315304 | A1 | 10/2014 | Brown et al. |
| 2014/0322808 | A1 | 10/2014 | Keller et al. |
| 2015/0191697 | A1 | 7/2015 | Stankewicz et al. |
| 2016/0280809 | A1 | 9/2016 | Stoerkle et al. |
| 2018/0072992 | A1* | 3/2018 | Valamehr ............ C12N 5/0636 |

FOREIGN PATENT DOCUMENTS

| | | |
|---|---|---|
| WO | WO 1996/039487 | 12/1996 |
| WO | WO 2006/020889 | 2/2006 |
| WO | WO 2006/050330 | 5/2006 |
| WO | WO 2007/069666 | 6/2007 |
| WO | WO 2009-135206 | 11/2009 |
| WO | WO 2009/137624 | 11/2009 |
| WO | WO 2010/008054 | 1/2010 |
| WO | WO 2010/099539 | 9/2010 |
| WO | WO 2012/029770 | 3/2012 |
| WO | WO 2012/109208 | 8/2012 |
| WO | WO 2014/153069 | 9/2014 |
| WO | WO 2014/165707 | 10/2014 |
| WO | WO 2015/164740 | 10/2015 |
| WO | WO 2016/115407 | 7/2016 |
| WO | WO 2017/070337 | 4/2017 |

OTHER PUBLICATIONS

Sturgeon et al., Nat. Biotechnol. 2014;32:554-561 (Year: 2014).*
Abboud et al., "Hydrophobic adsorption chromatography of colony-stimulating activities and erythroid-enhancing activity from the human monocyte-like cell line, GCT," *Blood*, 58: 1148-1154, 1981.
Akkina et al., "High-efficiency gene transfer into CD34+ cells with a human immunodeficiency virus type 1-based retroviral vector pseudotyped with vesicular stomatitis virus envelope glycoprotein G," *J. Virol.*, 70:2581-2585, 1996.
Amedola et al., "Coordinate dual-gene transgenesis by lentiviral vectors carrying synthetic bidirectional promoters," *Nature Biotechnology*, 23(1):108-116, 2005.
Amit et al., "Clonally Derived Human Embryonic Stem Cell Lines Maintain Pluripotency and Proliferative Potential for Prolonged Periods of Culture," *Develop. Biol.*, 227:271-278, 2000.
Aoki et al., "Regualtion of DNA Demethylation during Maturation of CD4+ Native T Cells by the Conserved Noncoding Sequence 1," *J. Immunol.*, 182:7698-7707, 2009.
Ayllon et al., "The Notch ligand DLL4 specifically marks human hematoendothelial progenitors and regulates their hematopoietic fate," *Leukemia*, 29(8):1741-1753, 2015.
Batta et al., "Direct Reprogramming of Murine Fibroblasts to Hematopoietic Progenitor Cells," *Cell Rep.*, 9(5):1871-1884, 2014.

Bauer et al., "Reawakening fetal hemoglobin: prospects for new therapies for the β-globin disorders," *Blood*, 120(15):2945-2953, 2012.
Bhatnagar, et al. "Genetic and pharmacological reactivation of the mammalian inactive X chromosome," *Proc. Natl. Acad. Sci. USA*, 111(35):12591-8, 2014.
Bird, "The methyl-CpG-binding protein MeCP2 and neurological disease," *Biochem. Soc. Trans.*, 36:575-583, 2008.
Biswas et al., "Diagnostic application of polymerase chain reaction for detection of Ehrlichia risticii in equine monocytic ehrlichiosis (Potomac horse fever)," *J. Clin. Microbiol.*, 29:2228-2233, 1991.
Biswas et al., "Gene amplification by polymerase chain reaction for detection of Ehrlichia risticii DNA in Potomac horse fever," *Annals NY Acad. Sci.*, 590:582-583, 1990.
Carrio et al., "DNA methylation dynamics in muscle development and disease," *Front. Aging. Neurosci.*, 7(19), 12 pages, 2015.
Chang et al., "Broad T-cell receptor repertoire in T-lymphocytes derived from human induced pluripotent stem cells," *PLOS ONE*, 9(5):e97335, 2014.
Chen et al., "Development of hematopoietic stem and progenitor cells from human pluripotent stem cells," *Journal of Cellular Biochemistry*, 116(7):1179-1189.
Cheng et al., "Self-Renewing Endodermal Progenitor Lines Generated from Human Pluripotent Stem Cells," *Cell Stem Cell*, 10(4):371-384, 2012.
Choi et al., "Hematopoietic differentiation and production of mature myeloid cells from human pluripotent stem cells," *Nature Protocols*, 6(3):296-313, 2011.
Chung et al., "Undifferentiated hematopoietic cells are characterized by a genome-wide underrmethylation dip around the transcription start site and a hierarchical epigenetic plasticity," *Blood*, 114(24):4968-4978, 2009.
De Paz et al., "Circadian Cycle-Dependent MeCP2 and Brain Chromatin Changes," *PLoS One*, 10(4):e0123693, 2015.
Ditadi et al., "Human definitive haemogenic endothelium and arterial vascular endothelium represent distinct lineages," *Nature Cell Biol*, 7(5):580-591 and supporting information, 2015.
Doulatov et al., "Hematopoiesis: A Human Perspective," *Cell Stem Cell*, 10:120-36, 2012.
Doulatov et al., "Induction of multipotential hematopoietic progenitors from human pluripotent stem cells via respecification of lineage-restricted precursors," *Cell Stem Cell*, 13(4):459-470, 2013.
Doulatov et al., "Revised map of the human progenitor hierarchy shows the origin of macrophages and dendritic cells in early lymphoid development," *Nature Immunol.*, 11(7):585-593, 2010.
Du Pré et al., "Circadian Rhythms in Cell Maturation," *Physiology*, 29:72-83, 2014.
Ebina et al., "Transcription factor-mediated reprogramming toward hematopoietic stem cells," *EMBO Journal*, 34(6):694-709, 2015.
Elcheva et al., "Direct induction of haematoendothelial programs in human pluripotent stem cells by transcriptional regulators," *Nat Commun*, 5:4372, 2014.
Encabo et al., "Selective generation of different dendritic cell precursors from CD34+ cells by interleukin-6 and interleukin-3," *Stem Cells*, 22(5):725-740, 2004.
Evans et al., "Cancer of the pancreas," In: Cancer Principles and Practice of Oncology, Devita et al. (Eds.), Lippincot-Raven, NY, 1054-1087, 1997.
Fauser et al., "Stimulatory activity for human pluripotent hemopoietic progenitors produced by a human T-lymphocyte cell line," *Stem Cells*, 1(2):73-80, 1981.
Feng et al., "Scalable generation of universal platelets from human induced pluripotent stem cells," *Stem Cell Reports*, 3(5):817-831, 2014.
Frisan et al., "Generation of Lymphoblastoid Cell Lines (LCLs)," In: Epstein-Barr Virus Protocols, Part III, Wilson et al., (Eds.) Humana Press, 174: 125-127, 2001.
Fuks et al., "The Methyl-CpG-binding Protein MeCP2 Links DNA Methylation to Histone Methylation," *J. Biol. Chem.*, 278(6):4035-4040, 2003.
Furie and Furie, "The molecular basis of blood coagulation," *Cell*, 53(4):505-518, 1988.

(56) References Cited

OTHER PUBLICATIONS

Gama-Norton et al., "Notch signal strength controls cell fate in the haemogenic endothelium," *Nature Comm.*, 6(8510), 12 pages, 2015.
Gilsbach et al., "Dynamic DNA methylation orchestrates cardiomyocyte development, maturation and disease," *Nature Comm.*, 5(5288): 1-13, 2014.
Golde et al., "Production of erythroid-potentiating activity by a human T-lymphoblast cell line,"*Proc. Natl. Acad. Sci. USA*, 77(1):593-596, 1980.
Gonzalez et al., "Generation of mouse-induced pluripotent stem cells by transient expression of a single nonviral polycistronic vector," *PNAS*, 106(22):8918-8922, 2009.
Gouon-Evans et al., "BMP-4 is required for hepatic specification of mouse embryonic stem cell-derived definitive endoderm," *Nat. Biotechnol.*, 24(11):1402-1411, 2006.
Haddad et al., "Molecular characterization of early human T/NK and B-lymphoid progenitor cells in umbilical cord blood," *Blood*, 104(13):3918-3926, 2004.
Huijskens et al., "Technical Advance: Ascorbic acid induces development of double-positive T cells from human hematopoietic stem cells in the absence of stromal cells," *J. Leukocyte Biol.*, 96:1165-1175, 2014.
Jaenisch, "Transgenic animals," *Science*, 240(4858):1468-1474, 1988.
Kennedy et al., "T Lymphocyte Potential Marks the Emergence of Definitive Hematopoietic Progenitors in Human Pluripotent Stem Cell Differentiation Cultures," *Cell Reports*, 2:1722-1735, 2012.
Kieusseian et al., "Immature hematopoietic stem cells undergo maturation in the fetal liver," *Development*, 139(19):3521-3530, 2012.
Kim et al., "Genomic variation and segregation of equine infectious anemia virus during acute infection" *J. Virol.*, 66(6):3879-3882, 1992.
Kitajima et al., "In vitro generation of HSC-like cells from murine ESCs/iPSCs by enforced expression of LIM-homeobox transcription factor Lhx2," *Blood*, 117(14):3748-3758, 2011.
Knust et al., "EGF homologous sequences encoded in the genome of *Drosophila melanogaster*, and their relation to neurogenic genes," *EMBO J.*, 6(3):761-766, 1987.
Kyba et al., "HoxB4 confers definitive lymphoid-myeloid engraftment potential on embryonic stem cell and yolk sac hematopoietic progenitors," *Cell*, 109(1):29-37, 2002.
Ladi et al., "Thymic microenvironments for T cell differentiation and selection," *Nature Immunology*, 7(4):338-343, 2006.
Langle-Rouault et al., "Up to 100-fold increase of apparent gene expression in the presence of Epstein-Barr virus oriP sequences and EBNA1: implications of the nuclear import of plasmids," *J. Virol.*, 72(7):6181-6185, 1998.
Lappalainen et al. "A protocol for generating high numbers of mature and functional human mast cells from peripheral blood," *Clin. Experim. Allergy*, 37:1404-1414.
Laranjeiro et al., "The Notch Ligand Delta-Like 4 Regulates Multiple Stages of Early Hemato-Vascular Development," *PLoS One*, 7(4):e34553, 1-13, 2012.
Lessard et al., "Comparison of DNA methylation profiles in human fetal and adult red blood cell progenitors," *Genome Med.*, 7(1):1-12, 2015.
Levitskaya et al., "Inhibition of ubiquitin/proteasome-dependent protein degradation by the Gly-Ala repeat domain of the Epstein-Barr Virus nuclear antigen 1," *Proc. Natl. Acad. Sci. USA*, 94(23):12616-12621, 1997.
Li et al., "Epigenetic Control of Circadian Clock Operation during Development," *Genetics Res. Int.*, 845429:1-8, 2012.
Ludwig et al. "Delivation of human embryonic stem cells in defined conditions," *Nature Biotech.*, 24(2):185-187, 2006.
Ludwig et al. "Feeder-independent culture of human embryonic stem cells," *Nature Methods*, 3(8):637-646, 2006.
Lusis et al., "Purification and characterization of a human T-lymphocyte-derived granulocyte-macrophage colony-stimulating factor," *Blood*, 57(1):13-21, 1981.

McIntosh et al., "Nonirradiated NOD,B6.SC1D Il2rγ-/-Kit(W41/W41) (NBSGW) mice support multilineage engraftment of human hematopoietic cells," *Stem Cell Reports*, 4(2):171-180, 2015.
Miskaia and Ryan, "Protein Coexpression using FMDV 2A: Effect of "Linker" Residues," *BioMed Research International*, Article ID 291790, pp. 1-12, 2013.
Nguyen et al., "Global methylation profiling of lymphoblastoid cell lines reveals epigenetic contributions to autism spectrum disorders and a novel autism candidate gene, RORA, whose protein product is reduced in autistic brain," *FASEB J.*, 24:3037-3051, 2010.
Nicola et al., "Separation of functionally distinct human granulocyte-macrophage colony-stimulating factors," *Blood*, 54(3):614-627, 1979.
Nishimura et al., "Generation of rejuvenated antigen-specific T cells by reprogramming to pluripotency and redifferentiation," *Cell Stem Cell*, 12(1):114-126, 2013.
Nostro et al., "Stage-specific signaling through TGFβ family members and WNT regulates patterning and pancreatic specification of human pluripotent stem cells," *Development*, 138:861-871, 2011.
Notta et al., "Isolation of single human hematopoietic stem cells capable of long-term multilineage engraftment," *Science*, 333 (6039):218-221, 2011.
Oberlin et al., "VE-cadherin expression allows identification of a new class of hematopoietic stem cells within human embryonic liver," *Blood*, 116(22):4444-4455, 2010.
Office Communication issued in European Patent Application No. 16778383.4, dated Jun. 25, 2019.
Okabe, "Large-scale preparation and characterization of human colony-stimulating factor," *J. Cell. Phys.*, 110(1):43-49, 1982.
Pandey et al., "A novel MeCP2 acetylation site regulates interaction with ATRX and HDAC1," *Genes Cancer*, 6(9-10):408-421, 2015.
PCT International International Search Report and Written Opinion issued in International Application No. PCT/US2016/057899, dated Feb. 17, 2017.
PCT International Invitation to Pay Additional Fees issued in International Application No. PCT/US2016/057899, dated Dec. 9, 2016.
PCT International Search Report and Written Opinion issued in corresponding PCT Application No. PCT/US2017/055353, dated Jan. 22, 2018.
PCT International Search Report and Written Opinion issued in International Application No. PCT/US2016/057893, dated Dec. 6, 2016.
PCT International Search Report and Written Opinion issued in International Application No. PCT/US2017/055369, dated Feb. 16, 2018.
Pereira et al., "Induction of a Hemogenic Program in Mouse Fibroblasts," *Cell Stem Cell*, 13(2):205-218, 2013.
Pick et al., "Differentiation of human embryonic stem cells in serum-free medium reveals distinct roles for bone morpho genetic protein 4, vascular endothelial growth factor, stem cell factor, and fibroblast growth factor 2 in hematopoiesis," *Stem Cells*, 25(9):2206-2214, 2007.
Ramos-Mejia et al., "HOXA9 promotes hematopoietic commitment of human emnyonic stem cells," *Blood*, 124(20):3065-3075, 2014.
Reubinoff et al., "Embryonic stem cell lines from human blastocysts: somatic differentiation in vitro," *Nat. Biotechnol.*, 18(4):399-404, 2000.
Riddell et al., "Reprogramming committed murine blood cells to induced hematopoietic stem cells with defined factors," *Cell*, 157(3):549-564, 2014.
Sackett et al., "Modulation of human allogeneic and syngeneic pluripotent stem cells and immunological implications for transplantation," *Transplantation Reviews*, 30(2):61-70, 2016.
Salvagiotto et al., "A Defined, Feeder-Free, Serum-Free System to Generate In Vitro Hematopoietic Progenitors and Differentiated Blood Cells from hESCs and hiPSCs,"*PLoS One*, 6(3):e17829, 2011.
Sandler et al., "Reprogramming human endothelial cells to haematopoietic cells requires vascular induction," *Nature*, 511(7509):312-318, 2014.
Schernthaner et al., "Expression, epitope analysis, and functional role of the LFA-2 antigen detectable on neoplastic mast cells," *Blood*, 98:3784-3792, 2001.

(56) References Cited

OTHER PUBLICATIONS

Scicchitano et al., "In Vitro expansion of human cord blood CD36+ erythroid progenitors: Temporal changes in gene and protein expression," *Exp Hematol.*, 31(9):760-769, 2003.
Sharghi-Namini et al., "Dll4-containing exosomes induce capillary sprout retraction in a 3D microenvironment," *Scientific Reports*, 4(4031):1-8, 2014.
Slukvin et al. "Direct differentiation of human embryonic stem cells into functional dendritic cells through the Myeloid Pathway," *The Journal of Immunology*, 176:2924-2932, 2006.
Suzuki et al, "Structure and expression of human thrombomodulin, a thrombin receptor on endothelium acting as a cofactor for protein C activation," *EMBO J.*, 6(7):1891-1897, 1987.
Suzuki et al., "Generation of Engraftable Hematopoietic Stem Cells from Induced Pluripotent Stem Cells by Way of Teratoma Formation," *Mol Ther.*, 21(7):1424-1431, 2013.
Takahashi et al., "Induction of Pluripotent Stem Cells from Mouse Embryonic and Adult Fibroblast Cultures by Defined Factors," *Cell*, 131(5):861-872, 2007.
Takeda et al., "NUP98-HOXA9 induces long-term proliferation and blocks differentiation of primary human CD34+ hematopoietic cells," *Cancer Res*, 66:6628-6637, 2006.
Tanaka et al., "Transcriptional regulation in pluripotent stem cells by methyl CpG-binding protein 2 (MeCPG2)," *Human Mol. Genetics*, 23(4):1045-1055, 2013.
Theisen et al., "Biochemical Analysis of Histone Deacetylase-independent Transcriptional Repression by MeCP2," *J. Biol. Chem.*, 288(10):7096-7104, 2013.
U.S. Appl. No. 61/088,054 entitled "Methods for the Production of IPS Cells" by Amanda Mack et al., filed Aug. 12, 2008.
Vacca et al., "CD34+ hematopoietic precursors are present in human decidua and differentiate into natural killer cells upon interaction with stromal cells," *PNAS*, 108(6):2402-2407, 2011.
Vecsler et al., "MeCP2 deficiency down-regulates specific nuclear proteins that could be partially recovered by valproic acid in vitro," *Epigenetics*, 5(1):61-67, 2010.
Vo et al., "De novo generation of HSCs from somatic and pluripotent stem cell sources," *Blood*, 125(17):2641-2648, 2015.
Wilson et al., "Epigenetic control of T-helper-cell differentiation," *Nature Reviews Immunology*, 9:91-105, 2009.
Wynn, "T(H)-17: a giant step from T(H)1 and T(H)2," *Nature Immunology*, 6:1069-1070, 2005.
Xi et al. "In Vitro Large Scale Production of Human Mature Red Blood Cells from Hematopoietic Stem Cells by Coculturing with Human Fetal Liver Stromal Cells," *Biomed Res. Int.* 2013(807863):1-12, 2013.
Yamanaka et al., "Induction of pluripotent stem cells from adult human fibroblasts by defined factors," *Cell*, 131(5):861-72, 2007.
Ying et al., "Conversion of embryonic stem cells into neuroectodermal precursors in adherent monoculture," 21(2):183-6, 2003.
Yu et al. "Induced Pluripotent Stem Cell Lines Derived from Human Somatic Cells," *Science*, 318(5858):1917-1920, 2007.
Zhang et al., "DNA methylation dynamics duiing ex vivo differentiation and maturation of human dendritic cells," *Epigenetics Chromatin*, 7(21):1-16, 2014.

\* cited by examiner

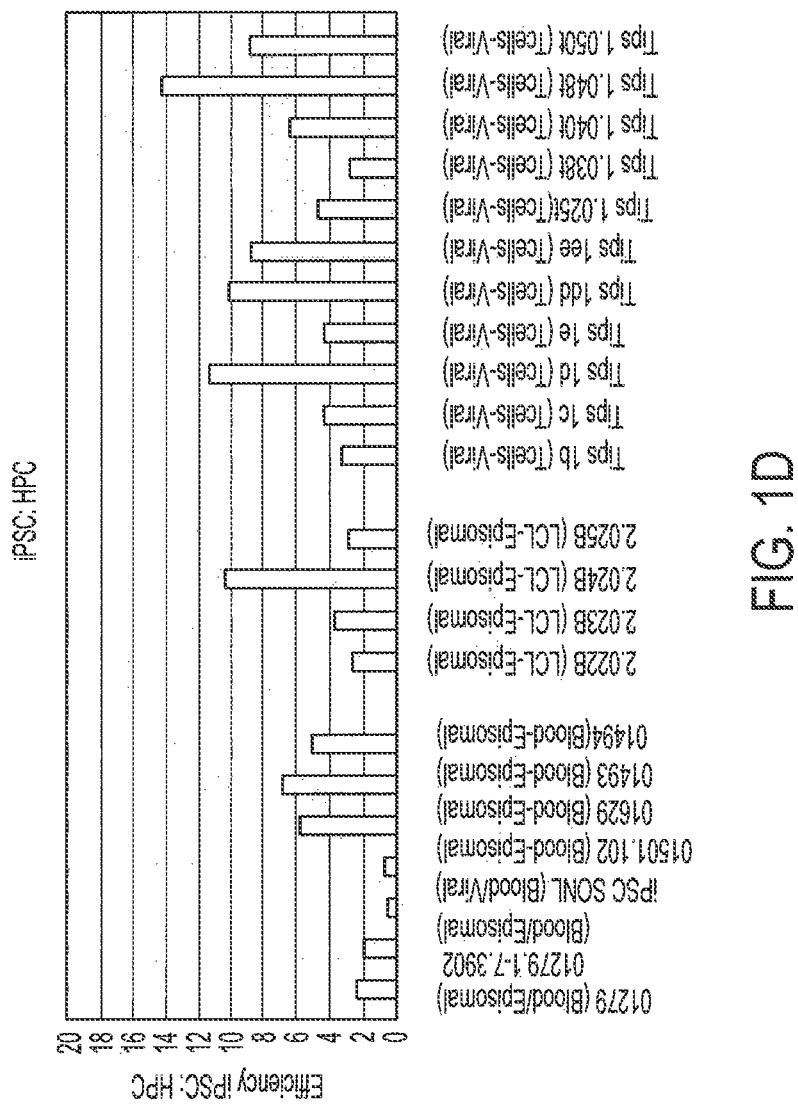

| 3902 | Input:Output CD43/34+ |
|---|---|
| Day 7 | 1 : 0.54 |
| Day 8 | 1 : 1.07 |
| Day 9 | 1 : 1.15 |
| Day 10 | 1 : 3.79 |

| Tips 1e | Input:Output CD43/34+ |
|---|---|
| Day 7 | 1 : 0.84 |
| Day 8 | 1 : 2.51 |
| Day 9 | 1 : 3.13 |
| Day 10 | 1 : 9.38 |

FIG. 16E

| 3902 | Two Weeks Input:HPC:Output CD3+ |
|---|---|
| Day 7 | 1 : 0.11 |
| Day 8 | 1 : 0 |
| Day 9 | 1 : 0 |
| Day 10 | 1 : 0.53 |

| Tips 1e | Input HPC:Output CD3+ |
|---|---|
| Day 7 | 1 : 0.091 |
| Day 8 | 1 : 5.88 |
| Day 9 | 1 : 2.73 |
| Day 10 | 1 : 1.2 |

FIG. 16H

| Methyl CpG | Binding Domain |
| Engineering Site |

```
MECP2_002  MAAAAAAAPSGGGGGGEEERLEEKSEDQDLQGLKDKPLKFKKVKKDKKEEKEGKHEPVQP
MECP2_005  --------------MVAGMLGLREEKSEDQDLQGLKDKPLKFKKVKKDKKEEKEGKHEPVQP
MECP2_001  --------------MVAGMLGLREEKSEDQDLQGLKDKPLKFKKVKKDKKEEKEGKHEPVQP
MECP2_008  --------------MVAGMLGLREEKSEDQDLQGLKDKPLKFKKVKKDKKEEKEGKHEPVQP

MECP2_002  SKXXAHHSAEPAEAGKAETSEGSGSAPAVPEASASPKQRRSIIRDRGPMYDDPTLPEGWTRKL
MECP2_005  SKXXAHHSAEPAEAGKAETSEGSGSAPAVPEASASPKQRRSIIRDRGPMYDDPTLPEGWTRKL
MECP2_001  SKXXAHHSAEPAEAGKAETSEGSGSAPAVPEASASPKQRRSIIRDRGPMYDDPTLPEGWTRKL
MECP2_008  SKXXA-------------------------------------------------------

MECP2_002  KQRKSGRSAGKYDVYLINPQGKAFRSKVELIAYFEKVGDTSLDPNDFDFTVTGRGSPSRR
MECP2_005  KQRKSGRSAGKYDVYLINPQGKAFRSKVELIAYFEKLQELAEAGDAP-E----KGAA---
MECP2_001  KQRKSGRSAGKYDVYLINPQGKAFRSKVELIAYFEKVGDTSLDPNDFDFTVTGRGSPSRR
MECP2_008  ------------------------------------------------------------

MECP2_002  EQKPPKKPKSPKAPGTGRGRGRPKGSGTTRPKAATSEGVQVKRVLEKSPGKLLVKMPFQT
MECP2_005  ----PRDPRRPRQ---RVCR-----------------------------------------
MECP2_001  EQKPPKKPKSPKAPGTGRGRGRPKGSGTTRPKAATSEGVQVKRVLEKSPGKLLVKMPFQT
MECP2_008  ------------------------------------------------------------

MECP2_002  SPGGKAEGGGATTSTQVMVIKRPGRKRKAEADPQAIPKKRGRKPGSVVAAAAAEAKKKAV
MECP2_005  ------------------------------------------------------------
MECP2_001  SPGGKAEGGGATTSTQVMVIKRPGRKRKAEADPQAIPKKRGRKPGSVVAAAAAEAKKKAV
MECP2_008  ------------------------------------------------------------

MECP2_002  KESSIRSVQETVLPIKKRKTRETVSIEVKEVVKPLLVSTLGEKSGKGLKTCKSPGRKSKE
MECP2_005  ------------------------------------------------------------
MECP2_001  KESSIRSVQETVLPIKKRKTRETVSIEVKEVVKPLLVSTLGEKSGKGLKTCKSPGRKSKE
MECP2_008  ------------------------------------------------------------

MECP2_002  SSPKGRSSSASSPPKKEHHHHHHHSESPKAPVPLLPPLPPPPPEPESSEDPTSPPEPQDL
MECP2_005  ------------------------------------------------------------
MECP2_001  SSPKGRSSSASSPPKKEHHHHHHHSESPKAPVPLLPPLPPPPPEPESSEDPTSPPEPQDL
MECP2_008  ------------------------------------------------------------

MECP2_002  SSSVCKEEKMPRGGSLESDGCPKEPAKTQPAVATAATAAEKYKHRGEGERKDIVSSSMPR
MECP2_005  ------------------------------------------------------------
MECP2_001  SSSVCKEEKMPRGGSLESDGCPKEPAKTQPAVATAATAAEKYKHRGEGERKDIVSSSMPR
MECP2_008  ------------------------------------------------------------

MECP2_002  PNREEPVDSRTPVTERVS
MECP2_005  ------------------
MECP2_001  PNREEPVDSRTPVTERVS
MECP2_008  ------------------
```

FIG. 17C

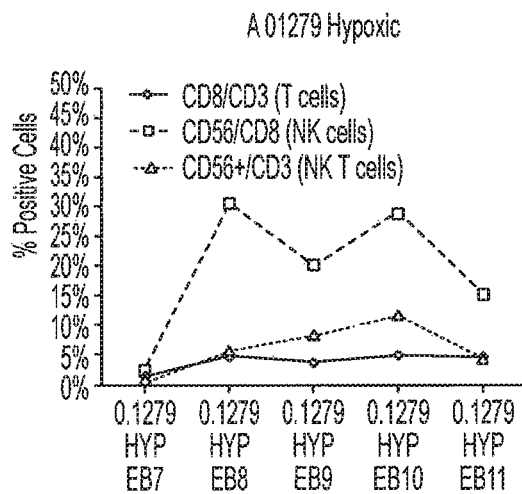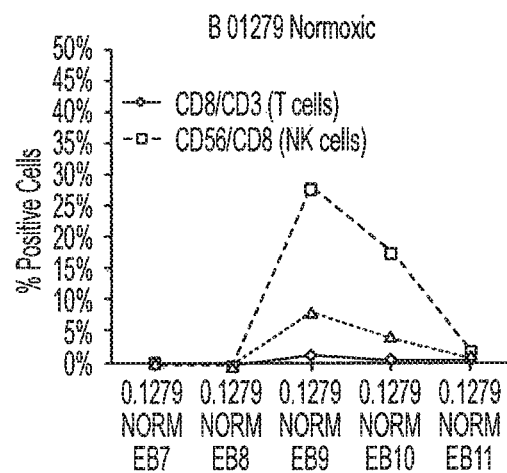
FIG. 18A
FIG. 18B
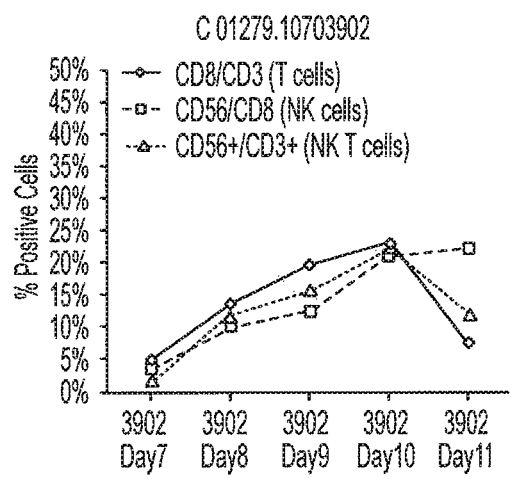
FIG. 18C

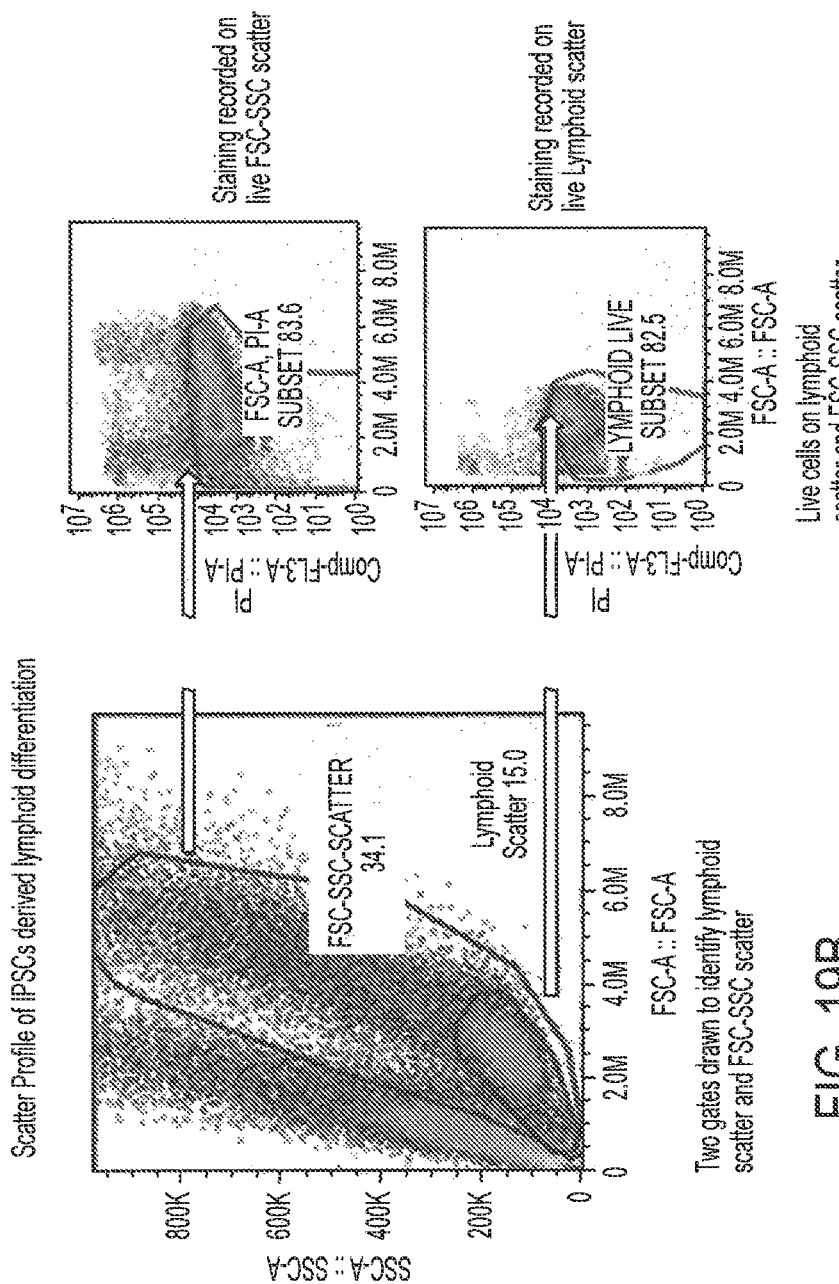

METHODS FOR DIRECTED DIFFERENTIATION OF PLURIPOTENT STEM CELLS TO IMMUNE CELLS

The present application is a national phase application under 35 U.S.C. § 371 of International Application No. PCT/US2016/057899, filed Oct. 20, 2016, which claims the priority benefit of U.S. Provisional Applications Ser. No. 62/244,101, filed Oct. 20, 2015, and Ser. No. 62/404,470, filed Oct. 5, 2016, the entire contents of each of which are hereby incorporated by reference.

BACKGROUND OF THE INVENTION

1. Field of the Invention

The present invention relates generally to the field of molecular biology. More particularly, it concerns methods and compositions for the production of immune cells from somatic cell-derived induced pluripotent stem cells (iPSCs).

2. Description of Related Art

Cell therapy methods have been developed in order to enhance the host immune response to tumors, viruses and bacterial pathogens. Cell therapy methods often involve the ex-vivo activation and expansion of T-cells. Examples of these types of treatments include the use of tumor infiltrating lymphocyte (TIL) cells, cytotoxic T-cells, expanded tumor draining lymph node cells, and various other lymphocyte preparations. Due to the significant medical potential of hematopoietic stem and progenitor cells, substantial work has been done to try to improve methods for the differentiation of hematopoietic progenitor cells to immune cells, such as T cells and NK cells.

In humans, induced pluripotent stem (iPS) cells are commonly generated from dermal fibroblasts. However, the requirement for skin biopsies and the need to expand fibroblast cells for several passages in vitro make it a cumbersome source for generating patient-specific stem cells. Moreover, previous methods for reprogramming of human somatic cells are inconvenient because they need to obtain somatic cells directly from a human subject, or maintain the cells in a labor-intensive cell culture system. Therefore, there is a need to develop methods to induce pluripotent stem cells from alternative sources which are simple, convenient, and easily accessible. Accordingly, blood samples may be such a source because blood may be collected from a patient or a healthy individual, stored or transferred, for example, from a central unit for distribution to one or more remote places. Thus, there currently exists a clear need for methods of reprogramming iPS cells from somatic cells and then efficiently differentiating the somatic cell-derived iPS cells to immune cells, such as T cells, NK cells, T/NK cells, and dendritic cells.

SUMMARY OF THE INVENTION

A first embodiment of the present disclosure provides a method of producing immune cells comprising obtaining pluripotent stem cells (PSCs), wherein the PSCs are reprogrammed from a population of somatic cells, differentiating the PSCs to hematopoietic precursor cells (HPCs), and culturing the HPCs under conditions to promote immune cell differentiation, thereby producing immune cells.

In some aspects, the PSCs are induced pluripotent stem cells (iPSCs). In other aspects, the PSCs are embryonic stem cells (ECSs). In some aspects, the PSCs are essentially free of integrated, exogenous viral elements.

In certain aspects, the immune cells are lymphoid cells. In particular aspects, the lymphoid cells are T cells, B cells, and/or NK cells. In some aspects, the immune cells are myeloid cells. In specific aspects, the myeloid cells are dendritic cells.

In some aspects, the population of somatic cells is mammalian. In particular aspects, the population of somatic cells is human. In some aspects, the population of somatic cells are a population of blood cells or a population of skin cells. In some aspects, the population of blood cells has not been mobilized with extrinsically applied G-CSF. In certain aspects, the population of blood cells comprises T cells, B cells, and/or NK cells. In some aspects, the population of blood cells is further defined as progenitor blood cells, peripheral blood mononuclear cells, or lymphoblastoid cells. In certain aspects, the population of blood cells is isolated from peripheral blood, umbilical cord blood, or lymphoid tissue. In particular aspects, the lymphoid tissue comprises bone marrow, lymph node, or fetal liver. In specific aspects, the population of blood cells comprises T cells. In some aspects, the T cells are cultured in the presence of an anti-CD3 antibody and/or an anti-CD28 antibody. In particular aspects, the T cells are CD4$^+$ or CD8$^+$ T cells. In some aspects, the T cells are T helper 1 (TH1) cells, T helper 2 (TH2) cells, TH17 cells, cytotoxic T cells, regulatory T cells, natural killer T cells, naïve T cells, memory T cells, or gamma delta T cells. In certain aspects, the reprogramming comprises introducing reprogramming factors into the population of somatic cells. In some aspects, reprogramming comprises introducing RNA, protein, or small molecules into the population of somatic cells.

In particular aspects, the population of somatic cells are blood cells or skin cells. In some aspects, the reprogramming factors are encoded by one or more expression cassettes. In certain aspects, the reprogramming factors comprise two or more genes selected from the group consisting of Sox2, Oct4, cMyc, Klf4, Nanog, SV40 Large T antigen, and Lin28. In some aspects, the reprogramming factors comprise 3, 4, 5, or 6 of the genes selected from the group consisting of Sox2, Oct4, cMyc, Klf4, Nanog, SV40 Large T antigen, and Lin28. In certain aspects, the one or more expression cassettes are comprised in a reprogramming vector selected from the group consisting of a viral vector, an episomal vector, and a transposon. In some aspects, the viral vector is further defined as a retroviral vector. In particular aspects, the episomal vector is further defined as an Epstein-Barr virus (EBV)-based episomal vector. In some aspects, the reprogramming comprises culturing the cells under defined, feeder-free conditions.

In some aspects, the HPCs differentiate to at least 20 immune cells per HPC, such as at least 30, 40, 50, 60, 70, 70, 90, 100 or more immune cells per HSC. In some aspects, the PSCs differentiate to at least 20 immune cells per PSC, such as at least 30, 40, 50, or more immune cells per PSC.

In certain aspects, differentiating the PSCs to HPCs comprises the sequential steps of culturing or maintaining a plurality of substantially undifferentiated pluripotent cells in a first defined media comprising at least one growth factor, incubating the cells in a second defined media which is free or essentially free of IL-3, Flt3 ligand, and GM-CSF, culturing the cells in a third defined media comprising BMP4, FGF2, and VEGF sufficient to expand or promote differentiation in a plurality of the cells, and culturing the cells in a fourth defined media comprising IL-3 and Flt3 ligand, sufficient to expand or promote differentiation in a plurality of the cells. In some aspects, a plurality of the pluripotent cells are differentiated into HPCs. In some aspects, the second defined media comprises blebbistatin. In certain aspects, the second defined media further comprises a GSK3 inhibitor. In some aspects, the GSK3 inhibitor is CHIR99021. In some aspects, the second defined media further comprises BMP4, VEGF, and FGF2. In certain aspects, the cells are individualized prior to incubating the cells in the second defined media. In some aspects, incubating the cells in a second defined media, culturing the cells in a third defined media, and culturing the cells in a fourth defined media is performed using amine culture plates. In certain aspects, the second defined media further comprises VEGF and FGF2. In particular aspects, the fourth defined media further comprises one or more of the cytokines selected from the group consisting of IL-3, IL-6, SCF, TPO, and BMP4. In some aspects, the fourth defined media comprises heparin. In some aspects, the method comprises culturing the cells at an atmospheric pressure of less than 25% oxygen, such as less than 24%, 23%, 22%, 21%, 20%, 19%, 18%, 17%, 16%, 15%, 10%, or 5% oxygen. In some aspects, a plurality of the pluripotent cells form embryoid bodies (EBs). In certain aspects, the HPCs express CD34. In particular aspects, the HPCs express at least two markers from the group consisting of CD43, CD34, CD31, CD41, CD235 and CD45.

In some aspects, conditions to promote immune cell differentiation are further defined as conditions to promote lymphoid differentiation. In certain aspects, HPCs that express CD34 and CD43 are cultured under conditions to promote lymphoid differentiation. In some aspects, culturing the cells to promote lymphoid differentiation comprises culturing HPCs in defined media on a surface coated with matrix and a Notch ligand, wherein the HPCs express one or more of the cell surface markers selected from the group consisting of CD34, CD43, CD7, DLL4, CD144, and CD235, and maintaining the culture in the presence of one or more cytokines, thereby producing lymphoid cells. In some aspects, the HPCs express CD144, CD34, CD45, and CD7. In particular aspects, the HPCs express CD144, CD34, CD45, and CD7.

In additional aspects, the first step for lymphoid differentiation further comprises isolating the HPCs that express one or more cell surface markers. In some aspects, isolating comprises magnetic-activated cell sorting (MACS). In certain aspects, the cells are cultured at an atmospheric pressure of less than 5% oxygen. In certain aspects, the cells are cultured at an atmospheric pressure of about 5% oxygen. In some aspects, the defined media comprises ascorbic acid and/or nicotinamide. In certain aspects, the ascorbic acid is present at a concentration of 50 µM to 1 mM, such as 90 µM to 100 µM. In some aspects, the nicotinamide is present at a concentration of 0.1 mM to 5 mM. In some aspects, the nicotinamide is nicotinic acid. In some aspects, the matrix is extracellular matrix protein. In some aspects, the matrix is retronectin, collagen, laminin or fibronectin. In particular aspects, the matrix is retronectin. In some aspects, the Notch ligand is DLL4. In certain aspects, the DLL4 is DLL4:Fc chimera protein. In particular aspects, the one or more cytokines are selected from the group consisting of SCF, TPO, IL-7, and Flt-3. In some aspects, the second step is one to six weeks, such as two to four weeks. In some aspects, the lymphoid cells express one or more of the markers selected from the group consisting of CD8, CD7, CD45, CD5, CD4 and CD3. In some aspects, more than 5% of the lymphoid cells are positive for at least two of the markers. In particular aspects, more than 10% of the lymphoid cells are positive for at least two of the markers.

In some aspects, conditions to promote immune cell differentiation are further defined as conditions to promote myeloid differentiation. In certain aspects, culturing the HPCs under conditions to promote myeloid differentiation comprises culturing the HPCs in a first defined media comprising TPO, SCF, and Flt3 ligand, thereby producing a population of myeloid cells, and incubating the cells in a second defined media essentially free of TPO, SCF, and Flt3 ligand, thereby producing an enriched population of myeloid cells. In some aspects, the first defined media further comprises IL-6 and IL-3. In certain aspects, the second defined media comprises GM-CSF. In particular aspects, at least 50% of the population of myeloid cells produced in the first step are positive for CD45, CD43, and CD31. In some aspects, the population of myeloid cells positive for CD45, CD43, and CD31 has essentially no expression of CD34. In particular aspects, at least 80% of the enriched population of myeloid cells is $CD43^+$, $CD45^+$, $CD31^+$, and $CD34^-$. In some aspects, the second step is for 5 to 10 days.

In certain aspects, the method further comprises differentiating the enriched population of myeloid cells to dendritic cells. In some aspects, differentiating the enriched population of myeloid cells to dendritic cells comprises culturing the enriched population of myeloid cells in a defined media comprising GM-CSF, IL-4, and TNFα, thereby producing dendritic cells. In some aspects, the defined media further comprises lipoproteins. In certain aspects, the dendritic cells express one or more of the markers selected from the group consisting of CD209, CD1a, HLA-DR, CD11c, CD14, CD83, and CD86. In particular aspects, the dendritic cells have essentially no expression of CD12.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-1D: (A) Schematic of feeder free method to derive T, NK, and NK/T cells from iPSCs. The iPSCs are differentiated to HPCs with lymphoid and myeloid potential by the 3D process and the Day 7-10 progenitors are then subjected to a 2D differentiation process to generate T, NK, and NK/T cells (B) Schematic of feeder free method to derive dendritic cells from iPSCs. The iPSCs are differentiated to HPCs with lymphoid and myeloid potential by the 3D process and the Day 12 progenitors are further differentiated to generate a myeloid progenitor and subjected to a step wise 3D differentiation process to generate dendritic cells (C) HPCs were generated from various blood cell-derived iPSC cell lines at day 12 of differentiation and the percentage of $CD43^+/CD34^+$ cells quantified by flow cytometry is shown. (D) The efficiency of HPCs generation from Day 12 iPSCs is shown as the ratio of the absolute number of HPCs generated per input number of iPSCs.

FIGS. 16A-16H: (A) Representative photograph of day 8 HPC cultures: The HPCs bud off from the underlying endothelial layer. (B) Schematic representation of the 2D HPC differentiation process. (C) Generation of HPCs from 01279.107.3902 (MeCP2 KO) cell line at days 7-10 of differentiation. (D) Generation of HPCs from TiPSCs1E cell line at days 7-10 of differentiation. The cells were harvested and the percentage of CD43/CD34 cells was quantified by flow cytometry. (E) Efficiency of generation of HPCs from iPSCs. The efficiency of the process is calculated by dividing the absolute number of HPCs generated per input number of iPSCs. (F) Analysis of Pre T and Pre NK cells. HPCs generated from iPSC 0.1279.107.3902 (MeCP2 KO) were harvested on days 7-10 and cryopreserved. HPCs were thawed and plated at a density of 25K/cm² on Retronectin-DLL4 coated plates. The cells were placed in Serum Free Defined (SFD) media containing 1% Glutamax, 1% Penicillin Streptomycin, 95 µM L-ascorbic acid 2-phosphate, 50 ng/mL stem cell factor (SCF), thrombopoietin (TPO), Flt-3 Ligand (Flt-3), and IL-7 to stimulate lymphoid differentiation under hypoxic and conditions. The cells were fed with fresh media every 48 hrs and harvested on day 14 using cold PBS. The cells were stained for the surface expression of CD4, CD7, CD5, CD56, CD8, and CD3. The percentage of cells were quantified by flow cytometry under lymphoid scatter gate. The presence of T, NK and NK/T cells were quantified. (G) Analysis of Pre T and Pre NK cells. The cells were stained for the surface expression of CD4, CD7, CD5, CD56, CD8, and CD3. The percentage of cells were quantified by flow cytometry under lymphoid scatter gate. (H) Efficiency of generation of T cells from HPCs. The efficiency of the process is calculated by dividing the absolute number of T cells (CD3+) generated per input number of HPCs (CD43/34+).

FIGS. 17A-17C: (A) Schematic representation of 3D HPC differentiation process using iPSCs adapted to feeder free growth on Matrigel or Vitronectin in the presence of E8 media and hypoxic conditions. The first stage of HPC differentiation is driven by BMP4, VEGF and FGF for 4 days and the second stage of differentiation is driven by placing cells in media containing Heparin, SCF, TPO, Flt-3 Ligand, IL-3 and IL-6. (B) Engineering strategy to generate a MeCP2 KO in male iPSC cell line 2.038 to create 9006 (01279.107.003902). (C) Depiction of the amino acid alignment of MeCP2 variants 001, 002, 005 and 008 derived from 01279 iPSCs transfected with MeCP2 TALENS and Donor plasmid p1553. All variants (001, 002, 005 and 008) do not code for a MethylCpG binding domain.

FIGS. 18A-18C: Quantification of Pre T and Pre NK cells iPSC Tips 1E harvested on day 7-11 of HPC differentiation and placed on Ret-DLL4 coated plates to initiate lymphoid differentiation at a density of 2.5×10⁴/cm². The percentages of CD8+CD3+(T cells), CD56+/CD8+(NK cells), and CD56+/CD3+(NK/T cells) in 01279 (MeCP2WT) cells maintained under hypoxic conditions (A) and normoxic conditions (B) as well as 01279.107.3902 cells (MeCP2K0) (C) was determined. (A-B) TheNK cells have the highest percentage of positive cells, followed by NK/T cells, and T cells. (C) From Day 7 to Day 10, the percentage of positive cells from top to bottom are T cells, NK/T cells, and NK cells. At Day 11, the highest percentage of positive cells are NK cells followed by NK/T cells and T cells.

FIGS. 19A-19C: Gating strategy for identifying lymphoid cells generated in vitro. (A) General scatter profile of lymphocytes from adult human peripheral blood. (B) Scatter profile of lymphoid cells at day 18 of differentiation. The FSC-SSC gate and the lymphoid gate are illustrated. (C) Gating live cells within the FSC-SSC scatter and lymphoid scatter using propidium iodide.

DESCRIPTION OF ILLUSTRATIVE EMBODIMENTS

Figure 1A:
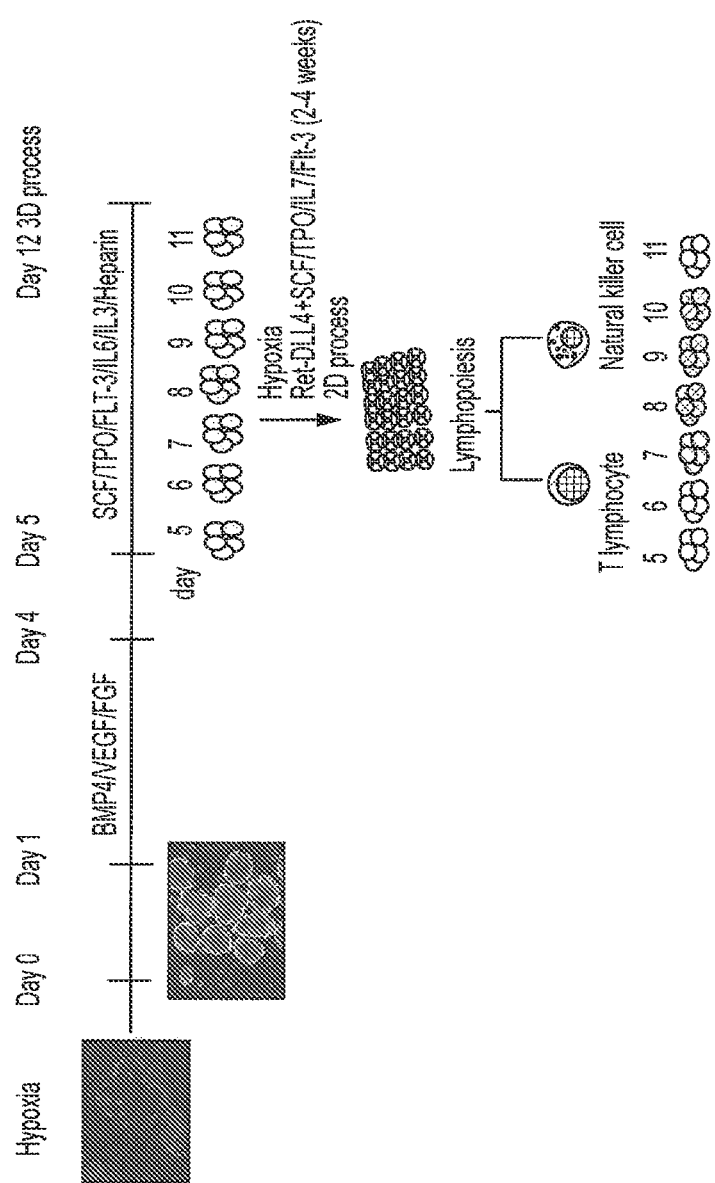

The present disclosure overcomes problems associated with current technologies by providing highly efficient methods for generating immune cells from induced pluripotent stem cells which have been reprogrammed from a starting population of somatic cells (e.g., blood cells). The immune cells produced by the current methods can include T cells, NK cells, T/NK cells, and dendritic cells. In some aspects, the starting population of somatic cells comprises T cells. The T cells may be isolated from various sources, such as a blood sample.

The population of somatic cells is reprogrammed to iPSCs by the introduction of reprogramming factors, such as through a viral or episomal vector. These somatic-cell derived iPSCs (e.g., T-cell derived iPSCs (TiPSCs)) are then differentiated to hematopoietic precursor cells. In one method, the differentiation process involves WNT activation, culture with hematopoetic inductive cytokines and CD34+ cell isolation. Finally, the HPCs are then differentiated to immune cells, such as lymphoid cells (e.g., T, NK, and T/NK cells) and myeloid cells (e.g., dendritic cells).

The differentiation to lymphoid cells may be through the use of RetroNectin and DLL-4 as a feeder free matrix. The T cell differentiation may be further enhanced by the use of ascorbic acid to increase the efficiency and maturation as well as by culturing under hypoxic conditions. Interestingly, the inventors have determined an optimal timeframe during HPC differentiation (e.g., day 7-11) for lymphoid potential. These HPCs with lymphoid potential may be identified by expression of CD34 and CD43. In addition, HPCs with enhanced lymphoid potential may be isolated by sorting for fractions of cells positive for two or more of the markers CD144, CD34, CD45, and CD7. In some aspects, the progenitor for derivation of dendritic cells is a common myeloid progenitor that emerges at around day 16 of HPC differentiation.

The lymphoid cells produced from the somatic cell-derived PSCs can include T cell, NK cells and T/NK cells which retain their characteristic T-cell receptor (TCR) gene rearrangements, a property which could be exploited, for example, as a genetic tracking marker or in re-differentiation experiments to study human T-cell development. A particular advantage of the present disclosure lies in rearranged and reduced V, D, J gene segments of T-cell receptors which may be retained in the differentiated T cells. This serves as a specific characteristic or "barcode" of different clonal populations of T cell-derived iPS cells, and also help differentiates those iPS cells from pluripotent stem cells which have not undergone V(D)J recombination.

Thus, the methods of the present disclosure could provide unlimited numbers of immune cells, such as T cells, NK cells, T/NK cells, and dendritic cells, for a wide range of applications such as stable transplantation in vivo, screening of compounds in vitro, and elucidating the mechanisms of hematological diseases and injuries.

I. Definitions

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

The term "exogenous," when used in relation to a protein, gene, nucleic acid, or polynucleotide in a cell or organism refers to a protein, gene, nucleic acid, or polynucleotide that has been introduced into the cell or organism by artificial or natural means; or in relation to a cell, the term refers to a cell that was isolated and subsequently introduced to other cells or to an organism by artificial or natural means. An exogenous nucleic acid may be from a different organism or cell, or it may be one or more additional copies of a nucleic acid that occurs naturally within the organism or cell. An exogenous cell may be from a different organism, or it may be from the same organism. By way of a non-limiting example, an exogenous nucleic acid is one that is in a chromosomal location different from where it would be in natural cells, or is otherwise flanked by a different nucleic acid sequence than that found in nature.

By "expression construct" or "expression cassette" is meant a nucleic acid molecule that is capable of directing transcription. An expression construct includes, at a minimum, one or more transcriptional control elements (such as promoters, enhancers or a structure functionally equivalent thereof) that direct gene expression in one or more desired cell types, tissues or organs. Additional elements, such as a transcription termination signal, may also be included.

A "vector" or "construct" (sometimes referred to as a gene delivery system or gene transfer "vehicle") refers to a macromolecule or complex of molecules comprising a polynucleotide to be delivered to a host cell, either in vitro or in vivo.

A "plasmid," a common type of a vector, is an extrachromosomal DNA molecule separate from the chromosomal DNA that is capable of replicating independently of the chromosomal DNA. In certain cases, it is circular and double-stranded.

An "origin of replication" ("ori") or "replication origin" is a DNA sequence, e.g., in a lymphotrophic herpes virus, that when present in a plasmid in a cell is capable of maintaining linked sequences in the plasmid and/or a site at or near where DNA synthesis initiates. As an example, an ori for EBV (Ebstein-Barr virus) includes FR sequences (20 imperfect copies of a 30 bp repeat), and preferably DS sequences; however, other sites in EBV bind EBNA-1, e.g., Rep* sequences can substitute for DS as an origin of replication (Kirshmaier and Sugden, 1998). Thus, a replication origin of EBV includes FR, DS or Rep* sequences or any functionally equivalent sequences through nucleic acid modifications or synthetic combination derived therefrom. For example, the present disclosure may also use genetically engineered replication origin of EBV, such as by insertion or mutation of individual elements, as specifically described in Lindner et al., 2008.

A "gene," "polynucleotide," "coding region," "sequence," "segment," "fragment," or "transgene" that "encodes" a particular protein, is a nucleic acid molecule that is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites (IRES), enhancers, splice junctions, and the like, which collectively provide for the replication, transcription, post-transcriptional processing, and translation of a coding sequence in a recipient cell. Not all of these control elements need be present so long as the selected coding sequence is capable of being replicated, transcribed, and translated in an appropriate host cell.

The term "promoter" is used herein in its ordinary sense to refer to a nucleotide region comprising a DNA regulatory sequence, wherein the regulatory sequence is derived from a gene that is capable of binding RNA polymerase and initiating transcription of a downstream (3' direction) coding sequence. It may contain genetic elements at which regulatory proteins and molecules may bind, such as RNA polymerase and other transcription factors, to initiate the specific transcription of a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

By "enhancer" is meant a nucleic acid sequence that, when positioned proximate to a promoter, confers increased transcription activity relative to the transcription activity resulting from the promoter in the absence of the enhancer domain.

By "operably linked" or co-expressed" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" or "co-expressed" with reference to peptide and/or polypeptide molecules means that two or more peptide and/or polypeptide molecules are connected in such a way as to yield a single polypeptide chain, i.e., a fusion polypeptide, having at least one property of each peptide and/or polypeptide component of the fusion. The fusion polypeptide is preferably chimeric, i.e., composed of heterologous molecules.

"Homology" refers to the percent of identity between two polynucleotides or two polypeptides. The correspondence between one sequence and another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions that promote the formation of stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

The term "cell" is herein used in its broadest sense in the art and refers to a living body that is a structural unit of tissue of a multicellular organism, is surrounded by a membrane structure that isolates it from the outside, has the capability of self-replicating, and has genetic information and a mechanism for expressing it. Cells used herein may be naturally-occurring cells or artificially modified cells (e.g., fusion cells, genetically modified cells, etc.).

The term "stem cell" refers herein to a cell that under suitable conditions is capable of differentiating into a diverse range of specialized cell types, while under other suitable conditions is capable of self-renewing and remaining in an essentially undifferentiated pluripotent state. The term "stem cell" also encompasses a pluripotent cell, multipotent cell, precursor cell and progenitor cell. Exemplary human stem cells can be obtained from hematopoietic or mesenchymal stem cells obtained from bone marrow tissue, embryonic stem cells obtained from embryonic tissue, or embryonic germ cells obtained from genital tissue of a fetus. Exemplary pluripotent stem cells can also be produced from somatic cells by reprogramming them to a pluripotent state by the expression of certain transcription factors associated with pluripotency; these cells are called "induced pluripotent stem cells" or "iPSCs or iPS cells".

An "embryonic stem (ES) cell" is an undifferentiated pluripotent cell which is obtained from an embryo in an early stage, such as the inner cell mass at the blastocyst stage, or produced by artificial means (e.g. nuclear transfer) and can give rise to any differentiated cell type in an embryo or an adult, including germ cells (e.g. sperm and eggs).

"Induced pluripotent stem cells (iPSCs or iPS cells)" are cells generated by reprogramming a somatic cell by expressing or inducing expression of a combination of factors (herein referred to as reprogramming factors). iPS cells can be generated using fetal, postnatal, newborn, juvenile, or adult somatic cells. In certain embodiments, factors that can be used to reprogram somatic cells to pluripotent stem cells include, for example, Oct4 (sometimes referred to as Oct 3/4), Sox2, c-Myc, Klf4, Nanog, and Lin28. In some embodiments, somatic cells are reprogrammed by expressing at least two reprogramming factors, at least three reprogramming factors, at least four reprogramming factors, at least five reprogramming factors, at least six reprogramming factors, or at least seven reprogramming factors to reprogram a somatic cell to a pluripotent stem cell.

"Hematopoietic progenitor cells" or "hematopoietic precursor cells" refers to cells which are committed to a hematopoietic lineage but are capable of further hematopoietic differentiation and include hematopoietic stem cells, multipotential hematopoietic stem cells, common myeloid progenitors, megakaryocyte progenitors, erythrocyte progenitors, and lymphoid progenitors. Hematopoietic stem cells (HSCs) are multipotent stem cells that give rise to all the blood cell types including myeloid (monocytes and macrophages, granulocytes (neutrophils, basophils, eosinophils, and mast cells), erythrocytes, megakaryocytes/platelets, dendritic cells), and lymphoid lineages (T-cells, B-cells, NK-cells) (see e.g., Doulatov et al., 2012; Notta et al., 2015). A "multilymphoid progenitor" (MLP) is defined to describe any progenitor that gives rise to all lymphoid lineages (B, T, and NK cells), but that may or may not have other (myeloid) potentials (Doulatov et al., 2010) and is $CD45RA^+/CD10^+/CD7^-$. Any B, T, and NK progenitor can be referred to as an MLP. A "common myeloid progenitor" (CMP) refers to a common myeloid progenitor is defined by the expression of $CD45+/CD31+/CD43+/CD34^-$ cells that can give rise to granulocytes, monocytes, megakaryocytes and erythrocytes. The hematopoietic progenitor cells may express CD34. The hematopoietic progenitor cells may co-express CD133 and be negative for CD38 expression. Hematopoietic precursor cells include $CD34^+/CD45^+$ hematopoietic precursor cells and $CD34^+/CD45^+/CD43^+$ hematopoietic precursor cells. The $CD34^+/CD43^+/CD45+$ hematopoietic precursor cells may be highly enriched for myeloid progenitors. Hematopoietic cells also include various subsets of primitive hematopoietic cells including: $CD34^-/CD133^+/CD38^-$ (primitive hematopoietic precursor cells), CD43(+)CD235a (+)CD41a(+/−) (erythro-megakaryopoietic), lin(−)CD34(+) CD43(+)CD45(−) (multipotent), and lin(−) CD34(+)CD43 (+)CD45(+) (myeloid-skewed) cells, CD133+/ALDH+ (aldehydehehydrogenase) (e.g., Hess et al. 2004; Christ et al., 2007). It is anticipated that any of these primitive hematopoietic cell types or hematopoietic precursor cells may be converted into iPS cells as described herein. In some aspects, the cells may include Mast cells, Langerhan's cells, Osteoclasts, NK cells, T cells, CIK T cells, or other subtypes of T cells, NK cells, and B cells.

As used herein, the term "immune cell(s)" refers to cells of the immune system, including, but not limited to, T cells, NK cells, T/NK cells, dendritic cells, macrophages, B cells, neutrophils, erythrocytes, monocytes, basophils, neutrophils, mast cells, eosinphils, and any combination thereof.

An "activator" of a T cell or a condition that will activate a T cell refers to a stimulus that activates T cells and include antigens, which may be presented on antigen presenting cells or on other surfaces; polyclonal activators, which bind to many T cell receptor (TCR) complexes regardless of specificity, and include lectins, e.g., concanavalin-A (Con-A) and phytohemagglutinin (PHA) and agents such as antibodies that bind specifically to invariant framework epitopes on TCR or CD3 proteins; and superantigens, which stimulate a significant number of T cells, and include, e.g., enterotoxins, such as Staphyloccal enterotoxins.

The terms "T lymphocyte" and "T cell" are used interchangeably, and refer to a cell that expresses a T cell antigen receptor (TCR) capable of recognizing antigen when displayed on the surface of antigen presenting cells or matrix together with one or more MHC molecules or, one or more non-classical MHC molecules.

The term "T cell" refers to T lymphocytes as defined in the art and is intended to include thymocytes, immature T lymphocytes, mature T lymphocytes, resting T lymphocytes, or activated T lymphocytes. The T cells can be $CD4^+$ T cells, $CD8^+$ T cells, $CD4^+CD8^+$ T cells, or $CD4^-CD8^-$ cells. The T cells can also be T helper cells, such as T helper 1 (TH1), or T helper 2 (TH2) cells, or TH17 cells, as well as cytotoxic T cells, regulatory T cells, natural killer T cells, naïve T cells, memory T cells, or gamma delta T cells (Wilson et al., 2009; Wynn, 2005; Ladi et al., 2006). T cells that differ from each other by at least one marker, such as CD4, are referred to herein as "subsets" of T cells.

"$CD4^+$ T cells" refers to a subset of T cells that express CD4 on their surface and are associated with cell-mediated immune response. They are characterized by the secretion profiles following stimulation, which may include secretion of cytokines such as IFN-gamma, TNF-alpha, IL-2, IL-4 and IL-10. "CD4" are 55-kD glycoproteins originally defined as differentiation antigens on T-lymphocytes, but also found on other cells including monocytes/macrophages. CD4 antigens are members of the immunoglobulin supergene family and are implicated as associative recognition elements in MHC (major histocompatibility complex) class II-restricted immune responses. On T-lymphocytes they define the helper/inducer subset.

"$CD8^+$ T cells" refers to a subset of T cells which express CD8 on their surface, are MHC class I-restricted, and function as cytotoxic T cells. "CD8" molecules are differentiation antigens found on thymocytes and on cytotoxic and suppressor T-lymphocytes. CD8 antigens are members of the immunoglobulin supergene family and are associative recognition elements in major histocompatibility complex class I-restricted interactions.

"Pluripotent stem cell" refers to a stem cell that has the potential to differentiate into all cells constituting one or more tissues or organs, or preferably, any of the three germ layers: endoderm (interior stomach lining, gastrointestinal tract, the lungs), mesoderm (muscle, bone, blood, urogenital), or ectoderm (epidermal tissues and nervous system).

As used herein, the term "somatic cell" refers to any cell other than germ cells, such as an egg, a sperm, or the like, which does not directly transfer its DNA to the next generation. Typically, somatic cells have limited or no pluripotency. Somatic cells used herein may be naturally-occurring or genetically modified.

"Programming" is a process that alters the type of progeny a cell can produce. For example, a cell has been programmed when it has been altered so that it can form progeny of at least one new cell type, either in culture or in vivo, as compared to what it would have been able to form under the same conditions without programming. This means that after sufficient proliferation, a measurable proportion of progeny having phenotypic characteristics of the new cell type are observed, if essentially no such progeny could form before programming; alternatively, the proportion having characteristics of the new cell type is measurably more than before programming. This process includes differentiation, dedifferentiation and transdifferentiation.

"Differentiation" is the process by which a less specialized cell becomes a more specialized cell type. "Dedifferentiation" is a cellular process in which a partially or terminally differentiated cell reverts to an earlier developmental stage, such as pluripotency or multipotency. "Transdifferentiation" is a process of transforming one differentiated cell type into another differentiated cell type. Typically, transdifferentiation by programming occurs without the cells passing through an intermediate pluripotency stage—i.e., the cells are programmed directly from one differentiated cell type to another differentiated cell type. Under certain conditions, the proportion of progeny with characteristics of the new cell type may be at least about 1%, 5%, 25% or more in order of increasing preference.

"Reprogramming" is a process that confers on a cell a measurably increased capacity to form progeny of at least one new cell type, either in culture or in vivo, than it would have under the same conditions without reprogramming. More specifically, reprogramming is a process that confers on a somatic cell a pluripotent potential. This means that after sufficient proliferation, a measurable proportion of progeny having phenotypic characteristics of the new cell type if essentially no such progeny could form before reprogramming; otherwise, the proportion having characteristics of the new cell type is measurably more than before reprogramming. Under certain conditions, the proportion of progeny with characteristics of the new cell type may be at least about 1%, 5%, 25% or more in order of increasing preference.

The term "forward programming" refers to the programming of a multipotent or pluripotent cell, as opposed to a differentiated somatic cell that has no pluripotency, by the provision of one or more specific lineage-determining genes or gene products to the multipotent or pluripotent cell. For example, forward programming may describe the process of programming ESCs or iPSCs to hematopoietic precursor cells or other precursor cells, or to hematopoietic cells or other differentiated somatic cells.

As used herein, the term "subject" or "subject in need thereof" refers to a mammal, preferably a human being, male or female at any age that is in need of a cell or tissue transplantation. Typically the subject is in need of cell or tissue transplantation (also referred to herein as recipient) due to a disorder or a pathological or undesired condition, state, or syndrome, or a physical, morphological or physiological abnormality which is amenable to treatment via cell or tissue transplantation.

As used herein, a "disruption" of a gene refers to the elimination or reduction of expression of one or more gene products encoded by the subject gene in a cell, compared to the level of expression of the gene product in the absence of the disruption. Exemplary gene products include mRNA and protein products encoded by the gene. Disruption in some cases is transient or reversible and in other cases is permanent. Disruption in some cases is of a functional or full length protein or mRNA, despite the fact that a truncated or non-functional product may be produced. In some embodiments herein, gene activity or function, as opposed to expression, is disrupted. Gene disruption is generally induced by artificial methods, i.e., by addition or introduction of a compound, molecule, complex, or composition, and/or by disruption of nucleic acid of or associated with the gene, such as at the DNA level. Exemplary methods for gene disruption include gene silencing, knockdown, knockout, and/or gene disruption techniques, such as gene editing. Examples include antisense technology, such as RNAi, siRNA, shRNA, and/or ribozymes, which generally result in transient reduction of expression, as well as gene editing techniques which result in targeted gene inactivation or disruption, e.g., by induction of breaks and/or homologous recombination. Examples include insertions, mutations, and deletions. The disruptions typically result in the repression and/or complete absence of expression of a normal or "wild type" product encoded by the gene. Exemplary of such gene disruptions are insertions, frameshift and missense mutations, deletions, knock-in, and knock-out of the gene or part of the gene, including deletions of the entire gene. Such disruptions can occur in the coding region, e.g., in one or more exons, resulting in the inability to produce a full-length product, functional product, or any product, such as by insertion of a stop codon. Such disruptions may also occur by disruptions in the promoter or enhancer or other region affecting activation of transcription, so as to prevent transcription of the gene. Gene disruptions include gene targeting, including targeted gene inactivation by homologous recombination.

"Notch ligand" is a protein capable of binding to a Notch receptor polypeptide present in the membrane of a number of different mammalian cells such as hematopoietic stem cells. The Notch receptors that have been identified in human cells include Notch-1, Notch-2, Notch-3, and Notch-4. Notch ligands typically have a DSL domain (D-Delta, S-Serrate, and L-Lag2) comprising 20 to 22 amino acids at the amino terminus and between 3 to 8 EGF-like repeats (Furie and Furie, 1988; Knust et al., 1987; Suzuki et al., 1987) on the extracellular surface.

II. Somatic Cell-Derived iPSCs

A. Starting Population of Somatic Cells

Embodiments of the present disclosure concern a starting population of somatic cells (e.g., blood cells or skin cells) which are reprogrammed to iPSCs. The population of blood cells can include peripheral blood mononuclear cells (PBMC), whole blood or fractions thereof containing mixed populations, spleen cells, bone marrow cells, tumor infiltrating lymphocytes, cells obtained by leukapheresis, biopsy tissue, and lymph nodes, e.g., lymph nodes draining from a tumor. Suitable donors include immunized donors, non-immunized (naive) donors, treated or untreated donors. A "treated" donor is one that has been exposed to one or more biological modifiers. An "untreated" donor has not been exposed to one or more biological modifiers.

In some aspects, the population of blood cells comprises T cells. The T cells can be a purified population of T cells, or alternatively the T cells can be in a population with cells of a different type, such as B cells and/or other peripheral blood cells. The T cells can be a purified population of a subset of T cells, such as $CD4^+$ T cells, or they can be a population of T cells comprising different subsets of T cells. In another embodiment, the T cells are T cell clones that have been maintained in culture for extended periods of time. T cell clones can be transformed to different degrees. In a specific embodiment, the T cells are a T cell clone that proliferates indefinitely in culture.

In some aspects, the T cells are primary T cells. The term "primary T cells" is intended to include T cells obtained from an individual, as opposed to T cells that have been maintained in culture for extended periods of time. Thus, primary T cells are particularly peripheral blood T cells obtained from a subject. A population of primary T cells can be composed of mostly one subset of T cells. Alternatively, the population of primary T cells can be composed of different subsets of T cells.

The T cells can be from previously stored blood samples, from a healthy individual, or alternatively from an individual affected with a condition. The condition can be an infectious disease, such as a condition resulting from a viral infection, a bacterial infection or an infection by any other microorganism, or a hyperproliferative disease, such as cancer like melanoma. In a specific embodiment, the T cells are from an individual infected with a human immunodeficiency virus (HIV). In yet another embodiment, the T cells are from a subject suffering from or susceptible to an autoimmune disease or T-cell pathologies. The T cells can be of human origin, murine origin or any other mammalian species.

Methods of obtaining populations of cells comprising T cells are well known in the art. For example, peripheral blood mononuclear cells (PBMC) can be obtained as described according to methods known in the art. Examples of such methods are set forth in the Examples and is discussed by Kim et al. (1992); Biswas et al. (1990); Biswas et al. (1991).

In some aspects, the starting population of blood cells comprises hematopoietic stem cells (HSCs). HSCs normally reside in the bone marrow but can be forced into the blood, a process termed mobilization used clinically to harvest large numbers of HSCs in peripheral blood. One mobilizing agent of choice is granulocyte colony-stimulating factor (G-CSF). $CD34^+$ hematopoietic stem cells or progenitors that circulate in the peripheral blood can be collected by apheresis techniques either in the unperturbed state, or after mobilization following the external administration of hematopoietic growth factors like G-CSF. The number of the stem or progenitor cells collected following mobilization is greater than that obtained after apheresis in the unperturbed state. In some aspects, the source of the cell population is a subject whose cells have not been mobilized by extrinsically applied factors because there is no need to enrich hematopoietic stem cells or progenitor cells.

Methods of obtaining hematopoietic precursor cells from populations of cells are also well known in the art. Hematopoietic precursor cells may be expanded using various cytokines, such as hSCF, hFLT3, and/or IL-3 (Akkina et al., 1996), or $CD34^+$ cells may be enriched using MACS or FACS. As mentioned above, negative selection techniques may also be used to enrich $CD34^+$ cells.

Populations of cells for use in the methods described herein may be mammalian cells, such as human cells, non-human primate cells, rodent cells (e.g., mouse or rat), bovine cells, ovine cells, porcine cells, equine cells, sheep cells, canine cells, and feline cells or a mixture thereof. Non-human primate cells include rhesus macaque cells. The cells may be obtained from an animal, e.g., a human patient, or they may be from cell lines. If the cells are obtained from an animal, they may be used as such, e.g., as unseparated cells (i.e., a mixed population); they may have been established in culture first, e.g., by transformation; or they may have been subjected to preliminary purification methods. For example, a cell population may be manipulated by positive or negative selection based on expression of cell surface markers; stimulated with one or more antigens in vitro or in vivo; treated with one or more biological modifiers in vitro or in vivo; or a combination of any or all of these. In an illustrative embodiment, a cell population is subjected to negative selection for depletion of non-T cells and/or particular T cell subsets. Negative selection can be performed on the basis of cell surface expression of a variety of molecules, including B cell markers such as CD19, and CD20; monocyte marker CD14; the NK cell marker CD56. Alternately, a cell population may be subjected to negative selection for depletion of non-$CD34^+$ hematopoietic cells and/or particular hematopoietic cell subsets. Negative selection can be performed on the basis of cell surface expression of a variety of molecules, such as a cocktail of antibodies (e.g., CD2, CD3, CD11b, CD14, CD15, CD16, CD19, CD56, CD123, CD235a, and CD41 (e.g., for cells of megakaryocyte lineage) which may be used for separation of other cell types, e.g., via MACS or column separation.

It is also possible to obtain a cell sample from a subject, and then to enrich it for a desired cell type. For example, PBMCs and/or CD34+ hematopoietic cells can be isolated from blood as described herein. Counter-flow centrifugation (elutriation) can be used to enrich for T cells from PBMCs. Cells can also be isolated from other cells using a variety of techniques, such as isolation and/or activation with an antibody binding to an epitope on the cell surface of the desired cell type, for example, some T-cell isolation kits use antibody conjugated beads to both activate the cells and then allow column separation with the same beads. Another method that can be used includes negative selection using antibodies to cell surface markers to selectively enrich for a specific cell type without activating the cell by receptor engagement.

Bone marrow cells may be obtained from iliac crest, femora, tibiae, spine, rib or other medullary spaces. Bone marrow may be taken out of the patient and isolated through various separations and washing procedures. A known procedure for isolation of bone marrow cells comprises the following steps: a) centrifugal separation of bone marrow suspension in three fractions and collecting the intermediate fraction, or buffycoat; b) the buffycoat fraction from step (a) is centrifuged one more time in a separation fluid, commonly Ficoll (a trademark of Pharmacia Fine Chemicals AB), and an intermediate fraction which contains the bone marrow cells is collected; and c) washing of the collected fraction from step (b) for recovery of re-transfusable bone marrow cells.

If one desires to use a population of cells enriched in T cells, such populations of cells can be obtained from a mixed population of cells by leukapheresis and mechanical apheresis using a continuous flow cell separator. For example, T cells can be isolated from the buffy coat by any known method, including separation over Ficoll-Hypaque™ gradient, separation over a Percoll gradient, or elutriation.

In certain aspects, T cells are activated by agents that bind to T cell receptors to trigger a signaling cascade for T cell activation. For example, a CD3 antibody may be used. For T cell expansion to a significant number and a proliferating state for reprogramming, a cytokine may also be used, such as IL-2. In a certain aspect, both anti-CD3 and anti-CD28 may be used for T cell activation where co-stimulation is involved. In an alternative aspect, cross-linking of the anti-CD3 may be applied, such as plate bound anti-CD3. If soluble anti-CD3 is used to activate T cells in PBMC, the soluble anti-CD3 antibody may bind to APCs in the PBMC, which then presents the antibody to the T cells. If the soluble anti-CD3 antibody alone is used in a population of purified T-cells, anergy would result for the reasons mentioned above. A certain embodiment comprises culturing T cells in the presence of the anti-CD3 (OKT3) and IL2, which is advantageous and convenient because there is no need to use costly and cumbersome beads or plate-bound antibody; after adding OKT3 and IL2, the cellular milieu of PBMCs would help activate the T cells. The T cells then overcrowd the other cell types in the PBMC culture due to preferential expansion.

In certain aspects, the starting population of blood cells comprises lymphoblastoid cells, such as from lymphoblastoid cells lines (LCLs). Generation of LCLs is known in the art, for example, by infection of B cells with Epstein-Barr virus (EBV) (Frisan et al., Epstein-Barr Virus Protocols, Part III, 125-127, 2001).

B. Reprogramming Factors

In certain embodiments, the starting population of somatic cells is reprogrammed to iPS cells by the introduction of reprogramming factors. The generation of iPS cells is crucial on the reprogramming factors used for the induction. The following factors or combination thereof could be used in the methods disclosed in the present disclosure. In certain aspects, nucleic acids encoding Sox and Oct (particularly Oct3/4) will be included into the reprogramming vector. For example, one or more reprogramming vectors may comprise expression cassettes encoding Sox2, Oct4, Nanog and optionally Lin28, or expression cassettes encoding Sox2, Oct4, Klf4 and optionally c-Myc, or expression cassettes encoding Sox2, Oct4, and optionally Esrrb, or expression cassettes encoding Sox2, Oct4, Nanog, Lin28, Klf4, c-Myc, and optionally SV40 Large T antigen. Nucleic acids encoding these reprogramming factors may be comprised in the same expression cassette, different expression cassettes, the same reprogramming vector, or different reprogramming vectors.

Oct4 and certain members of the Sox gene family (Sox1, Sox2, Sox3, and Sox15) have been identified as crucial transcriptional regulators involved in the induction process whose absence makes induction impossible. Additional genes, however, including certain members of the Klf family (Klf1, Klf2, Klf4, and Klf5), the Myc family (c-Myc, L-Myc, and N-Myc), Nanog, and Lin28, have been identified to increase the induction efficiency.

Oct4 (Pou5f1) is one of the family of octamer ("Oct") transcription factors, and plays a crucial role in maintaining pluripotency. The absence of Oct4 in Oct4+ cells, such as blastomeres and embryonic stem cells, leads to spontaneous trophoblast differentiation, and presence of Oct4 thus gives rise to the pluripotency and differentiation potential of embryonic stem cells. Various other genes in the "Oct" family, including Oct4's close relatives, Oct1 and Oct6, fail to elicit induction, thus demonstrating the exclusiveness of Oct-4 to the induction process.

The Sox family of genes is associated with maintaining pluripotency similar to Oct4, although it is associated with multipotent and unipotent stem cells in contrast with Oct4, which is exclusively expressed in pluripotent stem cells. While Sox2 was the initial gene used for reprogramming induction, other genes in the Sox family have been found to work as well in the induction process. Sox1 yields iPS cells with a similar efficiency as Sox2, and genes Sox3, Sox15, and Sox18 also generate iPS cells, although with decreased efficiency.

In embryonic stem cells, Nanog, along with Oct4 and Sox2, is necessary in promoting pluripotency. Therefore, it was surprising when Yamanaka et al. reported that Nanog was unnecessary for induction although Thomson et al. has reported it is possible to generate iPS cells with Nanog as one of the factors.

Lin28 is an mRNA binding protein expressed in embryonic stem cells and embryonic carcinoma cells associated with differentiation and proliferation. Thomson et al. demonstrated it is a factor in iPS generation, although it is unnecessary.

Klf4 of the Klf family of genes was initially identified by Yamanaka et al., 2007 and confirmed by Jaenisch et al., 1988 as a factor for the generation of mouse iPS cells and was demonstrated by Yamanaka et al., 2007 as a factor for generation of human iPS cells. However, Thompson et al. reported that Klf4 was unnecessary for generation of human iPS cells and in fact failed to generate human iPS cells. Klf2 and Klf4 were found to be factors capable of generating iPS cells, and related genes Klf1 and Klf5 did as well, although with reduced efficiency.

The Myc family of genes are proto-oncogenes implicated in cancer. Yamanaka et al., 2007 and Jaenisch et al., 1988 demonstrated that c-Myc is a factor implicated in the generation of mouse iPS cells and Yamanaka et al., 2007 demonstrated it was a factor implicated in the generation of human iPS cells. However, Thomson et al. and Yamanaka et al. reported that c-Myc was unnecessary for generation of human iPS cells. SV40 large antigen may be used to reduce or prevent the cytotoxcity which may occur when c-Myc is expressed.

The reprogramming proteins used in the present disclosure can be substituted by protein homologs with about the same reprogramming functions. Nucleic acids encoding those homologs could also be used for reprogramming. Conservative amino acid substitutions are preferred—that is, for example, aspartic-glutamic as polar acidic amino acids; lysine/arginine/histidine as polar basic amino acids; leucine/isoleucine/methionine/valine/alanine/glycine/proline as non-polar or hydrophobic amino acids; serine/threonine as polar or uncharged hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting polypeptide. Whether an amino acid change results in a functional polypeptide can readily be determined by assaying the specific activity of the polypeptide.

C. Reprogramming of Somatic Cells

In certain aspects of the present disclosure, reprogramming factors are expressed from expression cassettes comprised in one or more vectors, such as an integrating vector or an episomal vector. In a further aspect, reprogramming proteins could be introduced directly into somatic cells by protein transduction.

One of skill in the art would be well-equipped to construct a vector through standard recombinant techniques (see, for example, Sambrook et al., 2001 and Ausubel et al., 1996, both incorporated herein by reference). Vectors include but are not limited to, plasmids, cosmids, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus vectors, herpes virus vectors, vaccinia virus vectors, Harvey murine sarcoma virus vectors, murine mammary tumor virus vectors, Rous sarcoma virus vectors.

1. Viral Vectors

Viral vectors may be provided in certain aspects of the present disclosure. In generating recombinant viral vectors, non-essential genes are typically replaced with a gene or coding sequence for a heterologous (or non-native) protein. A viral vector is a kind of expression construct that utilizes viral sequences to introduce nucleic acid and possibly proteins into a cell. The ability of certain viruses to infect cells or enter cells via receptor-mediated endocytosis, and to integrate into host cell genomes and express viral genes stably and efficiently have made them attractive candidates for the transfer of foreign nucleic acids into cells (e.g., mammalian cells). Non-limiting examples of virus vectors that may be used to deliver a nucleic acid of certain aspects of the present disclosure are described below.

Retroviruses have promise as gene delivery vectors due to their ability to integrate their genes into the host genome, transfer a large amount of foreign genetic material, infect a broad spectrum of species and cell types, and be packaged in special cell-lines (Miller, 1992).

In order to construct a retroviral vector, a nucleic acid is inserted into the viral genome in place of certain viral sequences to produce a virus that is replication-defective. In order to produce virions, a packaging cell line containing the gag, pol, and env genes—but without the LTR and packaging components—is constructed (Mann et al., 1983). When a recombinant plasmid containing a cDNA, together with the retroviral LTR and packaging sequences, is introduced into a special cell line (e.g., by calcium phosphate precipitation), the packaging sequence allows the RNA transcript of the recombinant plasmid to be packaged into viral particles, which are then secreted into the culture medium (Nicolas and Rubenstein, 1988; Temin, 1986; Mann et al., 1983). The medium containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136).

Recombinant lentiviral vectors are capable of infecting non-dividing cells and can be used for both in vivo and ex vivo gene transfer and expression of nucleic acid sequences. For example, recombinant lentivirus capable of infecting a non-dividing cell—wherein a suitable host cell is transfected with two or more vectors carrying the packaging functions, namely gag, pol and env, as well as rev and tat—is described in U.S. Pat. No. 5,994,136, incorporated herein by reference.

2. Episomal Vectors

The use of plasmid- or liposome-based extra-chromosomal (i.e., episomal) vectors may be also provided in certain aspects of the present disclosure. Such episomal vectors may include, e.g., oriP-based vectors, and/or vectors encoding a derivative of EBNA-1. These vectors may permit large fragments of DNA to be introduced unto a cell and maintained extra-chromosomally, replicated once per cell cycle, partitioned to daughter cells efficiently, and elicit substantially no immune response.

In particular, EBNA-1, the only viral protein required for the replication of the oriP-based expression vector, does not elicit a cellular immune response because it has developed an efficient mechanism to bypass the processing required for presentation of its antigens on MHC class I molecules (Levitskaya et al., 1997). Further, EBNA-1 can act in trans to enhance expression of the cloned gene, inducing expression of a cloned gene up to 100-fold in some cell lines (Langle-Rouault et al., 1998; Evans et al., 1997). Finally, the manufacture of such oriP-based expression vectors is inexpensive.

Other extra-chromosomal vectors include other lymphotrophic herpes virus-based vectors. Lymphotrophic herpes virus is a herpes virus that replicates in a lymphoblast (e.g., a human B lymphoblast) and becomes a plasmid for a part of its natural life-cycle. Herpes simplex virus (HSV) is not a "lymphotrophic" herpes virus. Exemplary lymphotrophic herpes viruses include, but are not limited to EBV, Kaposi's sarcoma herpes virus (KSHV); Herpes virus saimiri (HS) and Marek's disease virus (MDV). Other sources of episome-base vectors are also contemplated, such as yeast ARS, adenovirus, SV40, or BPV.

One of skill in the art would be well-equipped to construct a vector through standard recombinant techniques (see, for example, Maniatis et al., 1988 and Ausubel et al., 1994, both incorporated herein by reference).

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide.

Such components also may include markers, such as detectable and/or selection markers that can be used to detect or select for cells that have taken up and are expressing the nucleic acid delivered by the vector. Such components can be provided as a natural feature of the vector (such as the use of certain viral vectors that have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

3. Transposon-based System

In certain aspects, the delivery of programming factors can use a transposon-transposase system. For example, the transposon-transposase system could be the well known Sleeping Beauty, the Frog Prince transposon-transposase system (for a description of the latter, see, e.g., EP1507865), or the TTAA-specific transposon PiggyBac system.

Transposons are sequences of DNA that can move around to different positions within the genome of a single cell, a process called transposition. In the process, they can cause mutations and change the amount of DNA in the genome. Transposons were also once called jumping genes, and are examples of mobile genetic elements.

There are a variety of mobile genetic elements, and they can be grouped based on their mechanism of transposition. Class I mobile genetic elements, or retrotransposons, copy themselves by first being transcribed to RNA, then reverse transcribed back to DNA by reverse transcriptase, and then being inserted at another position in the genome. Class II mobile genetic elements move directly from one position to another using a transposase to "cut and paste" them within the genome.

In particular embodiments, the constructs (e.g., the multilineage construct) provided in the present disclosure use a PiggyBac expression system. PiggyBac (PB) DNA transposons mobilize via a "cut-and-paste" mechanism whereby a transposase enzyme (PB transposase), encoded by the transposon itself, excises and re-integrates the transposon at other sites within the genome. PB transposase specifically recognizes PB inverted terminal repeats (ITRs) that flank the transposon; it binds to these sequences and catalyzes excision of the transposon. PB then integrates at TTAA sites throughout the genome, in a relatively random fashion. For the creation of gene trap mutations (or adapted for generating transgenic animals), the transposase is supplied in trans on one plasmid and is co-transfected with a plasmid containing donor transposon, a recombinant transposon comprising a gene trap flanked by the binding sites for the transposase (ITRs). The transposase will catalyze the excision of the transposon from the plasmid and subsequent integration into the genome. Integration within a coding region will capture the elements necessary for gene trap expression. PB possesses several ideal properties: (1) it preferentially inserts within genes (50 to 67% of insertions hit genes) (2) it exhibits no local hopping (widespread genomic coverage) (3) it is not sensitive to over-production inhibition in which elevated levels of the transposase cause decreased transposition 4) it excises cleanly from a donor site, leaving no "footprint," unlike Sleeping Beauty.

4. Regulatory Elements

Expression cassettes included in reprogramming vectors useful in the present disclosure preferably contain (in a 5'-to-3' direction) a eukaryotic transcriptional promoter operably linked to a protein-coding sequence, splice signals including intervening sequences, and a transcriptional termination/polyadenylation sequence.

a. Promoter/Enhancers

The expression constructs provided herein comprise promoter to drive expression of the programming genes. A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e. g., beta actin promoter (Ng, 1989; Quitsche et al., 1989), GADPH promoter (Alexander et al., 1988, Ercolani et al., 1988), metallothionein promoter (Karin et al., 1989; Richards et al., 1984); and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at Genbank, accession no. X05244, nucleotide 283-341) or a mouse mammary tumor promoter (available from the ATCC, Cat. No. ATCC 45007).

Tissue-specific transgene expression, especially for reporter gene expression in hematopoietic cells and precursors of hematopoietic cells derived from programming, may be desirable as a way to identify derived hematopoietic cells and precursors. To increase both specificity and activity, the use of cis-acting regulatory elements has been contemplated. For example, a hematopoietic cell-specific promoter may be used. Many such hematopoietic cell-specific promoters are known in the art, such as promoters of the hematopoietic genes provided in Table 1.

In certain aspects, methods of the present disclosure also concern enhancer sequences, i.e., nucleic acid sequences that increase a promoter's activity and that have the potential to act in cis, and regardless of their orientation, even over relatively long distances (up to several kilobases away from the target promoter). However, enhancer function is not necessarily restricted to such long distances as they may also function in close proximity to a given promoter.

Many hematopoietic cell promoter and enhancer sequences have been identified, and may be useful in present methods. See, e.g., U.S. Pat. No. 5,556,954; U.S. Patent App. 20020055144; U.S. Patent App. 20090148425.

b. Initiation Signals and Linked Expression

A specific initiation signal also may be used in the expression constructs provided in the present disclosure for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

Additionally, certain 2A sequence elements could be used to create linked- or co-expression of programming genes in the constructs provided in the present disclosure. For example, cleavage sequences could be used to co-express genes by linking open reading frames to form a single cistron. An exemplary cleavage sequence is the F2A (Foot-and-mouth disease virus 2A) or a "2A-like" sequence (e.g., Thosea asigna virus 2A; T2A) (Minskaia and Ryan, 2013).

In particular embodiments, an F2A-cleavage peptide is used to link expression of the genes in the multi-lineage construct.

c. Origins of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in programming, which is a specific nucleic acid sequence at which replication is initiated. Alternatively a replication origin of other extra-chromosomally replicating virus as described above or an autonomously replicating sequence (ARS) can be employed.

d. Selection and Screenable Markers

In certain embodiments, cells containing a nucleic acid construct may be identified in vitro or in vivo by including a marker in the expression vector. Such markers would confer an identifiable change to the cell permitting easy identification of cells containing the expression vector. Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art.

Introduction of a nucleic acid, such as DNA or RNA, into the pluripotent stem cells to be programmed to hematopoietic precursor cells with the current disclosure may use any suitable methods for nucleic acid delivery for transformation of a cell, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

III. Production of Immune Cells

A. Production of HPCs

Embodiments of the present disclosure concern the differentiation of somatic cell-derived PSCs to HPCs. The somatic cell-derived PSCs can be differentiated into HPCs by methods known in the art such as described in U.S. Pat. No. 8,372,642, which is incorporated by reference herein. For example, combinations of BMP4, VEGF, Flt3 ligand, IL-3, and GM-CSF may be used to promote hematopoietic differentiation. In certain embodiments, the sequential exposure of cell cultures to a first media to prepare PSCs for differentiation, a second media that includes BMP4, VEGF, and FGF, followed by culture in a third media that includes Flt3 ligand, SCF, TPO, IL-3, and IL-6 can differentiate pluripotent cells into hematopoietic precursor cells and hematopoietic cells. The second defined media can also comprise heparin. Further, inclusion of FGF-2 (50 ng/ml) in the media containing BMP4 and VEGF can enhance the efficiency of the generation of hematopoietic precursor cells from pluripotent cells. In addition, inclusion of a Glycogen synthase kinase 3 (GSK3) inhibitor (e.g., CHIR99021, BIO, and SB-216763) in the first defined media can further enhance the production of HPCs.

Differentiation of pluripotent cells into hematopoietic precursor cells may be performed using defined or undefined conditions. Generally, it will be appreciated that defined conditions are generally preferable in embodiments where the resulting cells are intended to be administered to a human subject. Hematopoietic stem cells may be derived from pluripotent stem cells under defined conditions (e.g., using a TeSR media), and hematopoietic cells may be generated from embryoid bodies derived from pluripotent cells. In other embodiments, pluripotent cells may be co-cultured on OP9 cells or mouse embryonic fibroblast cells and subsequently differentiated.

Pluripotent cells may be allowed to form embryoid bodies or aggregates as a part of the differentiation process. The formation of "embryoid bodies" (EBs), or clusters of growing cells, in order to induce differentiation generally involves in vitro aggregation of human pluripotent stem cells into EBs and allows for the spontaneous and random differentiation of human pluripotent stem cells into multiple tissue types that represent endoderm, ectoderm, and mesoderm origins. Three-dimensional EBs can thus be used to produce some fraction of hematopoietic cells and endothelial cells.

EBs may be formed using the following protocol. Undifferentiated iPSCs adapted to feeder free growth on Matrigel™ coated plates may be harvested at confluency using 0.5M EDTA treatment for about 8-10 minutes at room temperature. The EDTA is aspirated after the incubation and the EBs may be formed by collecting the cells in SFD media containing rock inhibitor or blebbistatin. The media may be changed the next day to EB1 differentiation media containing different cytokine formulations. The cells are plated at a density of 0.25-0.5 million cells per ml to promote aggregate formation.

To promote aggregate formation, the cells may be transferred to low-attachment plates for an overnight incubation in serum-free differentiation (SFD) medium, consisting of 75% IMDM (Gibco), 25% Ham's Modified F12 (Cellgro) supplemented with 0.05% N2 and B-27 without RA supplements, 200 mM l-glutamine, 0.05 mg/ml Ascorbic Acid-2-phosphate Magnesium Salt (Asc 2-P) (WAKO), and $4.5 \times 10^{-4}$ MTG. The next day the cells may be collected from each well and centrifuged. The cells may then be resuspended in "EB differentiation media," which consists of SFD basal media supplemented with about 50 ng/ml bone morphogenetic factor (BMP-4), about 50 ng/ml vascular endothelial growth factor (VEGF), and 50 ng/ml zb FGF for the first four days of differentiation. The cells are half fed ever 48 hrs. On the fifth day of differentiation the media is replaced with a second media comprised of SFD media supplemented with 50 ng/ml stem cell factor (SCF), about 50 ng/ml Flt-3 ligand (Flt-3L), 50 ng/ml interleukin-6 (IL-6), 50 ng/ml interleukin-3 (IL-3), 50 ng/ml thrombopoieitin (TPO). The cells are half fed every 48 hrs with fresh differentiation media. The media changes are performed by spinning down the differentiation cultures at 300 g for 5 minutes and aspirating half the volume from the differentiating cultures and replenishing it with fresh media. In certain embodiments, the EB differentiation media may include about BMP4 (e.g., about 50 ng/ml), VEGF (e.g., about 50 ng/ml), and optionally FGF-2 (e.g., about 25-75 ng/ml or about 50 ng/ml). The supernatant may be aspirated and replaced with fresh differentiation medium. Alternately the cells may be half fed every two days with fresh media. The cells may be harvested at different time points during the differentiation process.

Hematopoietic precursor cells may be cultured from pluripotent stem cells using a defined medium. Methods for the differentiation of pluripotent cells into hematopoietic $CD34^+$ stem cells using a defined media are described, e.g., in U.S. application Ser. No. 12/715,136 which is incorporated by reference in its entirety without disclaimer. It is anticipated that these methods may be used with the present disclosure.

For example, a defined medium may be used to induce hematopoietic $CD34^+$ differentiation. The defined medium may contain the growth factors BMP-4, VEGF, Flt3 ligand, IL-3 and/or GMCSF. Pluripotent cells may be cultured in a first defined media comprising BMP4, VEGF, and optionally FGF-2, followed by culture in a second media comprising either (Flt3 ligand, IL-3, and GMCSF) or (Flt3 ligand, IL-3, IL-6, and TPO). The first and second media may also comprise one or more of SCF, IL-6, G-CSF, EPO, FGF-2, and/or TPO. Substantially hypoxic conditions (e.g., less than 20% 02) may further promote hematopoietic or endothelial differentiation.

Cells may be substantially individualized via mechanical or enzymatic means (e.g., using a trypsin or TrypLE™). A ROCK inhibitor (e.g., H1152 or Y-27632) may also be included in the media. It is anticipated that these approaches may be automated using, e.g., robotic automation.

In certain embodiments, substantially hypoxic conditions may be used to promote differentiation of pluripotent cells into hematopoietic progenitor cells. As would be recognized by one of skill in the art, an atmospheric oxygen content of less than about 20.8% would be considered hypoxic. Human cells in culture can grow in atmospheric conditions having reduced oxygen content as compared to ambient air. This relative hypoxia may be achieved by decreasing the atmospheric oxygen exposed to the culture media. Embryonic cells typically develop in vivo under reduced oxygen conditions, generally between about 1% and about 6% atmospheric oxygen, with carbon dioxide at ambient levels. Without wishing to be bound by theory, it is anticipated that hypoxic conditions may mimic an aspect of certain embryonic developmental conditions. As shown in the below examples, hypoxic conditions can be used in certain embodiments to promote additional differentiation of pluripotent cells, such as iPSC or hESC, into a more differentiated cell type, such as hematopoietic precursor cells.

The following hypoxic conditions may be used to promote differentiation of pluripotent cells into hematopoietic progenitor cells. In certain embodiments, an atmospheric oxygen content of less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, about 5%, about 4%, about 3%, about 2%, or about 1% may be used to promote differentiation into hematopoietic precursor cells. In certain embodiments, the hypoxic atmosphere comprises about 5% oxygen gas.

Regardless of the specific medium being used in any given hematopoietic progenitor cell expansion, the medium used is preferably supplemented with at least one cytokine at a concentration from about 0.1 ng/mL to about 500 ng mL, more usually 10 ng/mL to 100 ng/mL. Suitable cytokines, include but are not limited to, c-kit ligand (KL) (also called steel factor (StI), mast cell growth factor (MGF), and stem cell factor (SCF)), IL-6, G-CSF, IL-3, GM-CSF, IL-1α, IL-11 MIP-1α, LIF, c-mpl ligand/TPO, and flk2/flk3 ligand (Flt2L or Flt3L). (Nicola et al., 1979; Golde et al., 1980; Lusis, 1981; Abboud et al., 1981; Okabe, 1982; Fauser et al., 1981). Particularly, the culture will include at least one of SCF, Flt3L and TPO. More particularly, the culture will include SCF, Flt3L and TPO.

In one embodiment, the cytokines are contained in the media and replenished by media perfusion. Alternatively, when using a bioreactor system, the cytokines may be added separately, without media perfusion, as a concentrated solution through separate inlet ports. When cytokines are added without perfusion, they will typically be added as a 10× to 100× solution in an amount equal to one-tenth to 1/100 of the volume in the bioreactors with fresh cytokines being added approximately every 2 to 4 days. Further, fresh concentrated cytokines also can be added separately in addition, to cytokines in the perfused media.

In some embodiments, the HPCs exhibit disrupted Methyl-CpG Binding Protein 2 (MeCP2) and are cultured under conditions to promote myeloid differentiation or lymphoid differentiation. In some aspects, the HPCs express a non-functional MeCP2 that has essentially no binding to methylated DNA. In certain aspects, the HPCs do not express MeCP2 at levels that are sufficient to effect MeCP2 DNA binding activity. In particular aspects, the MeCP2 is non-functional by virtue of a truncation or mutation in the MeCP2 gene. In some aspects, obtaining HPCs that exhibit disrupted MeCP2 comprises contacting the HPCs with siRNA, shRNA or a small molecule inhibitor of MeCP2.

B. Lymphoid Cell Differentiation

The HPCs which are differentiated from the somatic cell-derived PSCs can then be further differentiated to lymphoid lineage cells, including T cells, NK cells, and T/NK cells. In some aspects, HPCs during differentiation are isolated at Day 7-12, such as Day 8-11, for differentiation to lymphoid cells. The HPCs at this stage may be identified by expression of CD34 and CD43. In addition the HPCs with lymphoid potential can express CD144, DLL4, CD7 and CD235 at low levels which decline at Day 11, implying that a certain threshold level of expression of these markers is needed to prime cells towards lymphoid differentiation in the presence of DLL4.

In some aspects, HPCs isolated at day 7-11, such as day 7, day 8, day 9, day 10 or day 11 of the differentiation process can be differentiated to lymphoid cells such as T and NK cells. In some aspects, the timing of the origin for lymphoid progenitors coincides with the decline of hematoendothelial progenitors and the emergence of erythroid progenitors during HPC differentiation. In particular aspects, Day 9 HPCs may have an increased efficiency at generating T cells. HPCs capable of lymphoid differentiation can be isolated and/or identified by the expression of certain markers. For example, cells with surface expression of CD34 and/or CD43 may be selected for lymphoid differentiation. Additional markers for detecting lymphoid progenitors include DLL4, CD144, CD31, CD34, CD43$^{lo}$, CD45$^{lo/-}$, CD235, CD7, Flk-1, APNLR. In particular aspects, the presence of CD34/CD7, CD235/CD7, DLL4/CD34, DLL4/CD31, DLL4/CD144, or CD34/CD43$^{lo}$ double positive populations is used to identify lymphoid progenitors. CD144 expression on HPCs co stains with CD31, CD34 and DLL4. CD7 expression on HPCs co-stains with CD235, CD34 and CD43. Hence HPCs co-expressing CD144 and CD7 demonstrate lymphoid potential capture precursors expressing membrane bound notch ligand (DLL4) along with hematoendothelial markers and create the phenotypic signature for emerging lymphoid progenitors capable of generating lineages of definitive hematopoiesis in vitro. In particular aspects, the HPCs may be further sorted into cells with enhanced lymphoid potential by sorting of the surface markers including CD31, CD34, CD144, CD43, CD45, CD6, CD335, Flk-1, and DLL4. In some aspects, the positive fractions of CD114/CD34, CD144/CD45, CD144/CD7, and CD144/CD34/CD45/CD7 of HPCs are differentiated to lymphoid cells. In particular aspects, the CD144/CD7 positive fractions of HPCs is differentiated to lymphoid cells.

The HPCs may be cultured in defined, feeder free conditions for lymphoid differentiation. A culture media may contain one or more matrix components, such as RetroNectin, fibronectin or a RGD peptide. Without wishing to be bound by any theory, a matrix component may provide a solid support for the growth of embryonic stem cells. In certain embodiments, a matrix component may be applied to a culturing surface and contacted with culture media prior to seeding cells into the media. For example, cells may be cultured in a defined media (e.g., a TeSR media) on plates coated with fibronectin or Matrigel™ prior to mechanically separating the cells into clumps or individualizing cells and inducing differentiation into hematopoietic precursor cells.

Various matrix components may be used to culture pluripotent cells including a collagen (e.g., collagen IV), laminin, vitronectin, Matrigel™, gelatin, polylysine, thrombospondin (e.g., TSP-1, -2, -3, -4 and/or -5), and/or ProNectin-F™. In certain embodiments, the use of only Matrigel™, collagen IV, or laminin with cells previously cultured using TeSR may be avoided due to possible adverse effects on cell viability; nonetheless, these compositions may be advantageously used in combination with other matrix components. Combinations of these matrix components may provide additional benefit for promoting cell growth and cell viability. In certain embodiments, 1, 2, 3, 4, 5, 6, or more of the above matrix components may be used to culture cells, e.g., prior to hematopoietic differentiation.

An exemplary feeder free matrix for lymphoid differentiation is disclosed in Example 4. In particular aspects, a nontissue culture-treated plate may be coated with DLL4:Fc chimera protein and RetroNectin (fibronectin fragment CH-296; Takara Shuzo, Japan) for use in lymphoid differentiation of HPCs.

In some embodiments, ascorbic acid may be used to enhance lymphoid differentiation. The defined media may be supplemented with about 10 µM to about 1 mM ascorbic acid, such as about 50 µM to about 100 µM, such as about 95 µM. The ascorbic acid may be selected from various ascorbates, such as ascorbic acid magnesium phosphate. In some embodiments, nicotinamide (e.g., nicotinic acid) may be used to enhance lymphoid differentiation, such as at a concentration of about 0.1 mM to about 5 mM.

In some aspects, the HPCs are differentiated to lymphoid cells, such as T cells, by altering the endogenous activity of a Notch ligand by administering a substance that increases the production of the Notch ligand in a subject. The method also includes culturing the cells in a medium, wherein the medium includes an effective amount of a notch ligand and one or more cytokines selected from the group consisting of IL-7, IL-15, SCF, Flt-3 and IL-3. In some particular embodiments, the medium can further include IL-6. In some embodiments, the notch ligand is delta4 notch ligand (DLL4), such as DLL4:Fc chimera.

A Notch ligand is selected that promotes and maintains differentiation and proliferation of cells of the T cell lineage. A Notch ligand may be human in origin, or may be derived from other species, including mammalian species such as rodent, dog, cat, pig, sheep, cow, goat, and primates. Particular examples of Notch Ligands include the Delta family. The Delta family includes Delta-1 (Genbank Accession No. AF003522, *Homo sapiens*), Delta-3 (Genbank Accession No. AF084576, *Rattus norvegicus*), Delta-like 1 (Genbank Accession No. NM_005618 and NP_005609, *Homo sapiens*; Genbank Accession No. X80903, 148324, *M. musculus*), Delta-like 3 (Genbank Accession No. NM_053666, N_446118, *Rattus norvegicus*), Delta-4 (Genbank Accession No. AF273454, BAB18580, *Mus musculus*; Genbank Accession No. AF279305, AAF81912, *Homo sapiens*), and Delta-like 4 (Genbank Accession. No. Q9NR61, AAF76427, AF253468, NM_019074, *Homo sapiens*; Genbank Accession No. NM_019454, *mus musculus*). Notch ligands are commercially available or can be produced by recombinant DNA techniques and purified to various degrees.

The method further includes the step of maintaining the HPC cells in the culture described above for a duration of time sufficient to produce differentiated NK cells. In some embodiments, differentiated NK cells emerge in the cultures along with T cells, however the NK cells may cease to proliferate after week 6. In general, the determination of an increase in the number of NK cells and/or their state of differentiation is assessed using conventional methods known to those of ordinary skill in the art. For example, the cultured cells may be monitored by flow cytometry for the development of NK cells by staining the cells with anti-CD56 and anti-CD3 antibodies. Cells which are CD56$^+$/CD3$^-$ would be indicative of differentiated NK cells.

C. Myeloid Differentiation

HPCs produced from somatic cell-derived PSCs may be differentiated into myeloid cells using, e.g., a myeloid differentiation medium. A myeloid differentiation medium may be a serum-free or defined medium, and the medium may contain SCF, EPO, TPO, insulin, dexamethasone or hydrocortisone, and/or transferrin. The myeloid cells may be dendritic cells, macrophages, neutrophils, monocytes, basophils, neutrophils, mast cells, and/or eosinphils. In particular aspects, the myeloid cells are dendritic cells. Exemplary myeloid differentiation and expansion medium are described, for example, in Tables 4-6.

In one exemplary method, HPCs are transferred in low attachment plates to a medium containing SFEM (Stem Cell Technologies), heparin (e.g., 1 to 10 U/mL, such as 5 U/mL, Sigma), TPO (e.g., 50 to 150 ng/mL, such as 100 ng/mL), human recombinant SCF (e.g., 50 to 150 ng/mL, such as 100 ng/mL), FLT3L (e.g., 50 to 150 ng/mL, such as 100 ng/mL), IL-3 (e.g., 1 to 20 ng/mL, such as 10 ng/mL), and IL-6 (e.g., 1 to 20 ng/mL, such as 10 ng/mL). After about 5-15 days, such as 8 days, myeloid cells are expanded in SFEM medium containing GM-CSF (e.g., 25 to 150 ng/mL, such as 100 ng/mL). Finally, the cells are cultured in a medium containing SFEM (Stem Cell Technologies), Excyte (e.g., 0.1% to 2%, such as 1%), GM-CSF (25 to 150 ng/mL, such as 100 ng/mL), IL-4 (10 to 30 ng/mL, such as 20 ng/mL), and TNFα (0.5 to 5 ng/mL, such as 2.5 ng/mL), for an additional 1-2 weeks to produce dendritic cells. The dendritic cells can be characterized by expression of one or more markers selected from the group consisting of $CD209^+$, $CD1a^+$, $HLA-DR^+$, $CD11c^+$, $CD14^+$, $CD83^+$, and $CD86^+$. These markers predominantly stain myeloid DCs and not plasmocytoid DCs ($CD123^+$). Wright staining can be performed on cytospin samples to confirm the classic morphology of dendritic cells.

D. Cell Culture

In certain embodiments, substantially hypoxic conditions may be used to promote differentiation of HPCs to myeloid or lymphoid lineages. In certain embodiments, an atmospheric oxygen content of less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, about 5%, about 4%, about 3%, about 2%, or about 1% may be used to promote differentiation into hematopoietic precursor cells. In certain embodiments, the hypoxic atmosphere comprises about 5% oxygen gas.

As described herein, one or more defined culture medium may be advantageously used to promote the differentiation of HPCs to myeloid and lymphoid lineages; in particular, the elimination of animal products such as serum and mouse feeder layers can reduce the risks associated with exposure of cells to animal products and allow for the generation of cells that could be more safely administered to a human subject. As traditional stem cell culture development has relied on serum products and mouse feeder layers for differentiating stem cells into a variety of cell types, these traditional procedures have limited the scale on which differentiation can be conducted, increased biological variability and potential contamination, and severely hampered the use of ES cells in translational therapies in which they might otherwise prove useful.

Generally, cells of the present disclosure are cultured in a culture medium, which is a nutrient-rich buffered solution capable of sustaining cell growth. Culture media suitable for isolating, expanding and differentiating pluripotent stem cells into hematopoietic precursor cells and hematopoietic cells according to the method described herein include but not limited to high glucose Dulbecco's Modified Eagle's Medium (DMEM), DMEM/F-15, RPMI 1640, Iscove's modified Dubelcco's media (IMDM), and Opti-MEM SFM (Invitrogen Inc.). Chemically Defined Medium comprises a minimum essential medium such as Iscove's Modified Dulbecco's Medium (IMDM) (Gibco), supplemented with human serum albumin, human ExCyte lipoprotein, transferrin, insulin, vitamins, essential and non-essential amino acids, sodium pyruvate, glutamine and a mitogen is also suitable. As used herein, a mitogen refers to an agent that stimulates division of a cell. An agent can be a chemical, usually some form of a protein that encourages a cell to commence cell division, triggering mitosis. In one embodiment, serum free media such as those described in U.S. Ser. No. 08/464,599 and WO 96/39487, and the "complete media" as described in U.S. Pat. No. 5,486,359 are contemplated for use with methods described herein. In some embodiments, the culture medium is supplemented with 10% Fetal Bovine Serum (FBS), human autologous serum, human AB serum or platelet rich plasma supplemented with heparin (2 U/ml).

Immune cells can be generated by culturing pluripotent stem cells or hematopoietic precursor cells in a medium under conditions that increase the intracellular level of factors sufficient to promote differentiation of the cells into myeloid or lymphoid lineages. The medium may also contain one or more hematopoietic cell differentiation and maturation agents, like various kinds of growth factors. These agents may either help induce cells to commit to a more mature phenotype—or preferentially promote survival of the mature cells—or have a combination of both of these effects. Differentiation and maturation agents may include soluble growth factors (peptide hormones, cytokines, ligand-receptor complexes, and other compounds) that are capable of promoting the growth of cells of the hematopoietic cell lineage. Non-limiting examples of such agents include but are not limited to hematopoietic or endothelial growth factors such as fibroblast growth factor (FGF), vascular endothelial growth factor (VEGF), stem cell factor (SCF), thrombopoietin (TPO), FLT-3 ligand (FLT3L), interleukin-3 (IL-3), interleukin-6 (IL-6), interleukin-9 (IL-9), or granulocyte colony-stimulating factor (G-CSF), or isoforms or variants thereof.

IV. Uses of Immune Cells

The immune cells provided by methods and compositions of certain aspects can be used in a variety of applications. These include but are not limited to transplantation or implantation of the cells in vivo; screening cytotoxic compounds, carcinogens, mutagens growth/regulatory factors, pharmaceutical compounds, etc., in vitro; elucidating the mechanism of hematological diseases and injuries; studying the mechanism by which drugs and/or growth factors operate; diagnosing and monitoring cancer in a patient; gene therapy; and the production of biologically active products, to name but a few.

A. Test Compound Screening

Immune cells of this disclosure can be used to screen for factors (such as solvents, small molecule drugs, peptides, and polynucleotides) or environmental conditions (such as culture conditions or manipulation) that affect the characteristics of lymphoid cells provided herein.

Particular screening applications of this disclosure relate to the testing of pharmaceutical compounds in drug research. The reader is referred generally to the standard textbook *In vitro Methods in Pharmaceutical Research*, Academic Press, 1997, and U.S. Pat. No. 5,030,015. In certain aspects, myeloid and lymphoid cells play the role of test cells for standard drug screening and toxicity assays, as have been previously performed on hematopoietic cells and precursors in short-term culture. Assessment of the activity of candidate pharmaceutical compounds generally involves combining the hematopoietic cells or precursors provided in certain aspects with the candidate compound, determining any change in the morphology, marker phenotype, or metabolic activity of the cells that is attributable to the compound (compared with untreated cells or cells treated with an inert compound), and then correlating the effect of the compound with the observed change. The screening may be done either because the compound is designed to have a pharmacological effect on hematopoietic cells or precursors, or because a compound designed to have effects elsewhere may have unintended effects on hematopoietic cells or precursors. Two or more drugs can be tested in combination (by combining with the cells either simultaneously or sequentially), to detect possible drug-drug interaction effects.

B. Hematopoietic Cell Therapy

This disclosure also provides for the use of immune cells provided herein to restore a degree of function to a subject needing such therapy, perhaps due to a hematological disease or disorder or an injury. For example, immune cells derived by methods disclosed herein may be used to treat hematological diseases and disorders such as hemoglobinopathies, anemias, etc. Such cells may be useful for the treatment of hematopoietic cell deficiencies caused by cell-suppressive therapies, such as chemotherapy.

To determine the suitability of cells provided herein for therapeutic applications, the cells can first be tested in a suitable animal model. At one level, cells are assessed for their ability to survive and maintain their phenotype in vivo. Cells provided herein are administered to immunodeficient animals (such as NOG mice, or animals rendered immunodeficient chemically or by irradiation) at a site amenable for further observation, such as under the kidney capsule, into the spleen, into a liver lobule, or into the bone marrow. Tissues are harvested after a period of a few days to several weeks or more, and assessed as to whether starting cell types such as erythrocytes are still present. This can be performed by providing the administered cells with a detectable label (such as green fluorescent protein, or (β-galactosidase); or by measuring a constitutive marker specific for the administered human cells. Where cells provided herein are being tested in a rodent model, the presence and phenotype of the administered cells can be assessed by immunohistochemistry or ELISA using human-specific antibody, or by RT-PCR analysis using primers and hybridization conditions that cause amplification to be specific for human polynucleotide sequences. Suitable markers for assessing gene expression at the mRNA or protein level are provided elsewhere in this disclosure.

Immune cells provided by methods of the present disclosure may be tested in various animal models for their ability to treat hematological disorders and injuries. For example, a sickle cell anemia mouse model or the T/B cell-deficient Rag-2 knockout mouse may be particularly useful animal models for testing the myeloid and lymphoid cells disclosed herein.

Immune cells provided in certain aspects of the present disclosure that demonstrate desirable functional characteristics or efficacy in animal models, may also be suitable for direct administration to human subjects in need thereof. For purposes of hemostasis, the cells can be administered at any site that has adequate access to the circulation. Hematopoietic cells or precursors thereof may also be delivered at a site of injury or disease.

The cells provided in certain aspects of this present disclosure can be used for therapy of any subject in need thereof. Human conditions that may be appropriate for such therapy include the various anemias and hemoglobinopathies, as well as diseases characterized by decreased numbers of hematopoietic cells (such as, for example, myelodysplastic syndrome, myelofibrosis, neutropenia, agranulocytosis, Glanzmann's thrombasthenia, thrombocytopenia, and acquired immune deficiency syndrome). For human therapy, the dose is generally between about $10^9$ and $10^{12}$ cells, and typically between about $5 \times 10^9$ and $5 \times 10^{10}$ cells, making adjustments for the body weight of the subject, nature and severity of the affliction, and the replicative capacity of the administered cells. The ultimate responsibility for determining the mode of treatment and the appropriate dose lies with the managing clinician.

C. Distribution for Commercial, Therapeutic, and Research Purposes

For purposes of manufacture, distribution, and use, the immune cells of this disclosure are typically supplied in the form of a cell culture or suspension in an isotonic excipient or culture medium, optionally frozen to facilitate transportation or storage.

Also provided herein are different reagent systems, comprising a set or combination of cells that exist at any time during manufacture, distribution, or use. The cell sets comprise any combination of two or more cell populations described in this disclosure, exemplified but not limited to programming-derived cells (hematopoietic lineage cells, their precursors and subtypes), in combination with undifferentiated stem cells, somatic cell-derived hematopoietic cells, or other differentiated cell types. The cell populations in the set sometimes share the same genome or a genetically modified form thereof. Each cell type in the set may be packaged together, or in separate containers in the same facility, or at different locations, at the same or different times, under control of the same entity or different entities sharing a business relationship.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Production of T Cell-Derived PSCs (TiPSCs)

For the production of iPS cells, T cells were isolated from a blood sample and activated prior to retroviral reprogramming to iPSCs. First, peripheral blood mononuclear cells (PBMCs) were expanded in freshly prepared AIM-V Medium+pen/strep/glutamine (AIV-V/ps/s/g media) (Invitrogen) plus 300 IU/ml rhIL2 (Peprotech) and 10 ng/ml soluble anti-CD3 antibody (OKT3 clone, eBiosciences) and anti-CD28 antibody. Several days after activation exponential growth was verified by CEDEX cell count. After 3 days in culture cells were assayed for T-cell phenotype and then transduced with the reprogramming factors.

Retroviral vectors Nanog RFP, Lin28 RFP, Oct4 eGFP, and Sox2 eGFP were constructed as described previously (see U.S. Application No. 61/088,054, incorporated herein by reference). Retroviral vectors c-Myc RFP, Klf4 RFP, Oct4 eGFP, and Sox2 eGFP were constructed similarly.

The CD3- and CD28-activated peripheral mononuclear cells were cultured in T cell medium comprising AIM-V medium containing 2% human AB serum and 10 ng/mL IL-2. At day 6, the T cells were transfected with 6 reprogramming factors through electroporation using the Amaxa U-014 program ($1-5\times10^6$ cells/transfection, Amaxa T cell transfection solution). Up to day 25 post-transfection, the cells were cultured on retronectin (0.3 µg/cm$^2$)- and vitronectin (0.2 µg/cm$^2$)-coated wells of 6-well plate at one transfection per well and with gradual transition from T cell to E8 PSC medium beginning on day 14.

Activated and expanding T cells displayed characteristic cell morphology and clustering behavior. Detection of retroviral transduction efficiency was determined by GFP and RFP expression 72 h post initial transduction, over the course of ~3 weeks the transgenes were silenced and display an hES cell phenotype. Well defined iPS cell colonies began to appear on day 23. GFP and RFP silencing was verified by fluorescent microscopy and colonies were picked in a dissecting hood using a pipette tip. Colony pieces were then transferred to fresh 6 well plates. The number of colonies were counted to estimate reprogramming efficiency given the number of input plated cells. From this point clonal colonies were fed daily and manually passaged one more time and then expanded to produce the TiPSCs lines.

Example 2

TiPSC Differentiation to Hematopoietic Precursor Cells (HPCs)

Various episomally and virally reprogrammed iPSCs (Table 1), including the TiPSCs of Example 1, were subjected to the 3D differentiation protocol for the production of HPCs (FIG. 1). First, the iPSCs were acclimatized to hypoxic conditions for 5-10 passages under feeder-free conditions on Matrigel™- or Vitronectin-coated ultra-low attachment (ULA) plates in Essential 8 (E8) media. Aggregates were made from sub confluent iPSCs at a density of 0.25-0.5 million cells per ml in the presence Serum Free Defined (SFD) media supplemented with 5 uM blebbistatin. The process was performed in ultra-low attachment (ULA) plates or spinner flasks in SFD basal medium containing 75% IMDM (Invitrogen 12200-069) (with Glutamine and 25 mM HEPES+P/S), 25% Hams F12 (Mediatech 10-080-CV), 0.5% N2-supplement (Invitrogen 17502-048), 1% B27 supplement without retinoic acid (Invitrogen 12587-010), 0.05% BSA, 50 ug/ml Ascorbic acid, and $4.5\times10^{-4}$ M monothioglycerol.

Figure 1B:
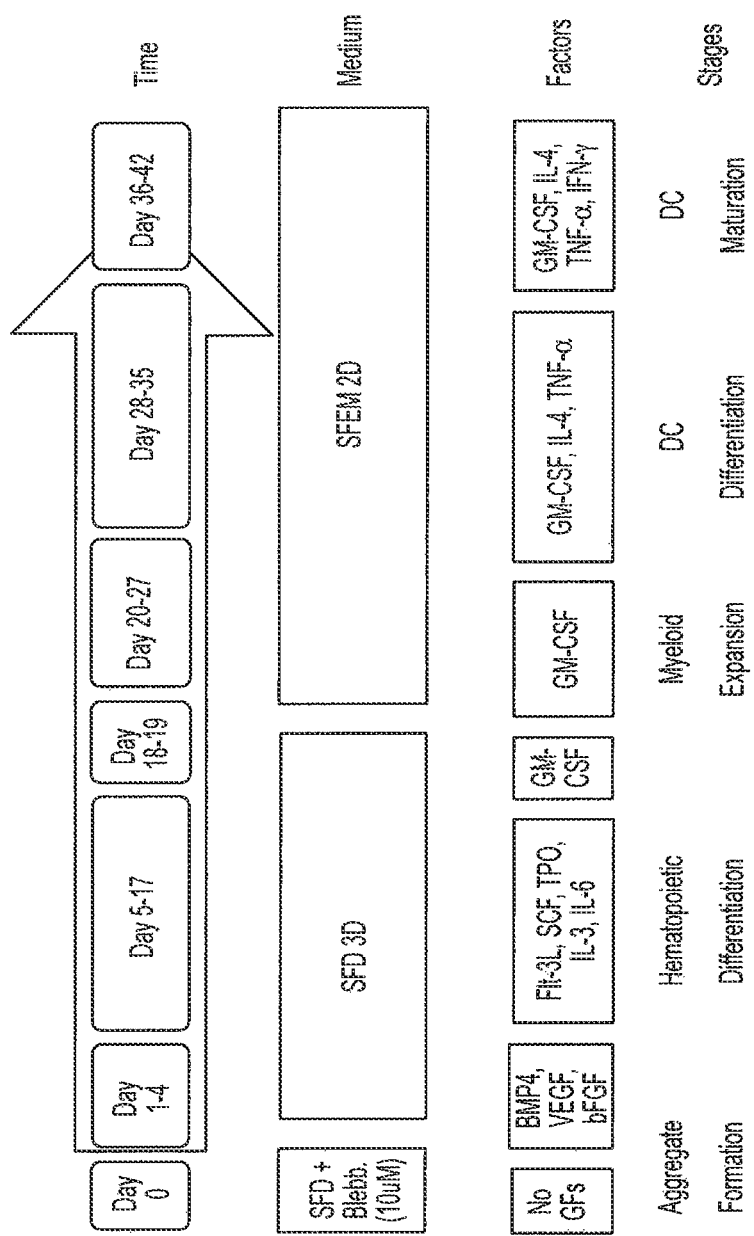
Figure 1C:
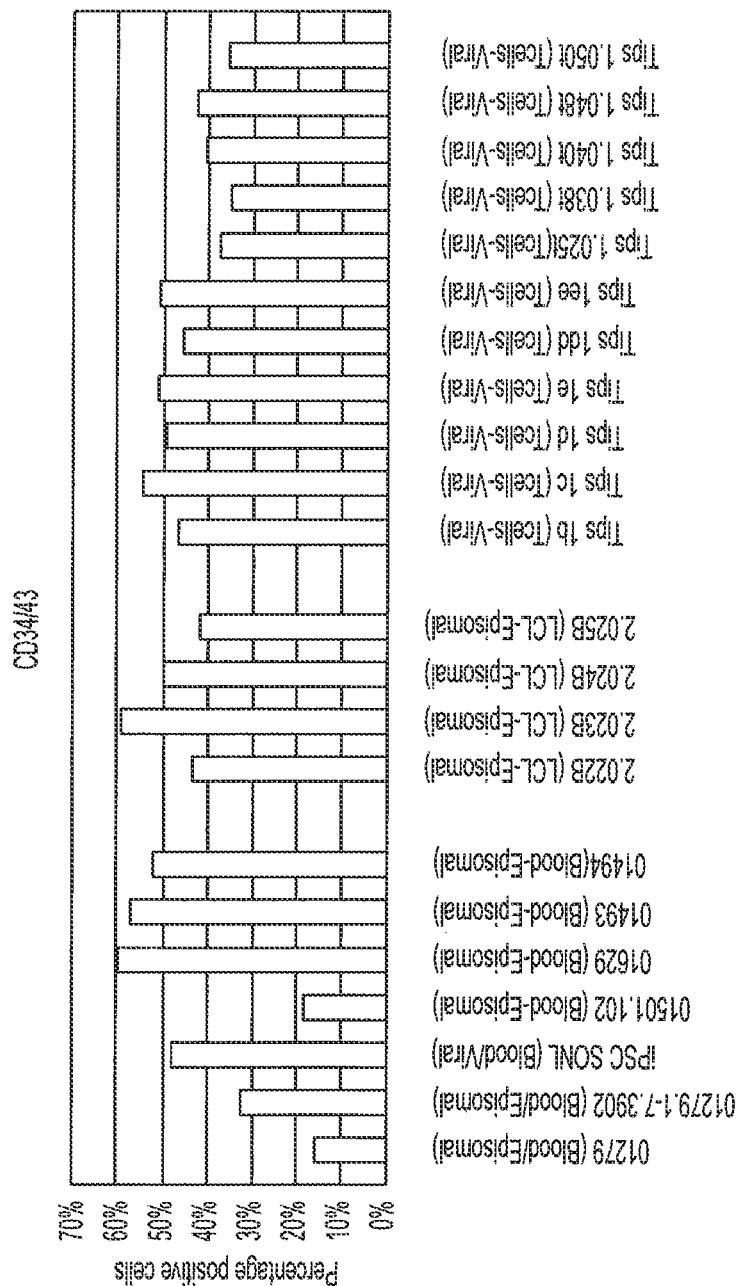
Figure 2:
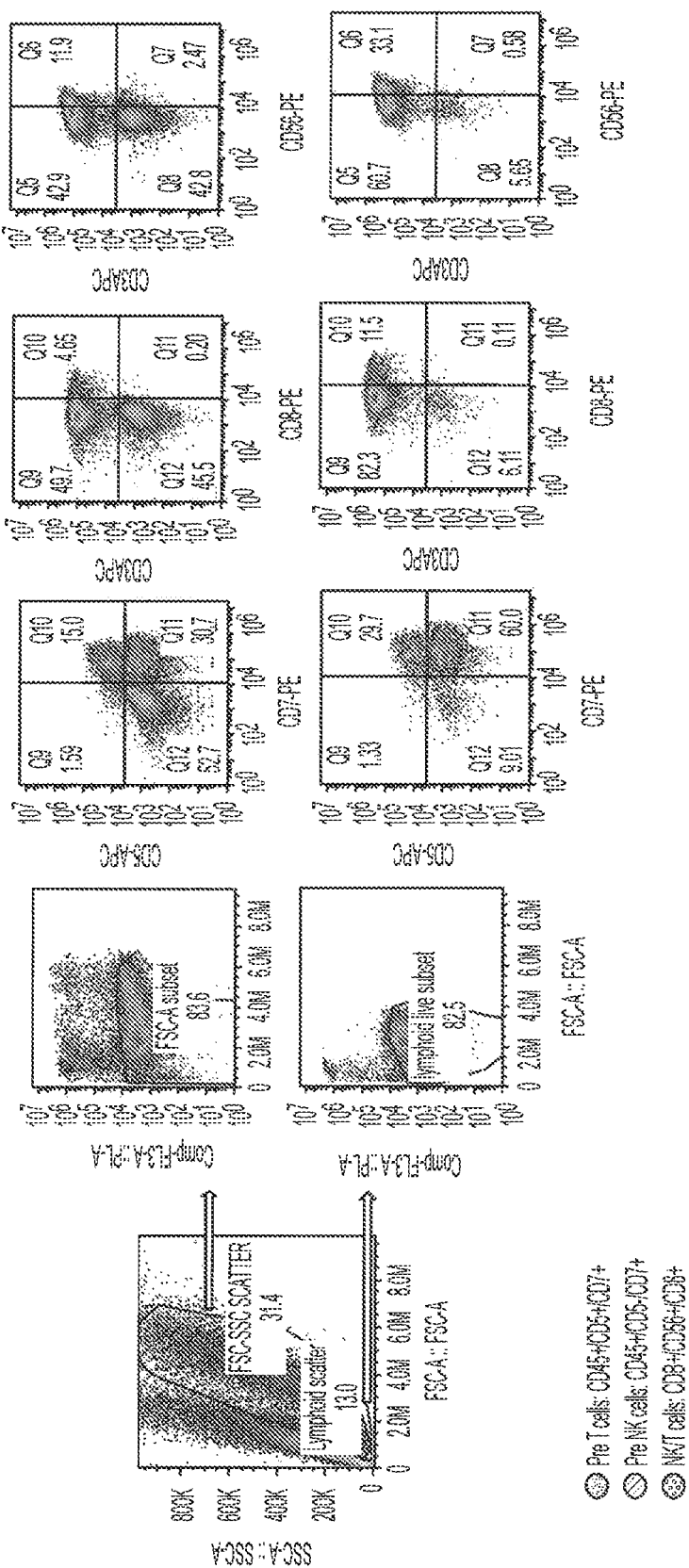
FIG. 2: Flow cytometry scatter plots are shown which identify lymphoid and lympho-myeloid populations during lymphoid differentiation of the Day 7-10 HPCs. The presence of pre T, NK, and NK/T cells was determined.

Once the EBs had formed, differentiation was initiated by supplementing the SFD basal media with 50 ng/ml of BMP-4, VEGF, and FGF2 for the first 4 days. On the fifth day of differentiating the EBs, the cultures were placed in the presence of Flt-3 Ligand, IL3, IL6, SCF, and TPO each at 50 ng/ml and heparin at 5000 units. The EB cultures were supplemented with half the volume of fresh differentiation media containing cytokines every 2 days during the differentiation process until day 12-16 of differentiation under hypoxic conditions. The cells were harvested after the differentiation process and the phenotype was assessed by flow cytometry and the functional capability was assessed using the CFU assay. The cells were harvested and the percentage of CD43/CD34 cells was quantified by flow cytometry (FIG. 1B). The efficiency of the process was calculated by dividing the absolute number of HPCs generated per input number of iPS cells (FIG. 1C).

TABLE 1

Process Validation using Multiple iPSC Lines

| Cell line | Reprogramming Method | Source material for reprogramming | |
|---|---|---|---|
| 01501.102 | Episomal | Progenitor cells Blood | Male |
| TiPSCs1E | Viral | T cells | Male |
| 1.025T | Viral | T cells | Female |
| 2.022B | Episomal | LCL | Male |
| 2.0224B | Episomal | LCL | Female |
| 01279.107.3902 | Episomal | Progenitor cells blood | Male |
| 01279.107.3908 | Episomal | Progenitor cells blood | Male |
| 01279.107.3904 | Episomal | Progenitor cells blood | Male |
| 01279 | Episomal | Progenitor cells blood | Male |
| 01629 | Episomal | Progenitor cells blood | Male |

For flow cytometry analysis, the cells were collected and washed once with media. The cell pellet was digested using TrypLE™ or 0.5% trypsin for 5-10 minutes in a 37° C. incubator followed by washes with media and passaged through a 70-µm cell strainer. The cells were resuspended in PBS-FBS containing FACS buffer, counted to estimate cell viability and stained with fluorochrome-conjugated monoclonal antibodies: anti-human CD43 (1G10), anti-human CD31 (WM-59), anti-human CD41 (HIPS); anti-human CD45 (HI30); anti-human CD34 (581, 8G12) (BD Biosciences San Jose, Calif.); and anti-human CD235. Non-viable cells were excluded with 7-aminoactinomycin D (7-AAD, BD Biosciences). Live cell analysis was performed on a FACSCalibur™ or Accuri flow cytometer and Cell Quest software.

For the clonogenic hematopoietic progenitors assay (CFU assay) the EBs were dispersed into single cell suspensions using TrypIE or 0.5% trypsin/EDTA. Viable cells were quantified, plated (50,000-300,000 cells per mL), and assayed in humidified chambers for hematopoietic CFCs in using Human Methylcellulose Complete Media (R&D Systems, Minneapolis, Minn.) containing stem cell factor (SCF) 50 ng/mL, erythropoietin (EPO) 3 U/mL, granulocyte-macrophage colony-stimulating factor (GM-CSF) 10 ng/mL, interleukin-3 (IL-3) 10 ng/mL. After 14 days the colonies were scored according to their morphology and colonies per $10^5$ cells plated were quantified.

Example 3

Modified iPSC Differentiation to Hematopoietic Precursor Cells (HPCs)

The 1C T-cell derived iPSCs (TiPSC, derived by retroviral reprogramming) were differentiated to CD34$^+$ hematopoietic progenitors through aggregate suspension (3D) culture. 1C cells were maintained under feeder-free conditions on Matrigel™- or Vitronectin-coated 6-well plates in Essential 8 (E8) medium. Aggregates were made from sub-confluent 1C cells (<80% confluence) at a density of 0.5-1 million cells per ml in the Essential 3 (E3) medium (containing only 3 of 8 components of E8 medium: DMEM/F12 basal medium, ascorbic acid 2-phosphate magnesium and sodium selenite) supplemented with 50 ng/ml FGF2, 50 ng/ml VEGF, 2 µM CHIR99021 (GSK-3 inhibitor), and 10 µM blebbistatin (myosin-II inhibitor). The aggregate formation was performed during 24 hour culture in ultra-low attachment (ULA) flasks under continuous agitation on the rocker platform at 15 rpm (including all subsequent culture steps).

The formed cell aggregates (i.e., embryoid bodies—EBs) were further transferred to serum-free differentiation medium (50% IMDM, 50% Hams F12 medium, 100 µg/ml polyvinyl alcohol, 100 µg/ml recombinant human serum albumin, lx non-essential amino acid supplement (Invitrogen), 0.1× chemically-defined lipid supplement (Invitrogen), 125 µM ascorbic acid 2-phosphate magnesium, 0.25 µM linoleic acid, trace element supplements A (0.3×), B (0.2×) and C (0.1×) (Corning), 5 mM sodium chloride, 100 µM monothioglycerol, 20 µM ethanolamine, 100 ng/ml heparin, and 10 ng/ml IGF1) supplemented with hematopoietic mesoderm inducing cytokines—25 ng/ml BMP4, 50 mg/ml VEGF and 50 ng/ml FGF2. Cultures were continued for 4 days with complete medium change on the second day.

To support differentiation and expansion of hematopoietic CD34+ progenitors, cell aggregates were further transferred to serum-free differentiation medium (as above) supplemented with hematopoietic supportive cytokines—50 ng/ml SCF, 20 mg/ml TPO, 10 ng/ml FLT3L, 20 ng/ml IL-3, and 25 ng/ml BMP4. Cultures were continued for 4 days with complete medium change on the second day.

The cultures were harvested during Days 7-9 of the differentiation process. A single cell suspension was obtained through digestion of differentiated cell aggregates in the Accutase (or Accumax) solution for 15-20 min at 37° C. Cells were washed in MACS buffer (e.g., PBS containing 5 mg/ml BSA and 1 mM EDTA), filtrated through 70 µM cell strainers and labeled with direct CD34 paramagnetic microbeads (Miltenyi Biotec) 30 min at 4° C. CD34$^+$ cells were isolated using MS or LS magnetic columns, appropriate magnets and standard separation procedures according to recommendations from manufacturer (Miltenyi Biotec). Isolated CD34$^+$ cells were plated to T/NK differentiation cultures or cryopreserved for later use within 1 hour after isolation.

Example 4

Lymphoid Differentiation of HPCs

To determine the parameters for lymphoid differentiation of the HPCs of Example 2 and Example 3, the cell lines were subjected to culture conditions for T and NK cell differentiation. First, several variables were tested for T cell differentiation were tested in a stroma dependent protocol. The day 12 HPCs from different cell lines were tested for T cell potential on stromal lines, including OP9 bone marrow stromal cells and MS5 murine bone marrow stromal cells. The cells were cultured in αMEM media with 20% FBS, 10 ng/mL SCF, 5 ng/mL Flt-3 and 5 ng/mL IL-7. The cells were refreshed by a half-medium change three times a week. Analysis of the cells for the presence of T cells showed that the cells had a tendency to generate myeloid cells and the presence of CD3$^+$ cells could not be detected. In addition, the stromal co-cultures performed poorly under hypoxic conditions.

TABLE 2

Choice of matrix for lymphoid differentiation. Cells plated on Retronectin-DLL4 revealed the presence of pre T cells (CD5$^+$/CD7$^+$) cells.

| Matrix for T cell Differentiation | % CD5 | % CD7 | % CD5/CD7 |
| --- | --- | --- | --- |
| Retronectin-DLL4 | 11% | 40% | 11% |
| Tenascin-DLL4 | 0.7% | 5.2% | 0.7% |
| Vitronectin-DLL4 | 0.6% | 6% | 0.6% |

TABLE 3

Hypoxia favors T cell differentiation. Cells differentiating under hypoxic conditions revealed the presence of T and NK cells.

| Matrix for T cell Differentiation | CD3 | CD4 | CD8 | CD3/CD4 | CD3/CD4 | CD4/CD8 | CD56+/CD3− (NK cells) |
| --- | --- | --- | --- | --- | --- | --- | --- |
| Hypoxia | 7% | 11.4% | 49% | 2.6% | 2% | 5.6% | 28% |
| Normoxia | 0.2 | 57% | 4.7% | 0 | 0 | 0 | 6% |

Accordingly, a feeder free T cell differentiation protocol was developed. The HPCs were plated on non-treated tissue culture plates coated with Retronectin and Notch DLL4 at 0.5 µg/cm$^2$ at a cell density of about 5,000 to about 25,000 cells/cm$^2$. The HPCs were cultured in StemSpan Serum-Free Expansion Medium II (SFEM; StemCell Technologies) media supplemented with 1% Glutamax, 1% Penicillin Streptomycin, 95 µM Ascorbic acid (WAKO labs), as well as 50 ng/mL of IL-7, SCF, Flt-3, and TPO (Peprotech). The media was replenished every 48 hours and at 2 weeks the cells were split to new ligand coated plates. In addition, between 2 and 3 weeks the cells were analyzed for the presence of pre-T cells by the cell surface markers CD5 and CD7. At 4 weeks, the cells were analyzed for the presence of T cells by the cell surface markers CD3, CD4 and CD8. At 6-8 weeks, the cells were analyzed for the presence of T and NK cells using the cell surface markers CD4, CD8, CD3, CD94 and CD56.

One of the parameters tested for its effect on T cell differentiation was the choice of the matrix coating on the culture plates. A comparison was performed by analyzing the emergence of pre-T cells under serum free conditions using various matrix combinations with Notch DLL4 with cord blood cells at 3 weeks post-plating. The results showed that the combination of retronectin with DLL4 was more effective at differentiating the cord blood cells to pre-T cells than the combination with vitronectin or tenascin (Table 2).

Surprisingly, it was found that hypoxic conditions enhance feeder-free T cell differentiation. Specifically, it was observed that hypoxia resulted in an increase in the percentage of cells positive for CD8 and a decrease in the percentage of cells positive for CD4 as compared to the cell differentiated under normoxic conditions (Table 3).

Figure 3A:
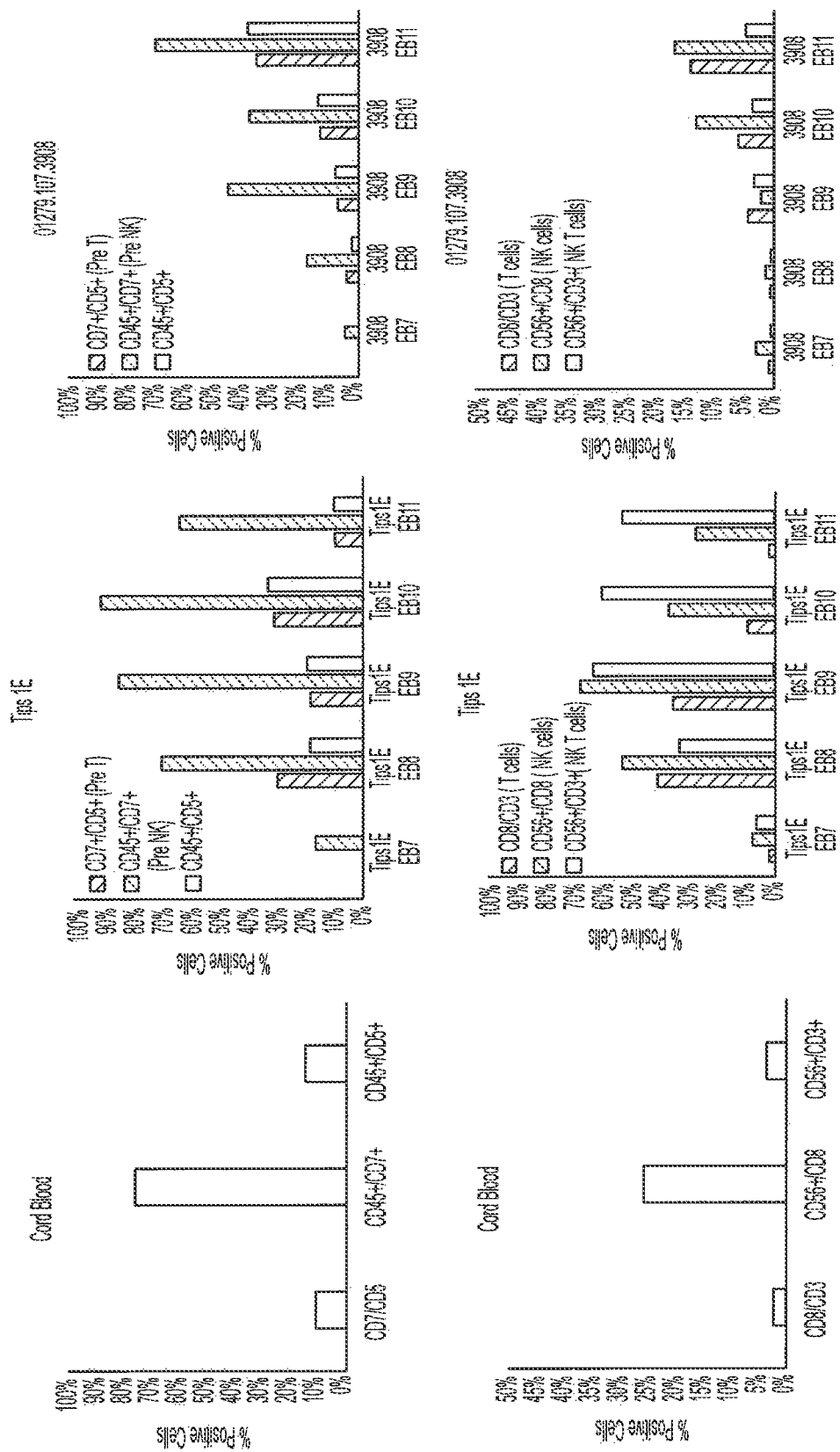
FIGS. 3A-3D: (A) Representative staining profile to detect the emergence of lymphoid cells from virally and episomally reprogrammed iPSCs, including cord blood-derived iPSCs, virally reprogrammed T cell iPSCs (TiPSCs), and episomally reprogrammed progenitor blood cell iPSCs (01279.107.3908). The cells were stained for the surface 2The percentage of cells were quantified by flow cytometry under FSC-SSC and the lymphoid scatter gates. (EB7=Day 7, EB8=Day 8, EB9=Day 9, EB10=Day 10, and EB11=Day 11. (B) Day 7-11 HPCs differentiated from TiPSCs (top: Total HPCs; bottom: CD43$^+$CD34$^+$ HPCs) were further differentiated to lymphoid cells and stained for the surface expression of CD45, CD7, and CD5. The percentage of cells were quantified by flow cytometry under FSC-SSC and the lymphoid scatter gates. (C) Day 7-11 HPCs generated from TiPSCs (top: Total HPCs; bottom: CD43$^+$CD34$^+$ HPCs) were differentiated under hypoxic conditions and stained for the surface expression of CD56, CD8, and CD3. (D) The efficiency of generating lymphoid cells from TiPSCs is shown (left: Total HPCs; right: CD43$^+$CD34$^+$ HPCs).
Figure 3B:
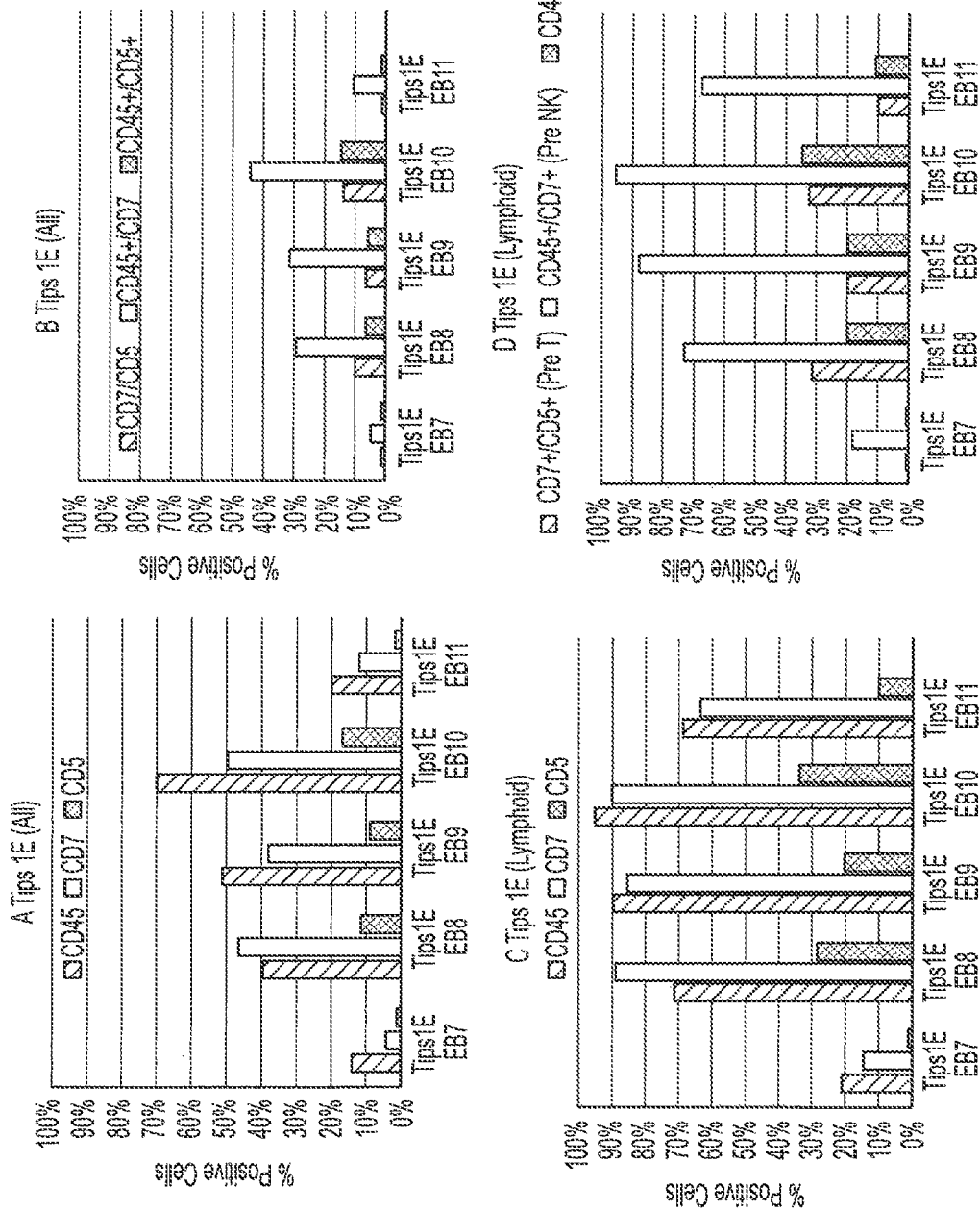
Figure 3C:
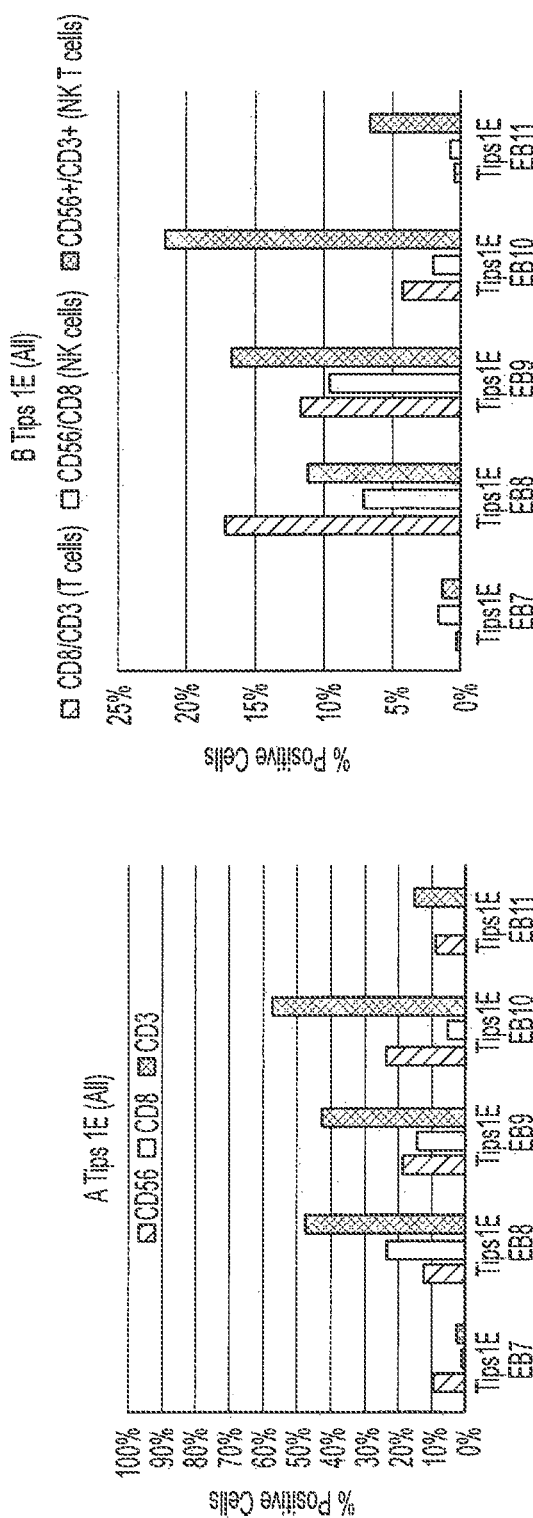
Figure 3C:
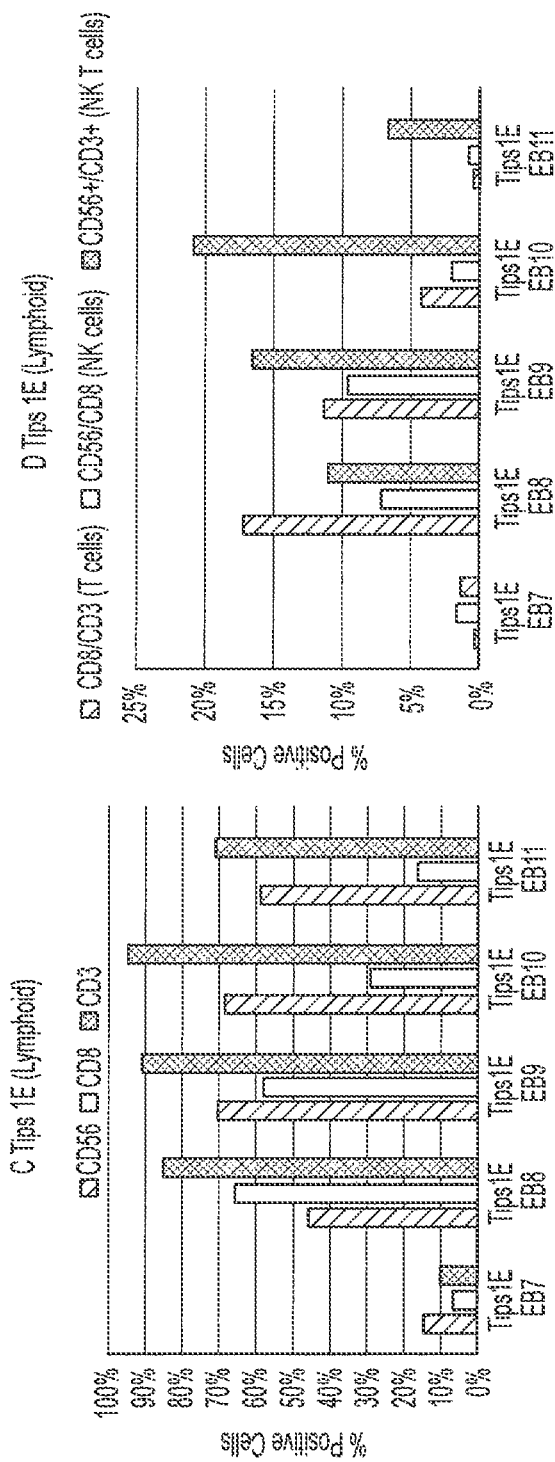
Figure 3D:
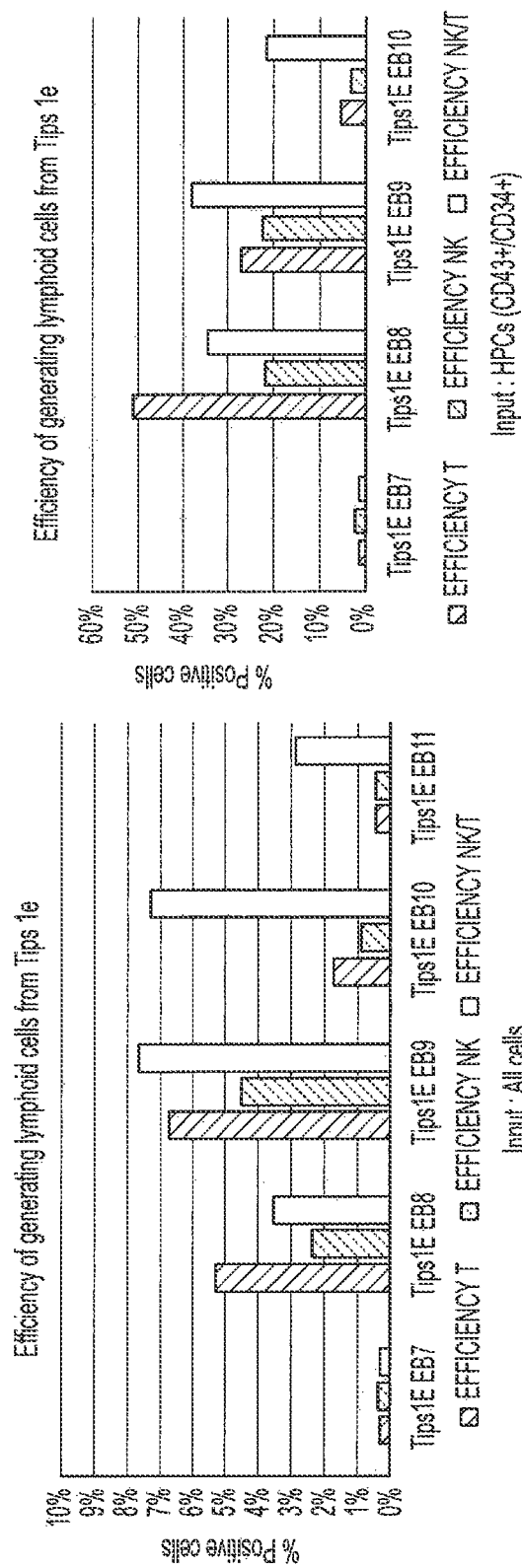

The efficiency of differentiating the blood cell-derived iPSCs to lymphoid lineages was analyzed by harvesting the various cell lines at day 5, day 7, day 9 and day 11 of the HPC differentiation described in Example 2. The HPC cells were thawed and plated on Retronectin and DLL4 coated plates. The cells were fed fresh media every 2 days and were analyzed for pre-T cells markers at 2 weeks, T cell markers at 4 weeks and T and NK cell markers at 6 weeks after the HPC cells were thawed. The cells were stained for the surface expression of CD7, CD8, CD56 (FIG. 3A), CD45, CD7, CD5 (FIG. 3B), and CD56, CD8, CD3 (FIG. 3C) for the presence of T, NK and NK/T cells. The TiPSCs and the episomally reprogrammed 3908 cells were observed to have an increased lymphoid potential at Days 7-11 (FIG. 3A).

Figure 4:
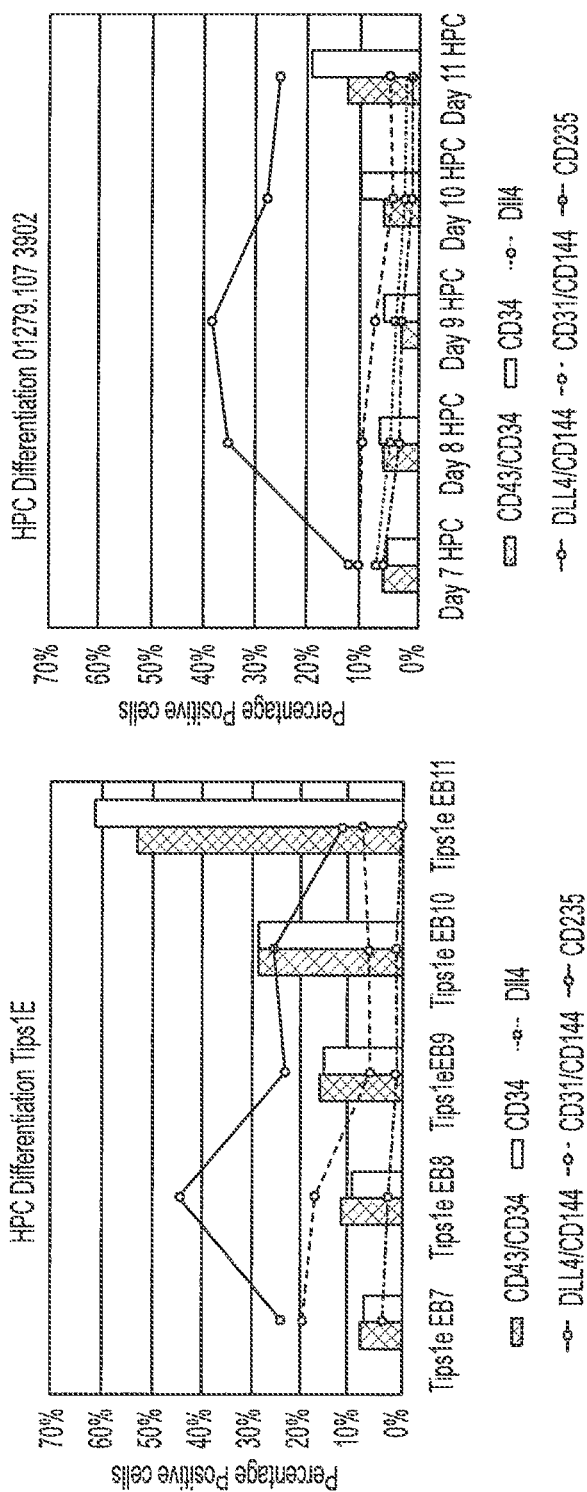
FIG. 4: Day 7-11 HPCs differentiated from TiPSCs (e.g., virally reprogrammed TiPSCs1E or episomally reprogrammed 01279.107.3902) were analyzed for the expression of CD43/CD34, CD34, Dll4, Dll4/CD144, CD31/CD144, and CD235 at various days of HPC differentiation from day 7 to day 11. The percentage of cells positive for each set of markers if shown. The CD43/CD34 expression is shown in the left column, CD34 right column, DLL4/CD144 bottom line, CD31/CD144 middle line, and CD235 top line.

To determine if the surface markers could be used to increase the efficiency of lymphoid differentiation, analysis of CD43/CD34, CD34, DLL4, CD31/CD144, and CD235 was performed on both the TiPSCs1E line and the episomal 3902 line (FIG. 4). It was found that expression of DLL4 and levels of CD235 decline at Day 11 of differentiation while CD34 expression decreases and CD43 expression increases with the days of differentiation. Since there is absence of lymphoid cells at day 11 of differentiation, it implies that a certain threshold level of expression of these markers is essential to prime cells towards lymphoid differentiation in the presence of DLL4.

Figure 5:
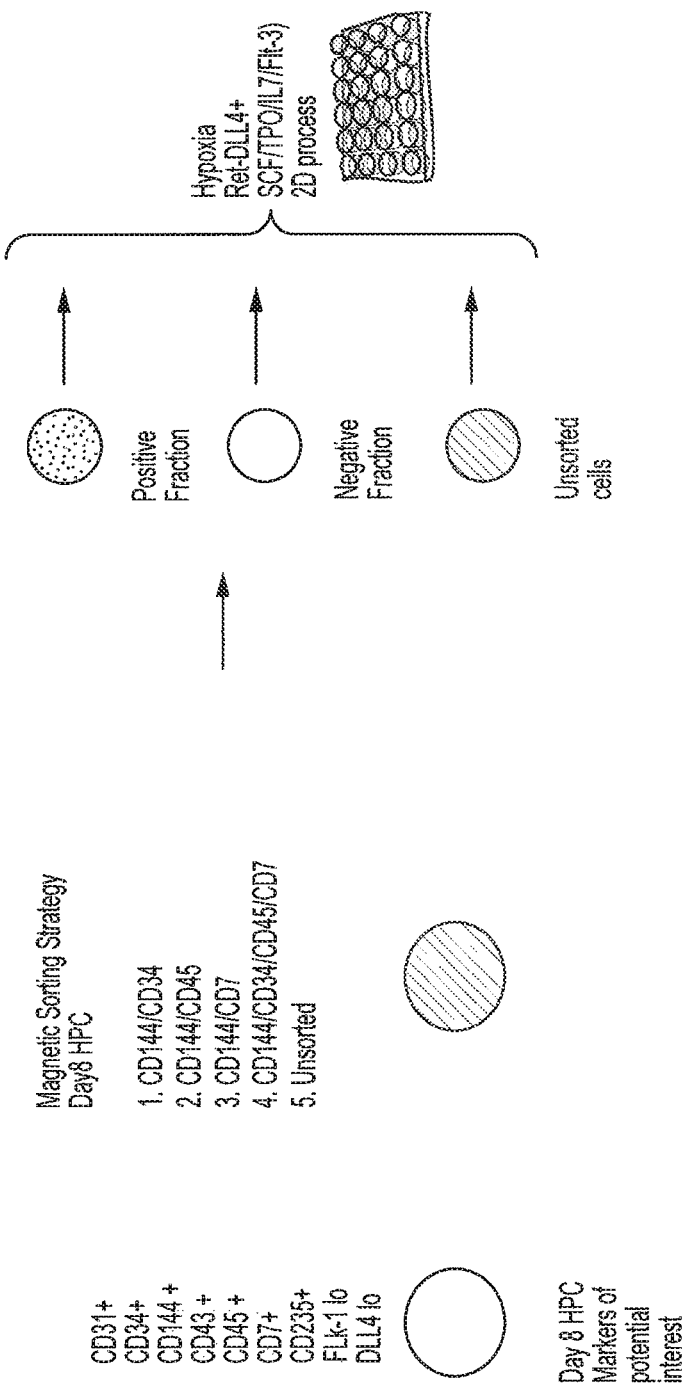
FIG. 5: Schematic of magnetic sorting strategy to detect lymphoid progenitors during HPC differentiation. The markers of interest included CD31, CD34, CD144, CD43, CD45, CD7, CD235 FLK1 (also known as KDR, VEGFR2, CD309) and DLL4. At Day 8 of differentiation, the cells were sorted into various fractions based upon the markers of interest and then subjected to the lymphoid differentiation process.
Figure 6A:
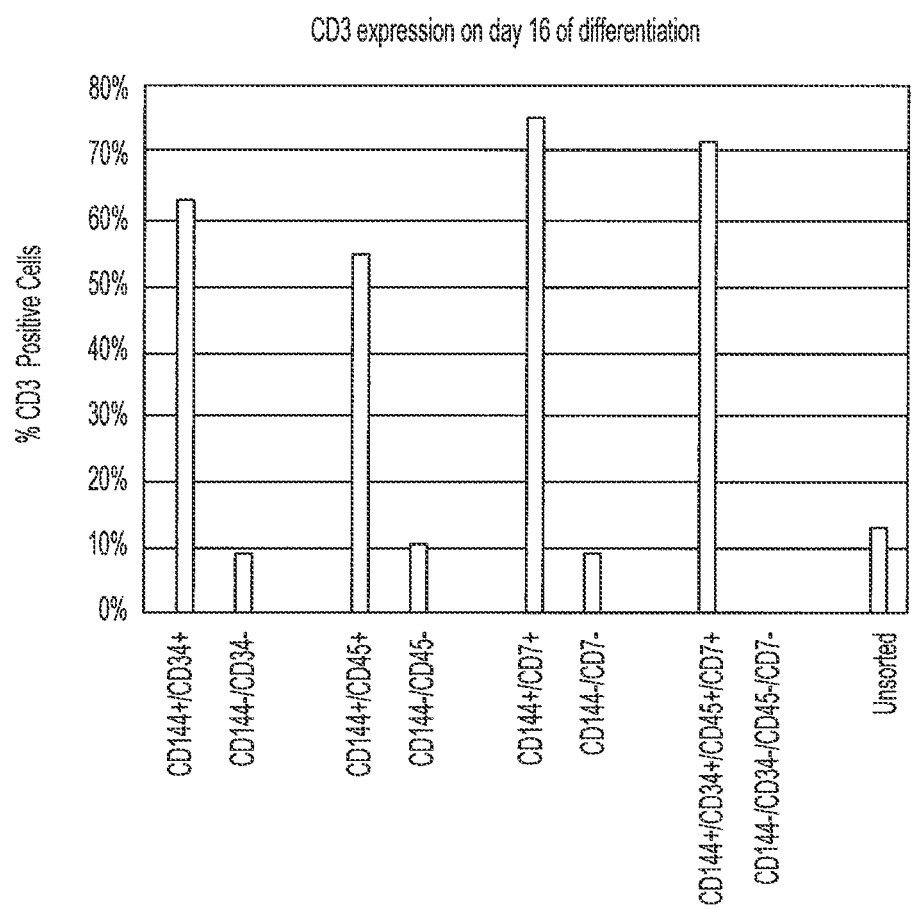
FIGS. 6A-6B: (A) The percentage of CD3 positive cells in each positive and negative fraction of cells from the magnetic sorting strategy of FIG. 5 is shown with unsorted cells as the control. (B) The fold enrichment of T cells generated from the HPCs is shown for the positive and negative fractions from the magnetic sorting strategy of FIG. 5 with unsorted cells as the control.
Figure 6B:
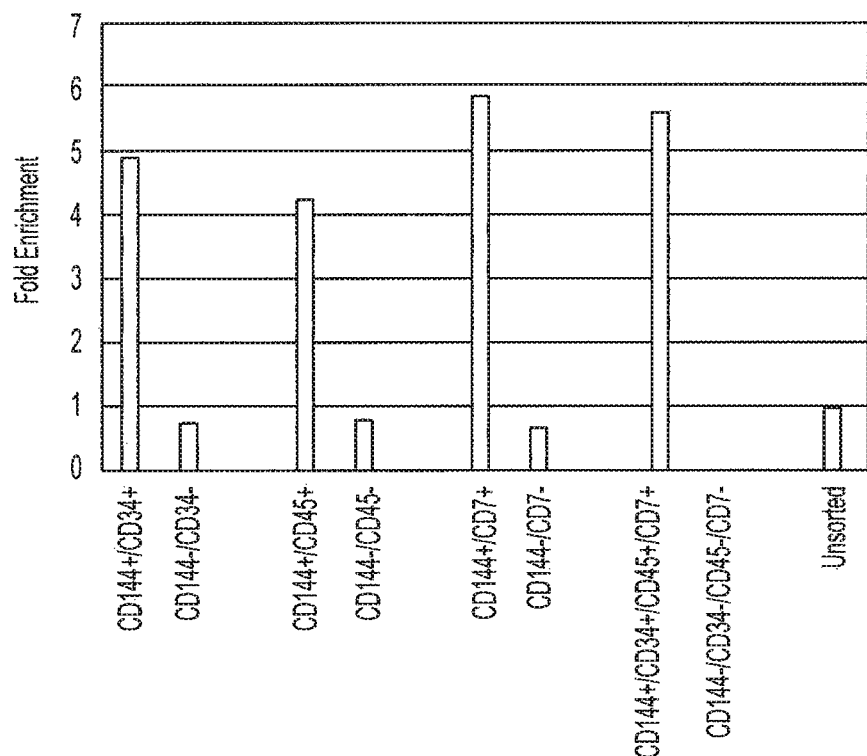

Further analysis of lymphoid progenitors during HPC differentiation was performed by magnetic sorting of the surface markers CD31, CD34, CD144, CD43, CD45, CD6, CD335, Flk-1, and DLL4. Day 8 HPCs were sorted into CD114/CD34, CD144/CD45, CD144/CD7, and CD144/CD34/CD45/CD7 positive and negative fractions as well as an unsorted control (FIG. 5). These fractions were then subjected to the lymphoid differentiation process and analyzed for the presence of $CD3^+$ cells at Day 16 (FIG. 6A). It was observed that each of the positive fractions displayed lymphoid potential significantly increased as compared to the negative fractions and the unsorted control. This was further supported by the increase in fold enrichment of T cell generation from the positive fraction magnetic sorting (FIG. 6B). The positive fractions were plated back on fresh Ret-DLL4 surface for an additional two weeks.

Figure 7A:
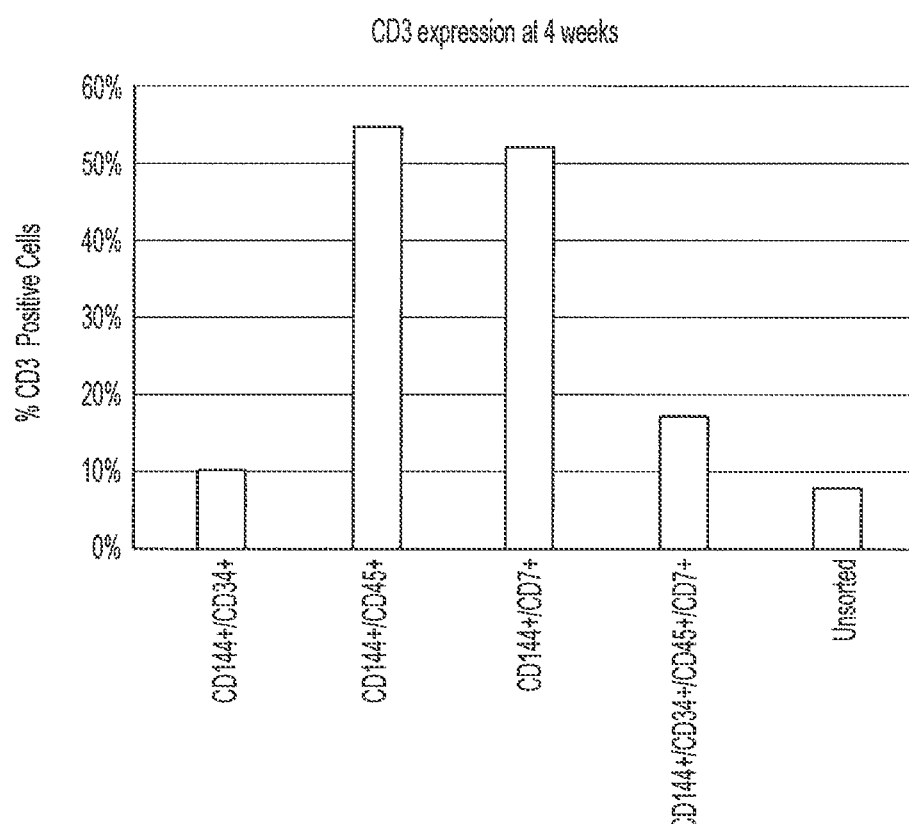
FIGS. 7A-7B: (A) The percentage of CD3 positive cells for each positive fraction of cells from the magnetic sorting of FIG. 5 after 4 weeks of lymphoid differentiation from TiPSCs is shown. (B) FACS plot of 5 week differentiation from TiPSCs1E cells. Flow cytometry analysis of the CD3 positive cells for expression of emerging lymphoid cells are CD7+, CD5+, CD3+, CD8+, CD56+CD335+, CD161+, TCR αβ+, TCR γδ−.
Figure 7B:
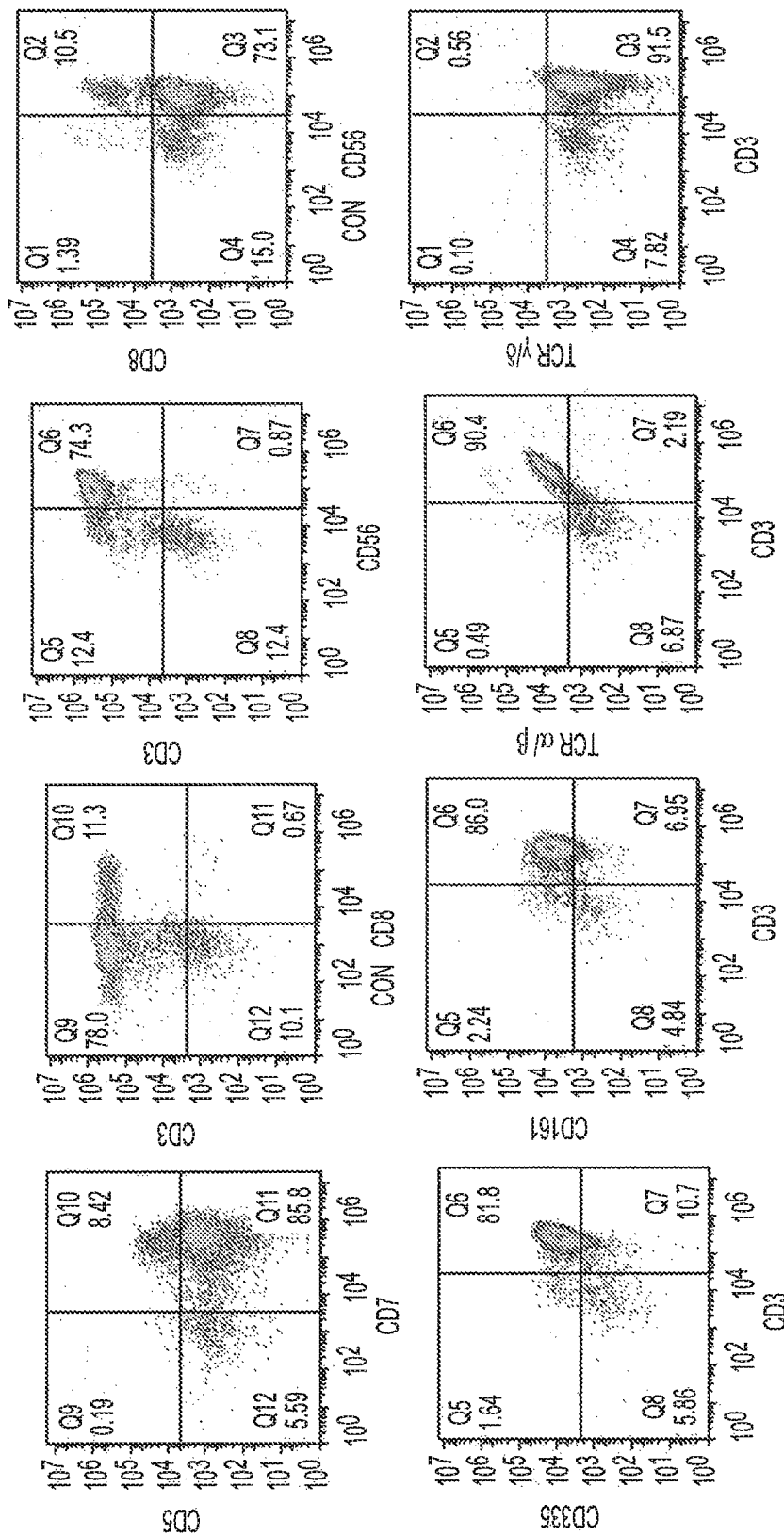
Figure 8A:
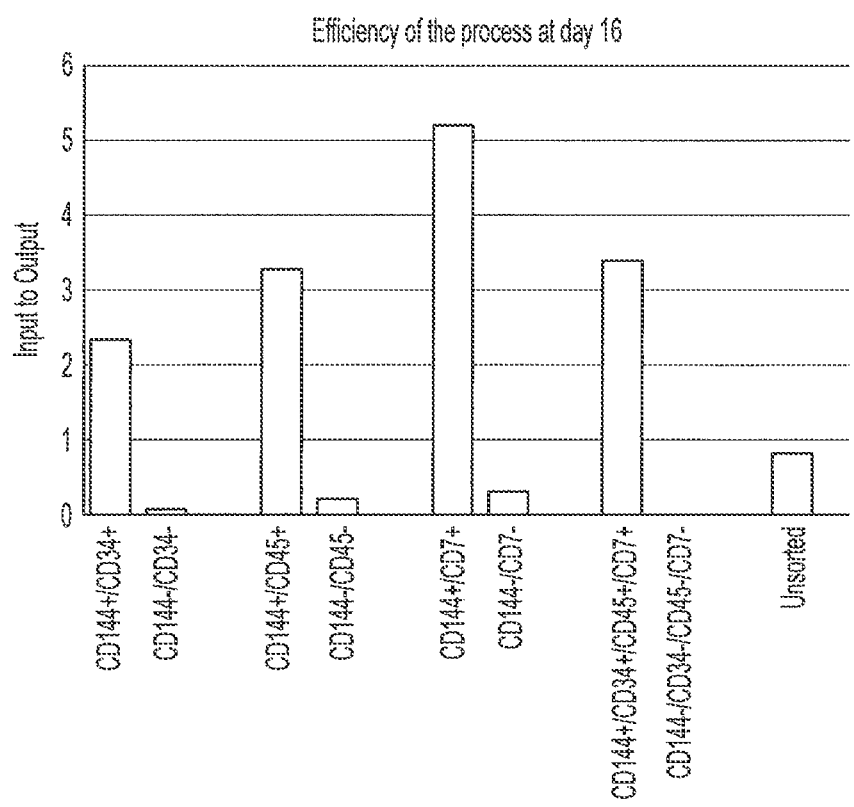
FIGS. 8A-8B: (A) Efficiency of TiPCs lymphoid differentiation process from HPCs at day 16 of both positive and negative magnetic sorted fractions is shown as the ratio of input HPCs to output lymphoid cells. (B) Cumulative efficiency of the differentiation process at the end of 4 weeks starting with the positive magnetic sorting fractions.
Figure 8B:
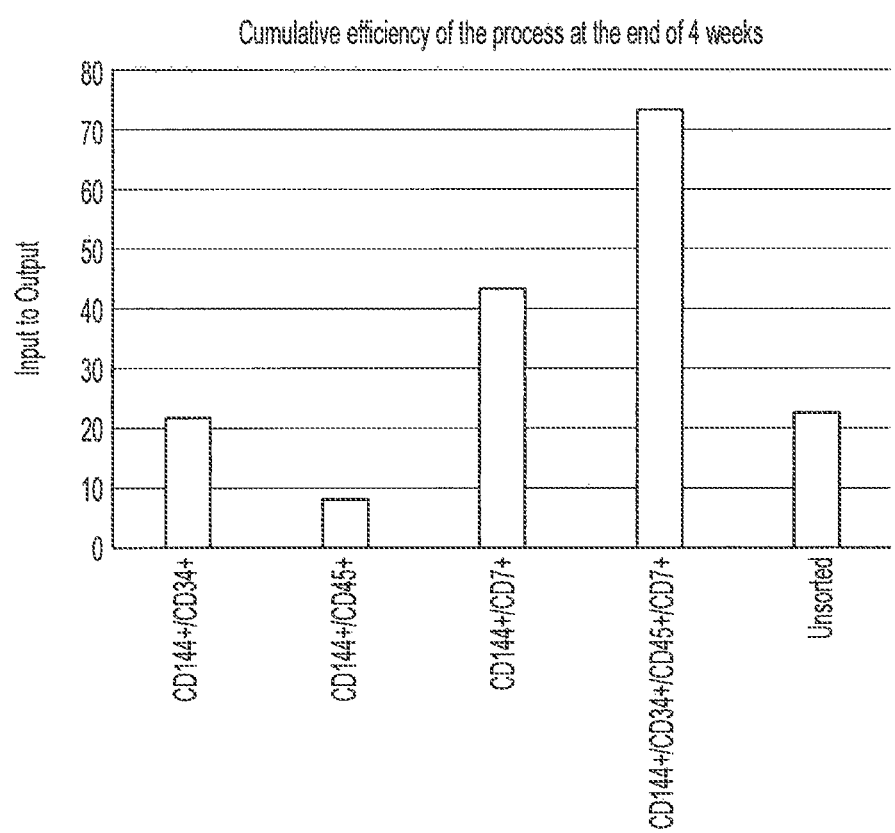

At 4 weeks of lymphoid differentiation, the Day 8 $CD144^+/CD7^+$ and the CD144+/CD45+ HPCs sustained generation of T cells in vitro as shown by the percentage of CD3 positive cells in FIG. 7A. The CD3 cells were CD335 positive, CD161 positive, and invariant T cell receptor (6B11) negative. Thus, the late state cultures have an emerging NK/T cell phenotype. In addition, the $CD144^+/CD7^+$ HPCs were shown to have an increased efficiency at producing T cells as measured by a ratio of input of HPCs to output of T cells at Day 16. However, the cumulative efficiency of the process at the end of 4 weeks was shown to be highest for the CD144/CD34/Cd45/CD7 positive fraction.

Example 5

Myeloid Differentiation of HPCs

The $CD34^+$ HPCs of Examples 2 and 3 were subjected to myeloid differentiation for the production of relatively pure populations of human dendritic cells (DCs). The cells were cultured on low attachment tissue culture plates or flasks for the entire process. The cells were resuspended in serum free media containing 50 ng/mL Flt-3 ligand (Flt-3L), 50 ng/mL of Stem Cell Factor (SCF), 50 ng/mL of Thrombopoeitin (TPO), 50 ng/mL Interleukin-3 (IL-3), and 50 ng/mL Interleukin-6 (IL-6) at a density of $0.5-1\times10^6$ cells/mL.

To begin the myeloid differentiation, the cells were seeded at a density between 0.25-0.5 million cells per mL in Myeloid Progenitor Media (Table 4) and expanded for about 2 weeks. The cells were monitored for viability and expression of $CD34^+/CD45^+/CD43^+$ at days 4 and 8. The $CD34^+$ population was observed to decline and there was an emergence of $CD45^+/CD43^+/CD31^+$ population within the cultures. The phenotype of the cultures at this stage was predominantly $CD43^+/CD45^+/CD31^+/CD34^{Lo}$.

TABLE 4

Myeloid Progenitor Media

| Component | Manufacturer | Catalog No. | Concentration |
|---|---|---|---|
| Serum free media* | | | |
| GlutaMAX | Gibco | 35050 | 1% |
| Pen/Strep | Gibco | 15140 | 1% |
| SCF | Peprotech | 300-07 | 50 ng/mL |
| IL-6 | Peprotech | 200-06 | 50 ng/mL |
| TPO | Peprotech | 300-18 | 50 ng/mL |
| IL-3 | Peprotech | 200-06 | 50 ng/mL |
| Flt-3L | Peprotech | 300-19 | 50 ng/ml |

*StemSpan ™ SFEM (Stem Cell Technologies, Cat. 09650), Stem Pro 34 (Invitrogen, Cat. 10639-011), or Stemline II (Sigma, Cat. S0192) can be used as a serum free media.

When the cells revealed more than 50% expression of $CD43^+/CD45^+/CD31^+/CD34^-$ cell surface markers, the cells were then placed in Myeloid Expansion Media (Table 5) for 8 days. The cells were fed with fresh media every other day. At the end of 8 days, the cultured cells had an enriched population of myeloid cells revealing 80-90% $CD43^+/CD45^+/CD31^+/CD34^-$. At the end of this myeloid expansion phase, the cell number, viability, and purity was determined.

TABLE 5

Myeloid Expansion Media

| Component | Manufacturer | Catalog No. | Concentration |
|---|---|---|---|
| Serum free media* | | | |
| GlutaMAX | Gibco | 35050 | 1% |
| GM-CSF | Peprotech | 300-03 | 100 ng/mL |

*StemSpan ™ SFEM (Stem Cell Technologies, Cat. 09650), Stem Pro 34 (Invitrogen, Cat. 10639-011) or Stemline II (Sigma, Cat. S0192) can be used as a serum free media.

Figure 9A:
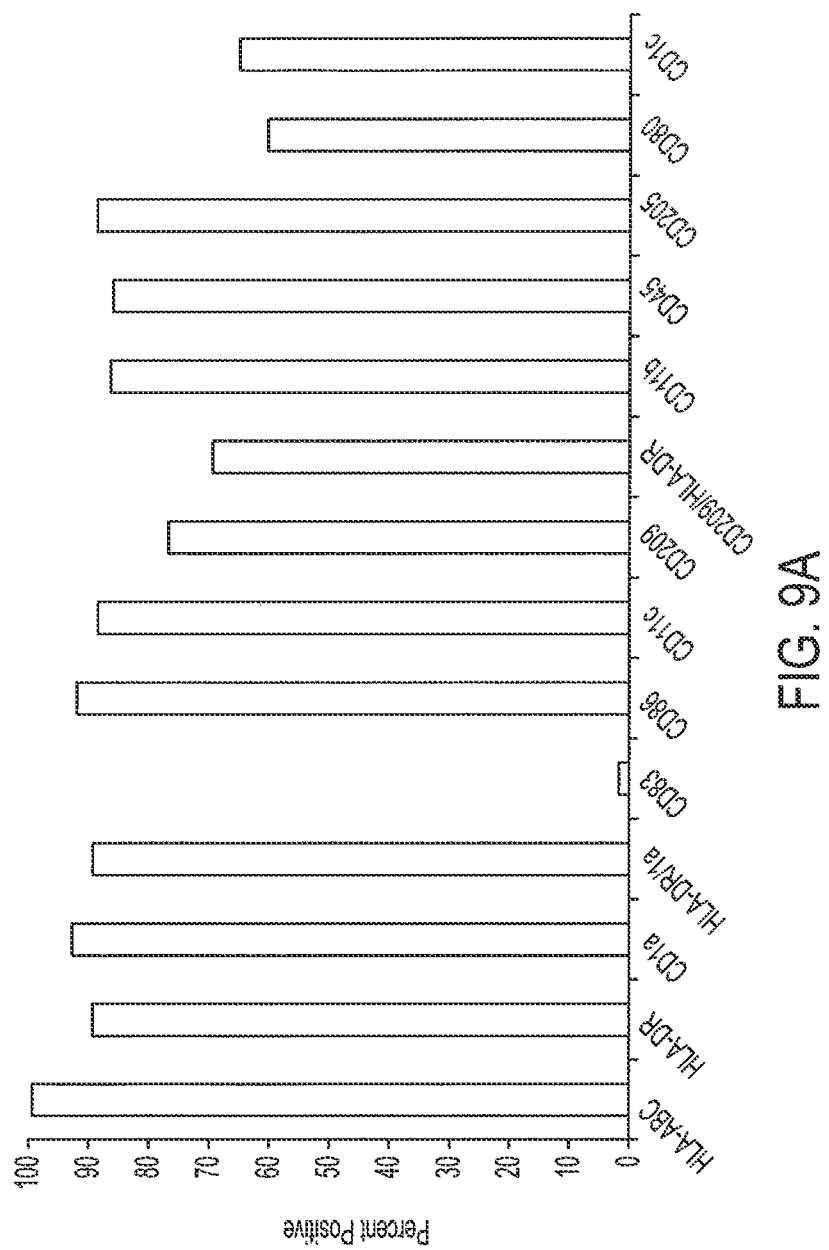
FIGS. 9A-9B: (A) Phenotypic analysis of dendritic cells derived from iPSC 02179 (MeCP2 WT) on day 42 of differentiation. The cells were stained for the cell surface expression of myeloid dendritic markers CD205, CD209, HLA-DR, CD1a, CD1c, CD80, CD11c, CD80, CD86 and CD83 (B) Representative FACS plot histograms for quantifying the expression of various cell surface markers expressed on dendritic cells.
Figure 9B:
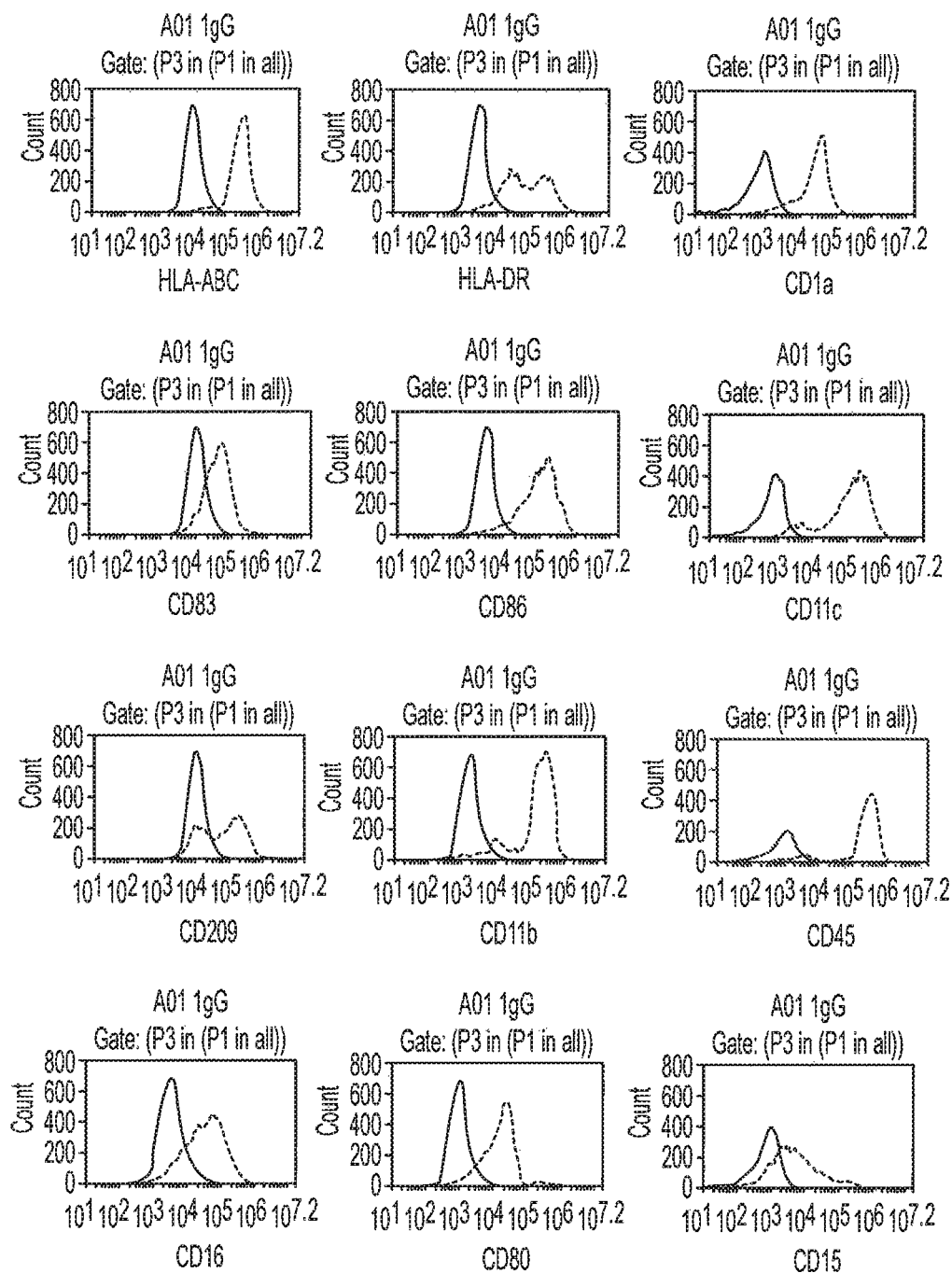
Figure 10:
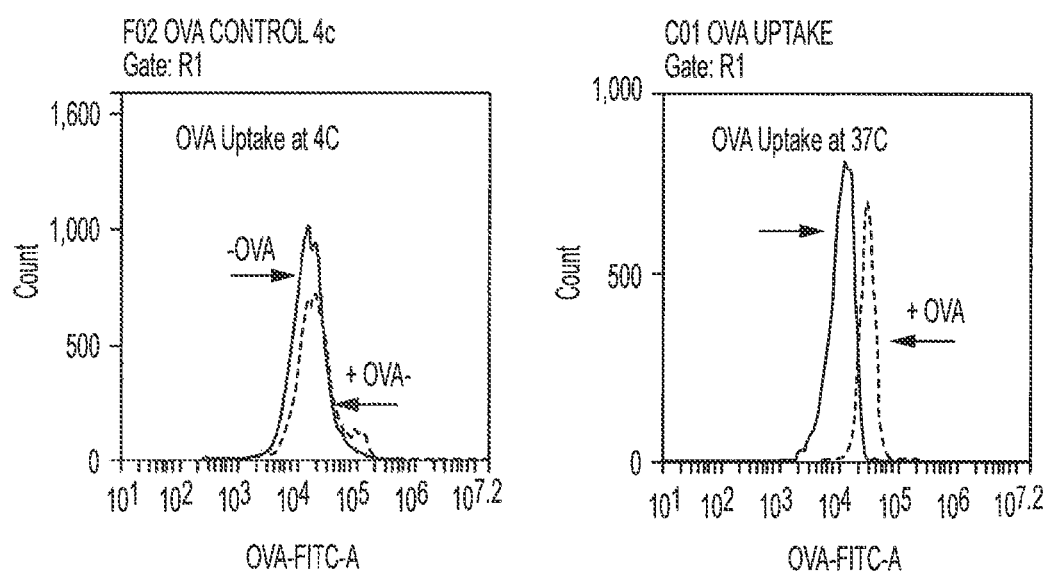
FIG. 10: DQ TM ovalbumin (DQ-OVA, Invitrogen) was dissolved at 1 mg/ml in PBS and added to iPSC derived DCs at 100 ug/ml. The cells were incubated either at 37° C. or at 4° C., washed twice with FACS buffer and analyzed on the Accuri flow cytometer. The specific uptake of OVA was demonstrated by iPSC derived DCs at 37° C. compared to the non-specific OVA uptake at 4° C.
Figure 11:
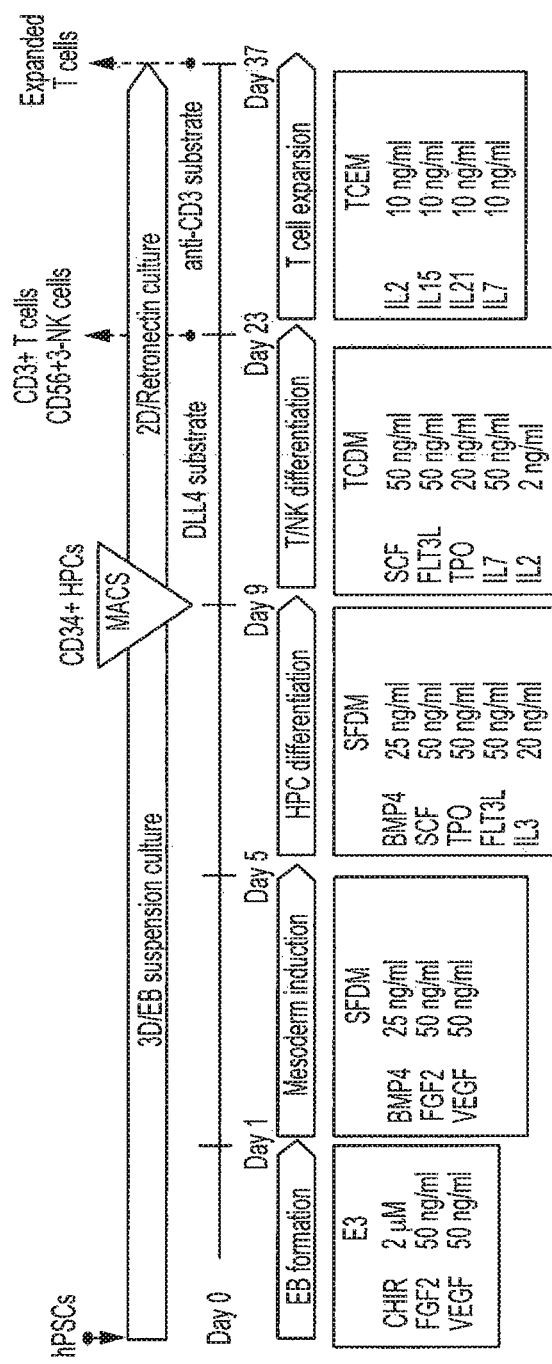
FIG. 11: Diagram representing feeder-free and serum-free T and NK cell differentiation of hPCS. PSCs were first differentiated to CD34+ hematopoietic progenitor cells (HPC) in suspension (3D) embryonic body (EB) culture through successive steps of aggregate formation, mesoderm induction and HPC differentiation during 9 days. CD34+ cells were isolated by MACS using direct CD34 paramagnetic beads (Miltenyi Biotec) and transferred to DLL4+ retronectin coated plates for T/NK differentiation during 2 weeks. T cells could further be expanded during 2 weeks in culture on anti-CD3 mAb (OKT3)+ retronectin coated (both at 0.5 μg/cm$^2$) plates in T-EM (ImmunoCult-XF T cell expansion medium (Stem Cell Technologies)) supplemented with IL2 alone or in combination with other T cell growth promoting cytokines (IL7, IL15, IL21). Abbreviations: SFDM, serum-free differentiation medium; TCDM, T cell differentiation medium; TCEM, T cell expansion medium; MACS, magnet-activated cell sorting.
Figure 12:
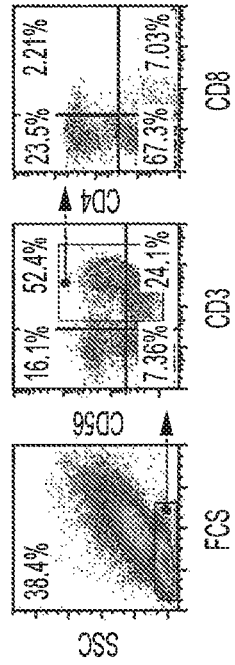
FIG. 12: Flow cytometric analysis of T/NK differentiation cultures. PSC (1C TiPSC)-derived CD34+ cells after 2 weeks in T/NK differentiation conditions develop a typical lymphoid cell population defined by low FSC/SSC parameters (left dot-plot). This lymphoid population contains mostly CD3+T and CD56+CD3− NK cells (middle dot-plot). T cell population includes CD4+ and CD8+ single and double positive cells as well as significant proportion of double negative cells (right dot plot).
Figure 13:
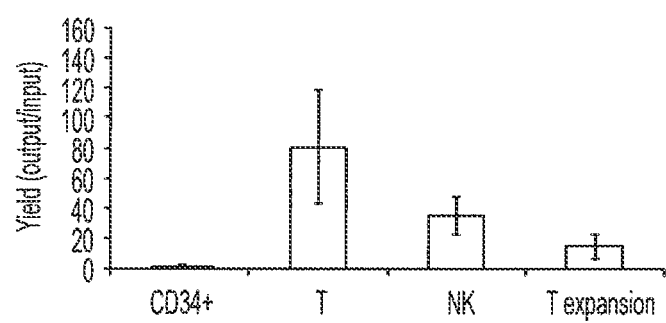
FIG. 13: The yield of different cell populations throughout differentiation. The yields of each respective cell type are expressed as a ratio of output to input absolute cell numbers at each stage of cell derivation depicted in the diagram. For example, 1.5 CD34+ cell yield indicates that in average 1.5 (output) CD34+ cells can be derived from 1 (input) PSC cell. Accordingly, 102 T cell yield indicates that 102 (output) T cells can be derived from 1 (input) CD34+ cells.
Figure 14:
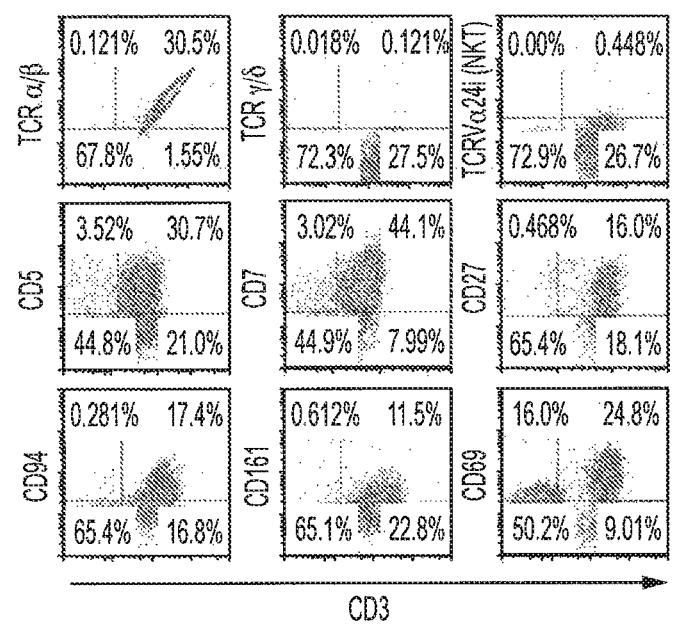
FIG. 14: Phenotype of PSC-derived T cells. PSC-derived T cells (CD3+) differentiated and expanded during 4 weeks express α/β TCR (not γ/δ or invariant Vα24 NKT TCR) and typical T cell markers CD5, CD27, CD7. They also express NK associated (CD161, CD94) and activation (CD69) markers.
Figure 15:
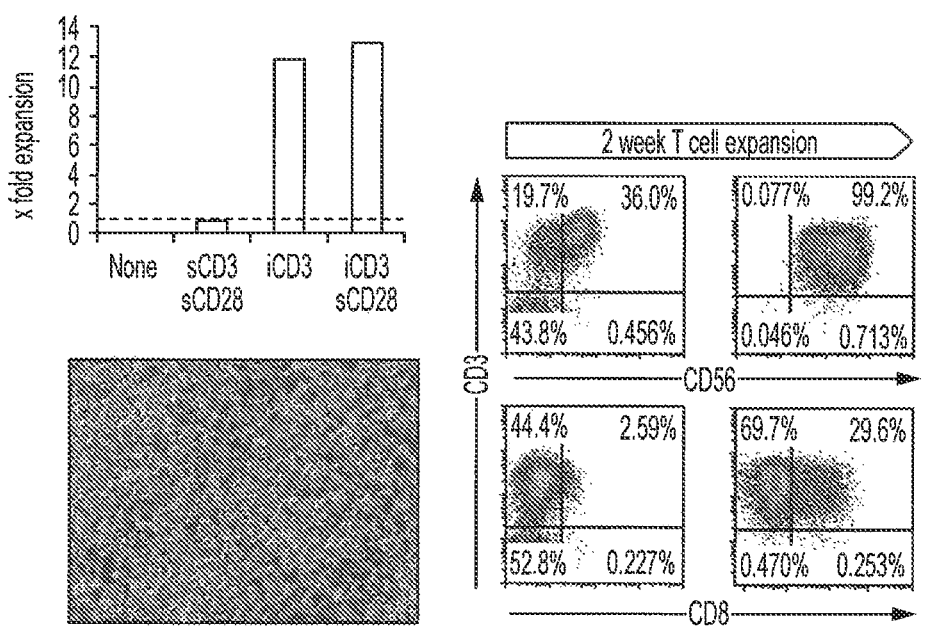
FIG. 15: Expansion of PSC-derived T cells. Immobilized anti-CD3 antibodies (iCD3) are minimally required and sufficient to achieve expansion of PSC-derived T cells (bar graph). Soluble stimulating CD3 and CD28 mAb (sCD3, sCD28) were not effective either alone (not shown) or in combination (sCD3+sCD28), or when added to iCD3 (iCD3+sCD28). T cells proliferating in the expansion cultures acquire a characteristic morphology of irregularly shaped lymphoblasts (photograph). In contrast to relatively heterogeneous input cell population, cells harvested from 2 week T cell expansion are essentially pure CD3+ T cells, which also express CD56 and acquire CD8 expression (flow cytometry dot plots).
Figure 16A:
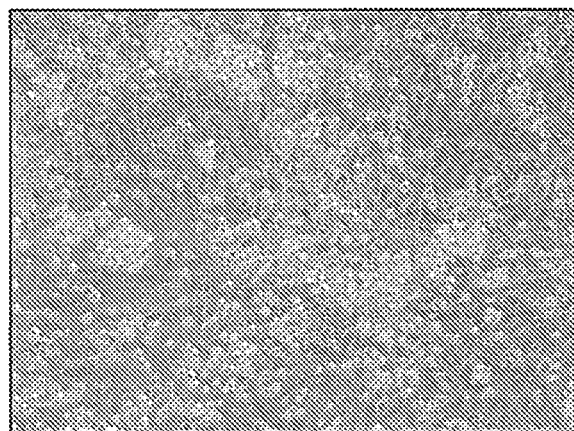
Figure 16B:
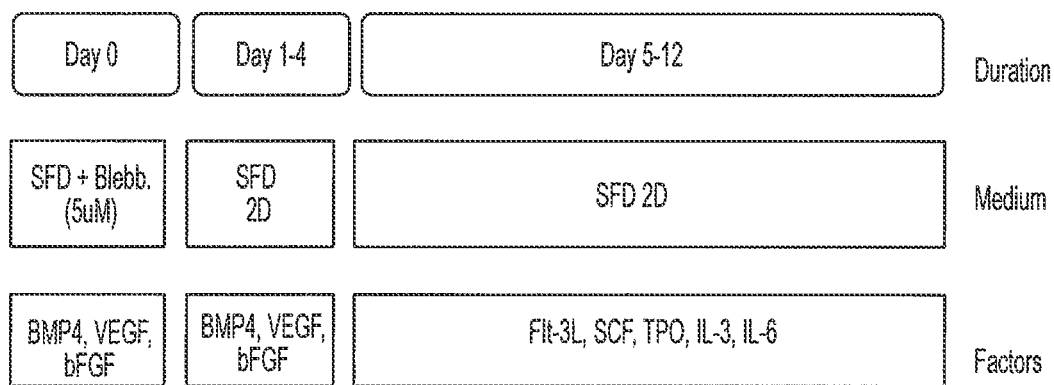
Figure 16C:
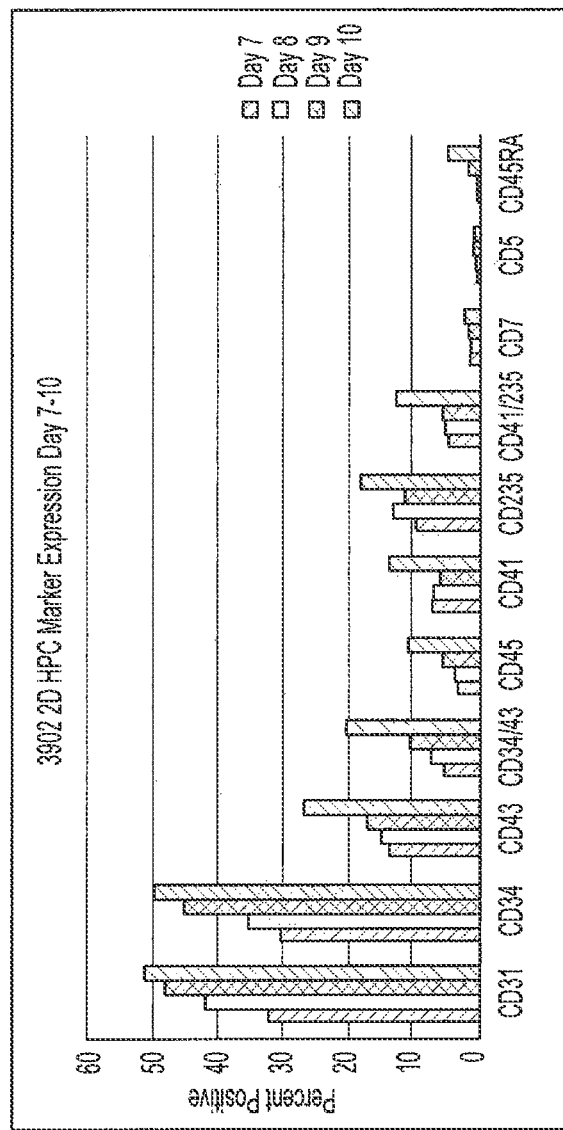
Figure 16D:
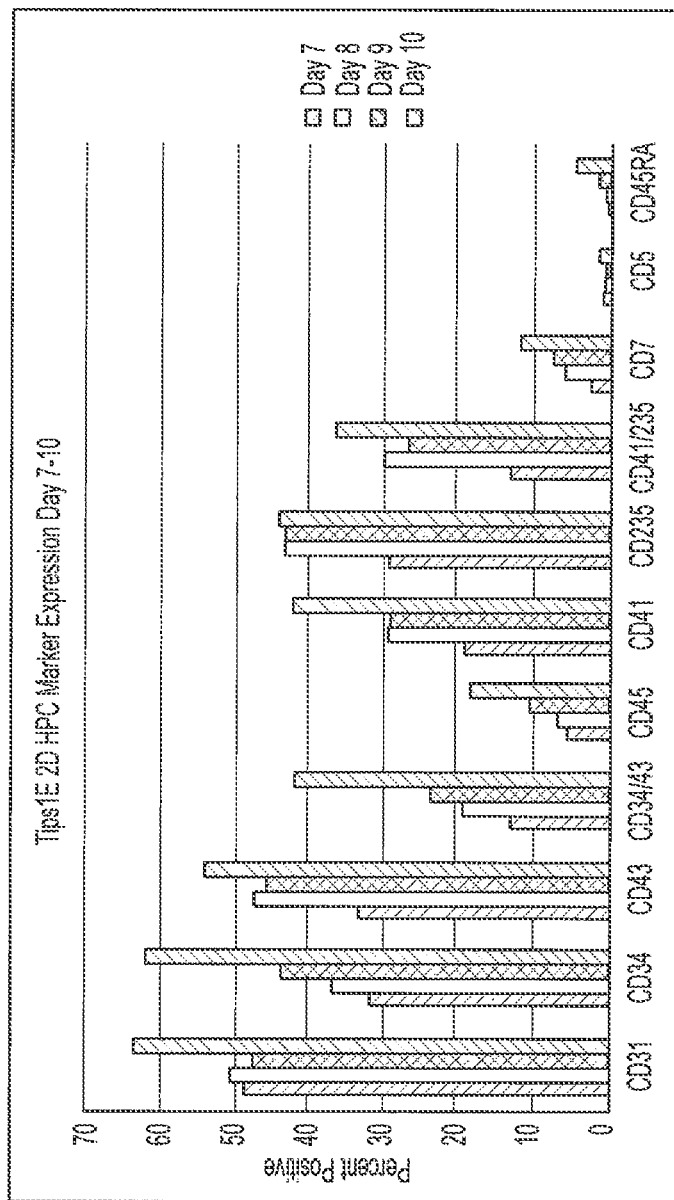
Figure 16F:
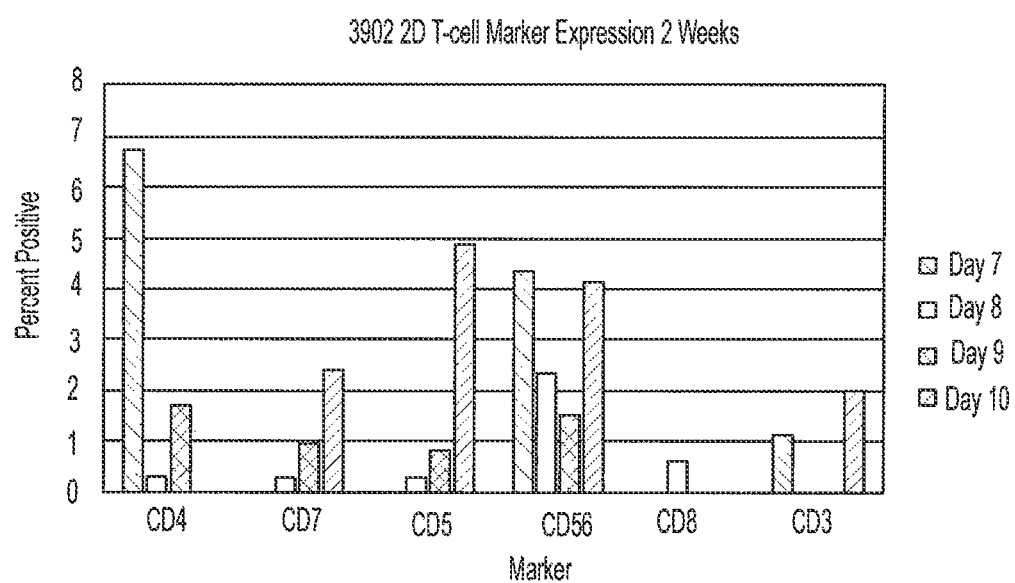
Figure 16G:
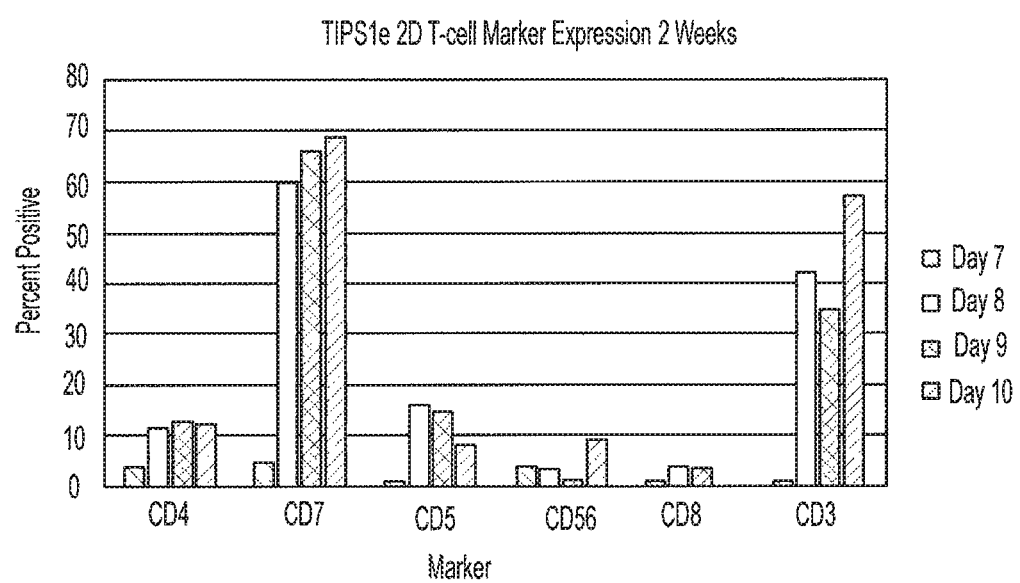

Finally, at the end of 16 days of culture, the cultures were placed in Dendritic Cell Enrichment Media (Table 6). The cell density was maintained between 0.5-1 million cells per mL, and the cells were fed with fresh media every four days without a spin step. There was almost no proliferation observed at this stage of differentiation. Instead, the cells were observed to stick to the low attachment plates and increase in size. At the end of one week, a sample was harvested and tested for the presence of $CD209^+$, $CD1a^+$, $HLA-DR^+$, CD11c+, $CD14^+$, $CD83^+$, and $CD86^+$ by flow cytometry (FIGS. 9-10). These markers predominantly stain myeloid DCs and not plasmocytoid DCs ($CD123^+$). The cells were maintained in Dendritic Cell Enrichment Media and analyzed at various time points to quantify the yield and purity. Wright staining was performed on cytospin samples to confirm the classic morphology of dendritic cells.

TABLE 6

Dendritic Cell Enrichment Media

| Component | Manufacturer | Catalog No. | Cocentration |
|---|---|---|---|
| Serum free media* | | | |
| GlutaMAX | Gibco | 35050 | 1% |
| GM-CSF | Peprotech | 300-03 | 100 ng/mL |
| Excyte | Millipore | 81-129-1 | 1% |
| IL-4 | Peprotech | 200-04 | 20 ng/mL |
| TNFα | Peprotech | 300-01A | 2.5 ng/mL |

Example 6

Methods of PSC Differentiation and T Cell Expansion

PSC Differentiation to CD34+ Lympho Hematopoietic Progenitors: The 1C T-cell derived iPSCs (TiPSC, derived by retroviral reprogramming) were differentiated to CD34+ hematopoietic progenitors through aggregate suspension (3D) culture. 1C cells were maintained under feeder-free conditions on Matrigel™- or Vitronectin-coated 6-well plates in Essential 8 (E8) medium. Aggregates were made from sub-confluent 1C cells (<80% confluence) at a density of 0.5-1 million cells per ml in the Essential 3 (E3) medium (containing only 3 of 8 components of E8 medium: DMEM/F12 basal medium, ascorbic acid 2-phosphate magnesium and sodium selenite) supplemented with, 50 ng/ml FGF2, 50 ng/ml VEGF, 2 µM CHIR99021 (GSK-3 inhibitor), and 10 µM blebbistatin (myosin-II inhibitor). The aggregate formation was performed during 24 hour culture in ultra-low attachment (ULA) flasks under continuous agitation on the rocker platform at 15 rpm (including all subsequent culture steps).

The formed cell aggregates (embryoid bodies—EBs) were further transferred to serum-free differentiation medium (50% IMDM, 50% Hams F12 medium, 100 µg/ml polyvinyl alcohol, 100 µg/ml recombinant human serum albumin, 1x non-essential amino acid supplement (Invitrogen), 0.1x chemically-defined lipid supplement (Invitrogen), 125 µM ascorbic acid 2-phosphate magnesium, 0.25 µM linoleic acid, trace element supplements A (0.3x), B (0.2x) and C (0.1x) (Corning), 5 mM sodium chloride, 100 µM monothioglycerol, 20 µM ethanolamine, 100 ng/ml heparin, and 10 ng/ml IGF1) supplemented with hematopoietic mesoderm inducing cytokines—25 ng/ml BMP4, 50 mg/ml VEGF and 50 ng/ml FGF2. Cultures were continued for 4 days with complete medium change on the second day.

To support differentiation and expansion of hematopoietic CD34+ progenitors, cell aggregates were further transferred to serum-free differentiation medium (as above) supplemented with hematopoietic supportive cytokines—50 ng/ml SCF, 20 mg/ml TPO, 10 ng/ml FLT3L, 20 ng/ml IL-3, and 25 ng/ml BMP4. Cultures were continued for 4 days with complete medium change on the second day.

The cultures were harvested after 1+4+4 (total 9 days) differentiation process. Single cell suspension was obtained through digestion of differentiated cell aggregates in the Accutase (or Accumax) solution for 15-20 min at 37 C. Cells were washed in MACS buffer (PBS containing 5 mg/ml BSA and 1 mM EDTA), filtrated through 70 µM cell strainers and labeled with direct CD34 paramagnetic microbeads (Myltenyi Biotec) 30 min at 4 C. CD34+ cells were isolated using MS or LS magnetic columns, appropriate magnets and standard separation procedures according to recommendations from manufacturer (Myltenyi Biotech). Isolated CD34+ cells were plated to T/NK differentiation cultures or cryopreserved for later use within 1 hour after isolation.

T/NK Differentiation Cultures: For T/NK differentiation, non-tissue culture treated plastic plates were coated with Notch ligand hDLL4-Fc chimeric protein and retronectin diluted in PBS (at 0.5 µg/cm$^2$ each). Before cell plating, coating solution was aspirated, plates washed once with cell culture basal medium (DMEM/F12 or other), and filled with 0.25 ml/cm$^2$ T cell differentiation medium (TCDM) consisting of StemSpan SFEM (Stem Cell Technologies), GlumaMax (1/100), PenStrep (1/200), ascorbic acid magnesium phosphate (250 µM), nicotinamide (2 mM) and cytokines SCF, TPO, FLT3L and IL7 (at 50 ng/ml each). Isolated PSC-derived CD34+ cells were plated at 5000 cells/cm$^2$ density and cultured in hypoxic (5% 02) $CO_2$ incubator for 2 weeks with addition of fresh TCDM culture volume on day 3 and day 6, and exchanging a half culture volume every third following day. Total differentiated cells were harvested by gentle resuspension and collection of non-adherent cells followed by detachment of adherent cells by 10-15 min treatment with PBS-EDTA (0.5 mM).

T Cell Expansion Cultures: For T cell expansion, tissue culture plastic plates were coated with anti-CD3 mAb (clone OKT3) and retronectin diluted in PBS (at 0.5 µg/cm$^2$ each). Before cell plating, coating solution was aspirated, plates washed twice with cell culture basal medium (DMEM/F12 or other), and filled with 0.2 ml/cm$^2$ T cell expansion medium (TCEM) consisting of ImmunoCult XF medium (Stem Cell Technologies), GlumaMax (1/100), PenStrep (1/200), and cytokines IL2 and IL7 (at 10 ng/ml each). IL15 and/or IL21 could also be added to improve expansion. Cells harvested from T/NK differentiation cultures were plated at 20000 cells/cm$^2$ density and cultured in hypoxic (5% 02) $CO_2$ incubator for 2 weeks with addition of fresh TCEM culture volume on day 3 and exchanging a half culture volume every third following day. Expanded T cells were harvested by gentle resuspension and collection of non-adherent cells.

Example 7

2D Protocol for Production of HPCs 01279.107.3902 MeCP2 knockout and TiPSCs1E cells were subjected to the 2D differentiation protocol for the production of HPCs (FIG. 16). First, the iPSCs were acclimatized to hypoxic conditions for 5-10 passages under feeder-free conditions on Matrigel™- or Vitronectin-coated in Essential 8 (E8) media. iPSCs were individualized and plated on PureCoat Amine-coated 6-well plates (Corning Inc.) at a density of 25000/cm$^2$ in the presence Serum Free Defined (SFD) media supplemented with 5 uM blebbistatin. The SFD basal medium contained 75% IMDM (Invitrogen 12200-069) (with Glutamine and 25 mM HEPES+P/S), 25% Hams F12 (Mediatech 10-080-CV), 0.5% N2-supplement (Invitrogen 17502-048), 1% B27 supplement without retinoic acid (Invitrogen 12587-010), 0.05% BSA, 50 ug/ml Ascorbic acid, and 4.5×10-4 M monothioglycerol supplemented with 50 ng/ml of BMP-4, VEGF, and bFGF.

Induction of hematopoietic differentiation was initiated on Day 1 by culturing in SFD basal medium containing 75% IMDM (Invitrogen 12200-069) (with Glutamine and 25 mM HEPES+P/S), 25% Hams F12 (Mediatech 10-080-CV), 0.5% N2-supplement (Invitrogen 17502-048), 1% B27 supplement without retinoic acid (Invitrogen 12587-010), 0.05% BSA, 50 ug/ml Ascorbic acid, and 4.5×10-4 M monothioglycerol supplemented with 50 ng/ml of BMP-4, VEGF, and bFGF. On Day 2, the media was aspirated and the cells were placed in fresh EB1 medium. (SFD basal medium containing 75% IMDM (Invitrogen 12200-069) (with Glutamine and 25 mM HEPES+P/S), 25% Hams F12 (Mediatech 10-080-CV), 0.5% N2-supplement (Invitrogen 17502-048), 1% B27 supplement without retinoic acid (Invitrogen 12587-010), 0.05% BSA, 50 ug/ml Ascorbic acid, and 4.5×10-4 M monothioglycerol supplemented with 50 ng/ml of BMP-4, VEGF, and bFGF) for an additional 48 hrs.

On Days 5-10, the media was aspirated and the cells were placed in EB2 media for the next 48 hrs. The EB2 media comprised fresh SFD basal medium containing 75% IMDM (Invitrogen 12200-069) (with Glutamine and 25 mM HEPES+P/S), 25% Hams F12 (Mediatech 10-080-CV), 0.5% N2-supplement (Invitrogen 17502-048), 1% B27 supplement without retinoic acid (Invitrogen 12587-010), 0.05% BSA, 50 ug/ml Ascorbic acid, and 4.5×10-4 M monothioglycerol supplemented with 50 ng/ml of Flt-3 Ligand, IL3, IL6, SCF, and TPO each at 50 ng/ml and 5000 U/ml of heparin. The cells were harvested at day 7, 8, 9, 10 of differentiation using TrypLE and stained for the presence of HPC markers and lymphoid progenitors.

For T cell differentiation, the HPCs were plated on non-treated tissue culture plates coated with Retronectin and Notch DLL4 at 0.5 μg/cm$^2$ at a cell density of about 5,000 to about 25,000 cells/cm$^2$. The HPCs were cultured in StemSpan Serum-Free Expansion Medium II (SFEM; StemCell Technologies) media or SFD supplemented with 1% Glutamax, 1% Penicillin Streptomycin, 95 μM Ascorbic acid (WAKO labs), as well as 50 ng/mL of IL-7, SCF, Flt-3, and TPO (Peprotech). The media was replenished every 48 hours and at 2 weeks the cells were split non-enzymatically to new ligand coated plates. In addition, between 2 and 3 weeks the cells were analyzed for the presence of pre-T cells by the cell surface markers CD5 and CD7. At 4 weeks, the cells were analyzed for the presence of T cells by the cell surface markers CD3, CD4 and CD8. At 6-8 weeks, the cells were analyzed for the presence of T and NK cells using the cell surface markers CD4, CD8, CD3, CD94 and CD56.

Example 8

Effect of MeCP2 Disruption on Lymphoid Differentiation

To determine the role of MeCP2 in the hematopoietic differentiation process, a MeCP2 knockout iPSC cell line was generated. The male wildtype (WT) 01279 iPSC cell line was engineered to knockout MeCP2 to create the MyCell® 01279.107.3902 cell line. Using TAL nuclease, a series of stop codons were inserted prior to the methyl CpG binding domain (FIG. 17B) of MeCP2 by transfection of MeCP2 TALENs and the donor plasmid containing the stop codon insertion was followed by insertion of LoxP flanked, PGKp-Puromycin-SV40 pA in the reverse orientation. The 0.1279 iPSCs were transfected with MeCP2 TALENS and Donor plasmid p1553 expressing wild-type EBNA1.

The cells positive for insertion were selected for with puromycin selection, and colonies were then picked and screened by integration PCR. Of the screened colonies, 96% were positive for insertion by two PCR screening reactions. Fourteen of the clones were expanded and screened at passage 3, and eight of the clones were found to be negative for the integration of the backbone plasmid. Thus, three of the remaining clones were sequenced through the insert and two were found to be polyclonal. The one monoclonal line 0.1279.107.302 was selected and fully characterized for further studies. Additional clones were also obtained and characterized as correctly engineered. The amino acid alignment of MeCP2 variants 001, 002, 005 and 008 is depicted in FIG. 17C. The variant 008 does not code for a MethylCpG binding domain.

Figure 17A:
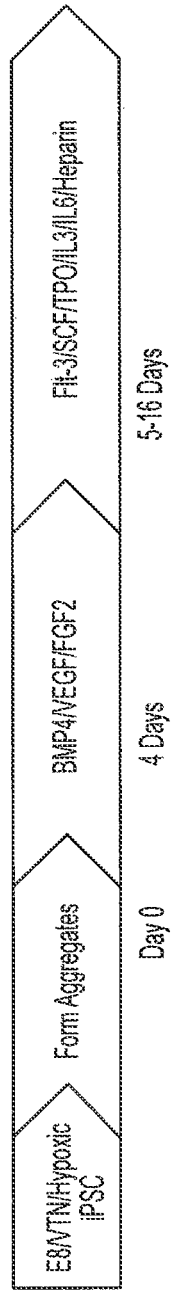
Figure 17B:
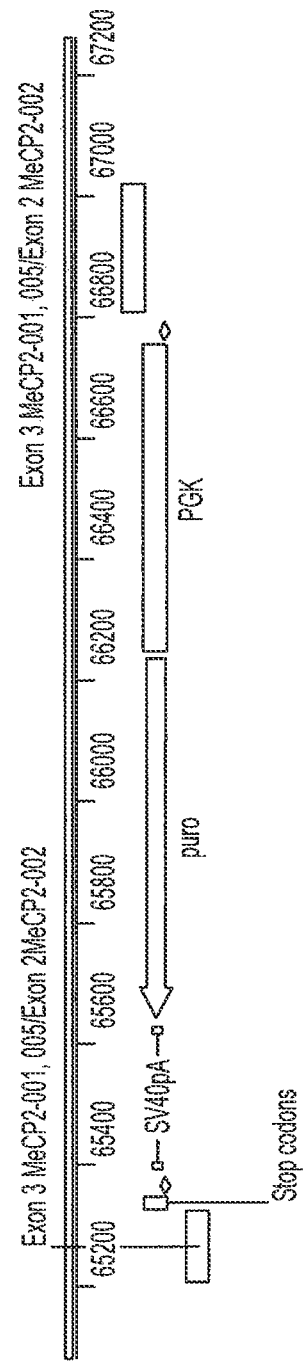

The 01279.107.3902 MeCP2 knockout cells of Example 1 and WT 01279 cells were subjected to the 3D differentiation protocol for the production of HPCs (FIG. 17A). First, the iPSCs were acclimatized to hypoxic conditions for 5-10 passages under feeder-free conditions on Matrigel™- or Vitronectin-coated in Essential 8 (E8) media. Aggregates were made from sub confluent iPSCs at a density of 0.25-0.5 million cells per ml in the presence Serum Free Defined (SFD) media supplemented with 5 uM blebbistatin. The process was performed in ultra-low attachment (ULA) plates or spinner flasks in SFD basal medium containing 75% IMDM (Invitrogen 12200-069) (with Glutamine and 25 mM HEPES+P/S), 25% Hams F12 (Mediatech 10-080-CV), 0.5% N2-supplement (Invitrogen 17502-048), 1% B27 supplement without retinoic acid (Invitrogen 12587-010), 0.05% BSA, 50 ug/ml Ascorbic acid, GlutaMAX, Pen/Strep and 4.5×10$^{-4}$ M monothioglycerol.

Once the embryoid bodies (EBs) had formed, differentiation was initiated by supplementing the SFD basal media with 50 ng/ml of BMP-4, VEGF, and bFGF for the first 4 days. On the fifth day, the EB cultures were placed in the presence of Flt-3 Ligand, IL3, IL6, SCF, heparin, and TPO each at 50 ng/ml. The EB cultures were supplemented with half the volume of fresh differentiation media containing cytokines every 2 days during the differentiation process until day 12-16 of differentiation under hypoxic conditions.

For lymphoid differentiation, the HPCs were plated on non-treated tissue culture plates coated with Retronectin and Notch DLL4 at 0.5 μg/cm$^2$ at a cell density of about 5,000 to about 25,000 cells/cm$^2$. The HPCs were cultured in StemSpan Serum-Free Expansion Medium II (SFEM; StemCell Technologies) media supplemented with 1% Glutamax, 1% Penicillin Streptomycin, 95 μM Ascorbic acid (WAKO labs), as well as 50 ng/mL of IL-7, SCF, Flt-3, and TPO (Peprotech). The media was replenished every 48 hours and at 2 weeks the cells were split non-enzymatically to new ligand coated plates. In addition, between 2 and 3 weeks the cells were analyzed for the presence of pre-T cells by the cell surface markers CD5 and CD7. At 4 weeks, the cells were analyzed for the presence of T cells by the cell surface markers CD3, CD4 and CD8. At 6-8 weeks, the cells were analyzed for the presence of T and NK cells using the cell surface markers CD4, CD8, CD3, CD94 and CD56.

Figure 19A:
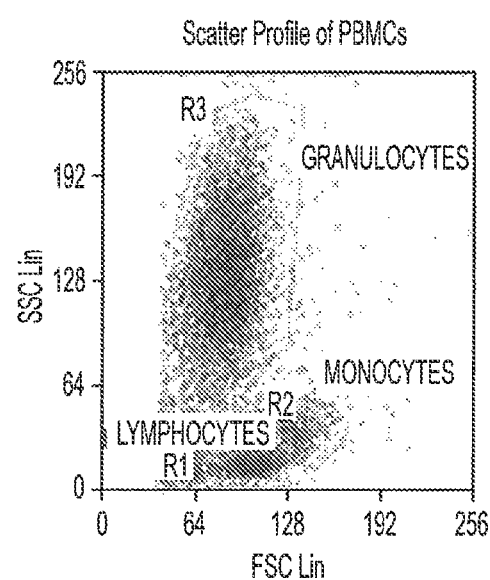
Figure 20:
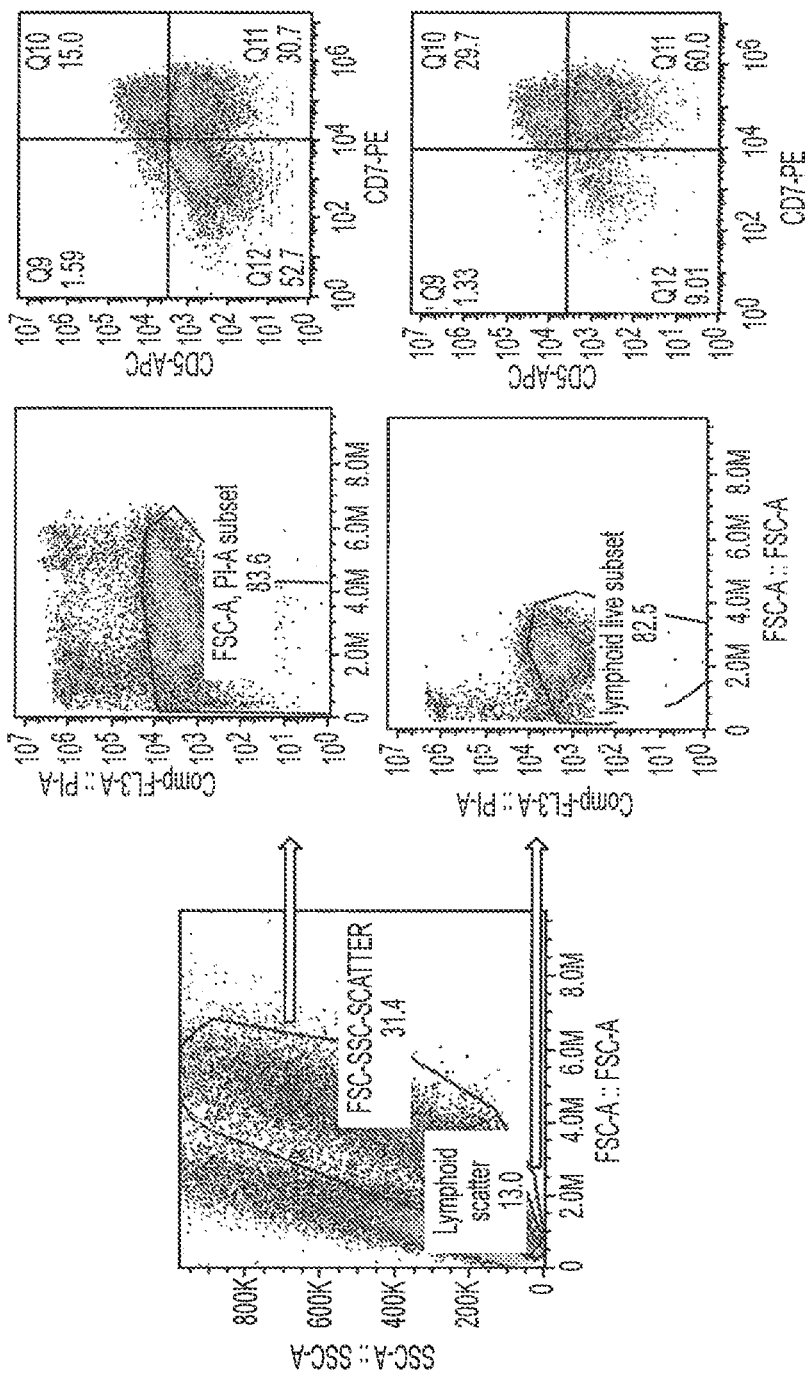
FIG. 20: Gating strategy for identifying lymphoid cells generated in vitro. A scatter profile of lymphoid cells at day 18 of differentiation is shown. The FSC-SSC gate and the lymphoid gate are illustrated. Live cells were gated within the FSC-SSC scatter and lymphoid scatter using propidium iodide followed by staining for CD7 and CD5 positive cells by flow cytometry.

The efficiency of the MeCP2 knockout clones at differentiating to lymphoid lineages was analyzed by harvesting the 01279.107.3902, 01279.107.3905, 01279.107.3906, 01279.107.3907, and 01279.107.3908 clones at day 5, day 7, day 9 and day 11 of the HPC differentiation. The HPC cells were thawed having been cryopreserved at the time point previously described and plated on Retronectin and DLL4 coated plates. The cells were fed with fresh media every 2 days and were analyzed for pre-T cell markers at 2 weeks (FIG. 18A, 18B), T and NK cell markers at 4 weeks after the HPC cells were thawed. In the analysis of the pre-T cell markers, all of the cells except for the wild-type 01279.107.0904 cells had the presence of pre-T cells identified as CD5$^+$CD7$^+$, CD7$^+$CD45$^+$ and CD5$^+$CD45$^+$. The cells were stained for the surface expression of CD45, CD7, and CD5 (FIG. 19) and CD56, CD8, and CD3 (FIG. 20), and the presence of T, NK and NK/T cells were quantified.

Figure 21A:
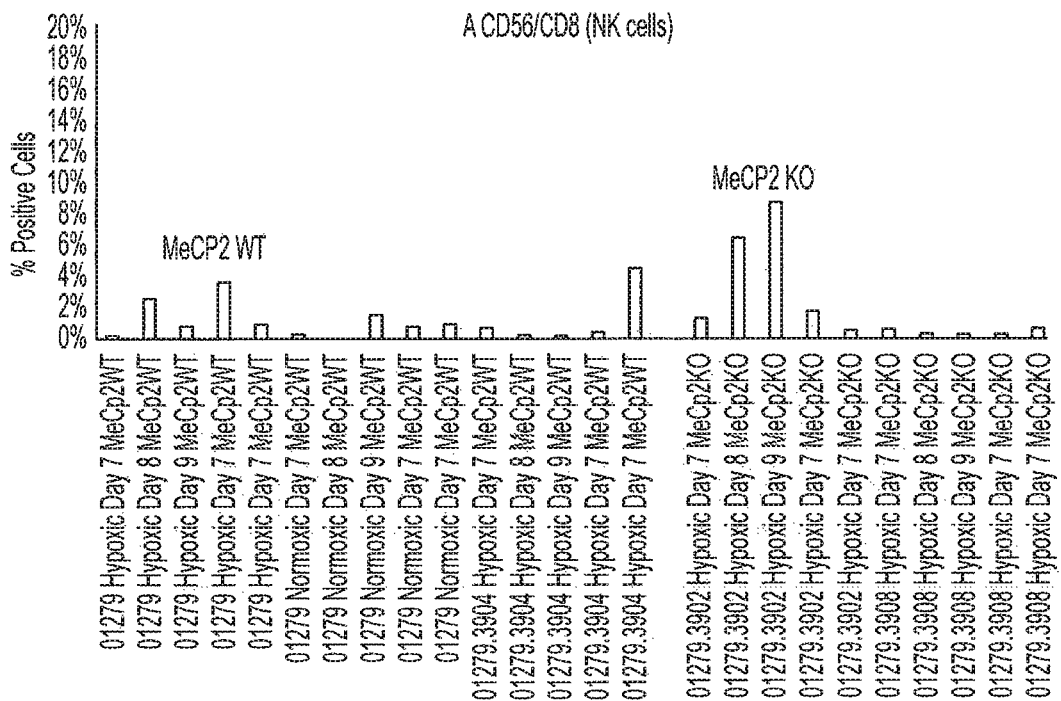
FIGS. 21A-21B: Quantification of NK (CD3−/CD56+) cells on day 7-11 of HPC of differentiation and placed on Ret-DLL4 coated plates to initiate lymphoid differentiation at a density of 2.5×10⁴/cm². The percentages of double positive, CD56+/CD3− under the all live FSC-SSC gate (A) and lymphoid gate (B) was determined for iPSC clones containing MeCp2 WT and MeCp2KO status.
Figure 21B:
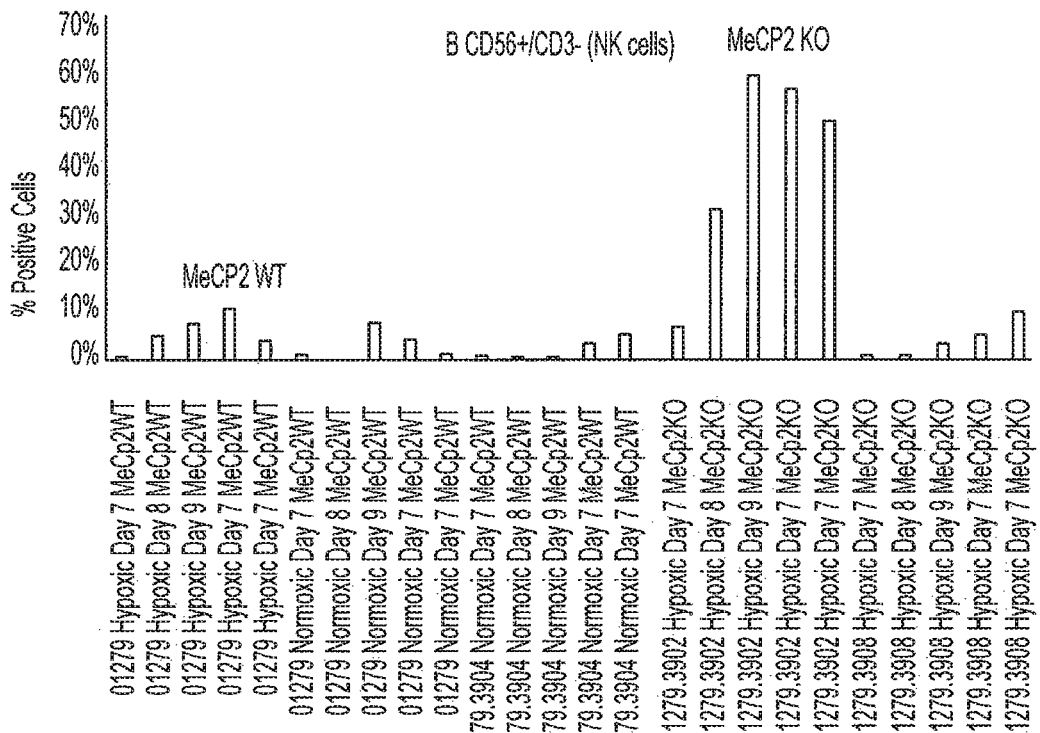

Since the input number of cells was known the absolute number of T (CD3$^+$/CD8$^+$), NK (CD3$^-$/CD56$^+$) and NK/T cells (CD3$^+$/CD56$^+$) was determined. The efficiency of the process is calculated by the ratio of absolute number of a cell type (T, NK, or NK/T)/input number of total cells or by the ratio of absolute number of a cell type/input number of HPCs. The percentage of T cells (CD3$^+$/CD8$^+$) (FIG. 17) and the percentage of NK cells (CD3$^-$/CD56$^+$) (FIG. 21) were quantified by flow cytometry under FSC-SSC gate and the lymphoid scatter gate. The quantity of emerging NK/T (CD3$^+$/CD56$^+$), (CD3$^+$/CD8$^+$), NK/T (CD3$^+$/CD56$^+$) and NK (CD3$^-$/CD56$^+$) cells were also determined. Further analysis showed that the expression of CD235/CD7, CD144$^+$/Dll4$^+$, and Flk-1$^+$/CD34$^+$ declines at day 11 of differentiation. Since there is an absence of lymphoid cells at day 11 of differentiation, this may imply that a certain threshold level of expression of these markers is essential to prime cells towards lymphoid differentiation in the presence of DLL4.

Analysis of the T cell markers showed that the MeCP2 KO cell lines, but not the MeCP2 WT cell line, had the potential for lymphoid differentiation. The Day 9 HPC progenitors from the MeCP2 WT cells had essentially no CD3$^+$CD8$^+$ T cells while the other HPC progenitors tested differentiated to a population of CD3$^+$CD8$^+$ T cells. Thus, the knockout of the methyl binding domain of MeCP2 enhanced the potential of the HPC progenitors to produce T and NK cells.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abboud et al., *Blood*, 58:1148-1154, 1981.
Akkina et al., *J. Virol.*, 70:2581-2585, 1996.
Alexander et al., *Proc. Nat. Acad. Sci. USA*, 85:5092-5096, 1988.
Ausubel et al., *Current Protocols in Molecular Biology*, Greene Publ. Assoc. Inc. & John Wiley & Sons, Inc., MA, 1996.
Biswas et al., *Annals NY Acad Sci.*, 590:582-583, 1990.
Biswas, et al., *J. Clin. Microbiol.*, 29:2228-2233, 1991.
Blomer et al., *J. Virol.*, 71(9):6641-6649, 1997.
Chen and Okayama, *Mol. Cell Biol.*, 7(8):2745-2752, 1987.
Doulatov et al., *Cell Stem Cell*. 10:120-36, 2012.
Ercolani et al. *J. Biol. Chem.*, 263:15335-15341, 1988.
Evans, et al., In: Cancer *Principles and Practice of Oncology*, Devita et al. (Eds.), Lippincot-Raven, NY, 1054-1087, 1997.
Fauser et al., *Stem Cells*, 1:73-80, 1981
Fechheimer et al., *Proc Natl. Acad. Sci. USA*, 84:8463-8467, 1987.
Fraley et al., *Proc. Natl. Acad. Sci. USA*, 76:3348-3352, 1979.
Frisan et al., Epstein-Barr Virus Protocols, Part III, 125-127, 2001
Furie and Furie, *Cell* 53: 505-518, 1988.
Golde et al., *Proc. Natl. Acad. Sci. USA*, 77:593-596, 1980.
Graham and Van Der Eb, *Virology*, 52:456-467, 1973.
Haddada et al., in *Current Topics in Microbiology and Immunology*, 1995.
International Publication No. WO 94/09699
International Publication No. WO 95/06128
International Publication No. WO 96/39487
Jaenisch, *Science* 240:1468-1474, 1988.
Kaeppler et al., *Plant Cell Reports* 9: 415-418, 1990.
Karin et al. *Cell*, 36:371-379, 1989.
Kato et al, *J. Biol. Chem.*, 266:3361-3364, 1991.
Kim et al., *J. Virol.*, 66:3879-3882, 1992.
Knust et al, *EMBO J*. 761-766, 1987.
Ladi et al., *Nature Immunology*, 7: 338-343, 2006.
Langle-Rouault et al., *J. Virol.*, 72(7):6181-6185, 1998.
Levitskaya et al., *Proc. Natl. Acad. Sci. USA*, 94(23):12616-12621, 1997.
Lusis, *Blood*, 57:13-21, 1981.
Macejak and Sarnow, *Nature*, 353:90-94, 1991.
Maniatis, et al., Molecular Cloning, A Laboratory Manual, Cold Spring Harbor Press, Cold Spring Harbor, N.Y., 1988.
Mann et al., *Cell*, 33:153-159, 1983.
Minskaia and Ryan, 2013
Nabel et al., *Science*, 244(4910):1342-1344, 1989.
Naldini et al., *Science*, 272(5259):263-267, 1996. Zufferey et al., *Nat. Biotechnol.*, 15(9):871-875, 1997.
Ng, *Nuc. Acid Res.*, 17:601-615, 1989.
Nicola, et al., *Blood*, 54:614-627, 1979.
Nicolas and Rubenstein, In: *Vectors: A survey of molecular cloning vectors and their uses*, Rodriguez and Denhardt, eds., Stoneham: Butterworth, pp. 494-513, 1988.
Nicolau and Sene, *Biochim. Biophys. Acta*, 721:185-190, 1982.
Nicolau et al., *Methods Enzymol.*, 149:157-176, 1987.
Notta et al., *Science*, 218-221, 2011.
Okabe, *J. Cell. Phys.*, 110:43-49, 1982.
Paskind et al., *Virology*, 67:242-248, 1975.
Patent Publication No. EP1507865
Pelletier and Sonenberg, *Nature*, 334(6180):320-325, 1988.
Potrykus et al., *Mol. Gen. Genet.*, 199(2):169-177, 1985.
Potter et al., *Proc. Natl. Acad. Sci. USA*, 81:7161-7165, 1984.
Quitsche et al., *J. Biol. Chem.*, 264:9539-9545, 1989.
Richards et al., *Cell*, 37:263-272, 1984.
Rippe, et al., *Mol. Cell Biol.*, 10:689-695, 1990.
Sambrook and Russell, *Molecular Cloning: A Laboratory Manual*, 3rd Ed. Cold Spring Harbor Lab. Press, 2001.
Suzuki et al, EMBO J. 6:1891-1897, 1987.
Temin, In: *Gene Transfer*, Kucherlapati (Ed.), NY, Plenum Press, 149-188, 1986.
Tur-Kaspa et al., *Mol. Cell Biol.*, 6:716-718, 1986.
U.S. patent application Ser. No. 12/715,136
U.S. patent application Ser. No. 08/464,599
U.S. Patent Application No. 61/088,054
U.S. Pat. No. 4,683,202
U.S. Pat. No. 5,030,015
U.S. Pat. No. 5,302,523
U.S. Pat. No. 5,322,783

U.S. Pat. No. 5,384,253
U.S. Pat. No. 5,464,765
U.S. Pat. No. 5,486,359
U.S. Pat. No. 5,538,877
U.S. Pat. No. 5,538,880
U.S. Pat. No. 5,550,318
U.S. Pat. No. 5,556,954
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,928,906
U.S. Pat. No. 5,945,100
U.S. Pat. No. 5,981,274
U.S. Pat. No. 5,994,136
U.S. Pat. No. 5,994,624
U.S. Pat. No. 6,013,516
U.S. Pat. No. 8,372,642
U.S. Patent Publication No. 20020055144
U.S. Patent Publication No. 20090148425
Wilson et al., *Nature Reviews Immunology*, 9: 91-105, 2009.
Wilson et al., *Science*, 244:1344-1346, 1989.
Wong et al., *Gene*, 10:87-94, 1980. Kaneda et al., *Science*, 243:375-378, 1989.
Wynn, *Nature Immunology*, 6:1069-1070, 2005.
Yamanaka et al., *Cell*, 131(5):861-72, 2007.

What is claimed is:

1. A method of producing immune cells comprising:
   (a) obtaining induced pluripotent stem cells (iPSCs), wherein the iPSCs are reprogrammed from a population of somatic cells;
   (b) incubating the iPSCs in a first defined media comprising a GSK inhibitor, wherein the media is free or essentially free of BMP4, IL-3, Flt3 ligand, and GM-CSF to prepare cells for HPC differentiation;
   (c) culturing the cells produced in step (b) in a second defined media comprising BMP4, FGF2, and VEGF to promote mesoderm induction in a plurality of the cells;
   (d) culturing the cells produced in step (c) in a third defined media comprising IL-3 and Flt3 ligand, such that a plurality of the cells proliferate and differentiate into HPCs that exhibit increased expression of one or more of CD7, DLL4, CD144, and CD235 as compared to cells produced in step (c); and
   (e) culturing the HPCs produced in step (d) under conditions to promote immune cell differentiation, thereby producing immune cells.

2. The method of claim 1, wherein the immune cells are lymphoid cells.

3. The method of claim 2, wherein the lymphoid cells are T cells, B cells, and/or NK cells.

4. The method of claim 2, wherein HPCs that express CD34 and CD43 are cultured under conditions to promote lymphoid differentiation.

5. The method of claim 4, wherein culturing the HPCs to promote lymphoid differentiation comprises:
   (i) culturing HPCs in defined, feeder-free media on a surface coated with matrix and a Notch ligand; and
   (ii) maintaining the culture in the presence of one or more cytokines selected from the group consisting of SCF, TPO, IL-7, and Flt-3, thereby producing lymphoid cells.

6. The method of claim 5, wherein the defined media comprises ascorbic acid and nicotinamide.

7. The method of claim 6, wherein the ascorbic acid is present at a concentration of 50 µM to 1 mM.

8. The method of claim 6, wherein the nicotinamide is present at a concentration of 0.1 mM to 5 mM.

9. The method of claim 5, wherein the matrix is retronectin and the culture further comprises immobilized anti-CD3 antibody.

10. The method of claim 5, wherein the Notch ligand is DLL4.

11. The method of claim 5, wherein step (ii) is one to six weeks or two to four weeks.

12. The method of claim 2, wherein more than 10% of the lymphoid cells are positive for at least two of the markers selected from the group consisting of CD8, CD7, CD45, CD5, CD4, and CD3.

13. The method of claim 2, wherein the lymphoid cells retain the T cell receptor gene arrangement of the blood cells.

14. The method of claim 1, wherein the first defined media comprises blebbistatin and/or Rock inhibitors.

15. The method of claim 1, wherein the GSK3 inhibitor is CHIR99021.

16. The method of claim 1, wherein the first defined media further comprises VEGF, and FGF2.

17. The method of claim 1, wherein the cells are cultured as aggregates for steps (b)-(d) and the cells are individualized prior to step (e).

18. The method of claim 1, wherein steps (b) to (d) are performed using amine culture plates.

19. The method of claim 1, wherein the third defined media further comprises one or more of the cytokines selected from the group consisting of IL-3, IL-6, SCF, TPO, and BMP4.

20. The method of claim 1, wherein the third defined media comprises heparin.

21. The method of claim 1, wherein the population of somatic cells is a population of blood cells.

22. The method of claims 21, wherein the population of blood cells comprises T cells.

23. The method of claim 1, wherein the HPCs differentiate into at least 20 immune cells per input HPC.

24. The method of claim 1, further comprising isolating CD34 positive cells prior to step (e) by performing magnetic-activated cell sorting (MACS).

25. The method of claim 24, further comprising isolating cells positive for one or more of CD7, DLL4, CD144, and CD235.

* * * * *